United States Patent
Hirotsuka et al.

(10) Patent No.: US 10,653,412 B2
(45) Date of Patent: May 19, 2020

(54) PRE-TIED SURGICAL KNOTS FOR USE WITH SUTURE PASSERS

(71) Applicant: Ceterix Orthopaedics, Inc., Fremont, CA (US)

(72) Inventors: Mark Y. Hirotsuka, San Jose, CA (US); Michael Murillo, Menlo Park, CA (US); Yoav Ben-Haim, San Francisco, CA (US); Justin D. Saliman, Los Angeles, CA (US); Christopher P. Bender, Oakland, CA (US); Michael J. Hendricksen, Redwood City, CA (US); Stephen J. Peter, San Francisco, CA (US); Victoria C. Quitugua, Palo Alto, CA (US); Sarah-Marie Chan, Menlo Park, CA (US); Jennifer B. Fasman, Menlo Park, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 0 days.

(21) Appl. No.: 16/557,017

(22) Filed: Aug. 30, 2019

(65) Prior Publication Data

US 2020/0008796 A1    Jan. 9, 2020

Related U.S. Application Data

(63) Continuation of application No. 15/132,211, filed on Apr. 18, 2016, now Pat. No. 10,441,273, which is a continuation-in-part of application No. 13/758,994, filed on Feb. 4, 2013, now Pat. No. 9,314,234.

(60) Provisional application No. 61/698,528, filed on Sep. 7, 2012, provisional application No. 62/236,758, filed on Oct. 2, 2015.

(51) Int. Cl.
 A61B 17/04 (2006.01)
 A61B 17/062 (2006.01)
 A61B 17/06 (2006.01)

(52) U.S. Cl.
 CPC .......... *A61B 17/0482* (2013.01); *A61B 17/04* (2013.01); *A61B 17/0401* (2013.01); *A61B 17/0469* (2013.01); *A61B 17/0483* (2013.01); *A61B 17/0625* (2013.01); *A61B 2017/0474* (2013.01); *A61B 2017/0477* (2013.01); *A61B 2017/0496* (2013.01); *A61B 2017/06042* (2013.01)

(58) Field of Classification Search
 CPC . A61B 17/04; A61B 17/0401; A61B 17/0469; A61B 17/0482; A61B 17/0483; A61B 17/0625; A61B 2017/0474; A61B 2017/0477; A61B 2017/0496; A61B 2017/06042
 See application file for complete search history.

(56) References Cited

U.S. PATENT DOCUMENTS

| | | | |
|---|---|---|---|
| 8,808,299 B2* | 8/2014 | Saliman | A61B 17/0469 606/88 |
| 2009/0138029 A1* | 5/2009 | Saliman | A61B 17/0469 606/144 |
| 2011/0112556 A1* | 5/2011 | Saliman | A61B 17/0469 606/145 |

(Continued)

*Primary Examiner* — George J Ulsh
(74) *Attorney, Agent, or Firm* — Norman F. Hainer, Jr.

(57) ABSTRACT

Sutures with pre-tied knots for use in percutaneous surgical procedures and devices for easily and quickly tying complex suture knots are disclosed.

22 Claims, 66 Drawing Sheets

(56) References Cited

U.S. PATENT DOCUMENTS

2012/0283754 A1\* 11/2012 Murillo .............. A61B 17/0469
　　　　　　　　　　　　　　　　　　　606/145
2014/0236192 A1\* 8/2014 Hendricksen ...... A61B 17/0469
　　　　　　　　　　　　　　　　　　　606/144

\* cited by examiner

USE SUTURE CUTTER TO CUT TAILS

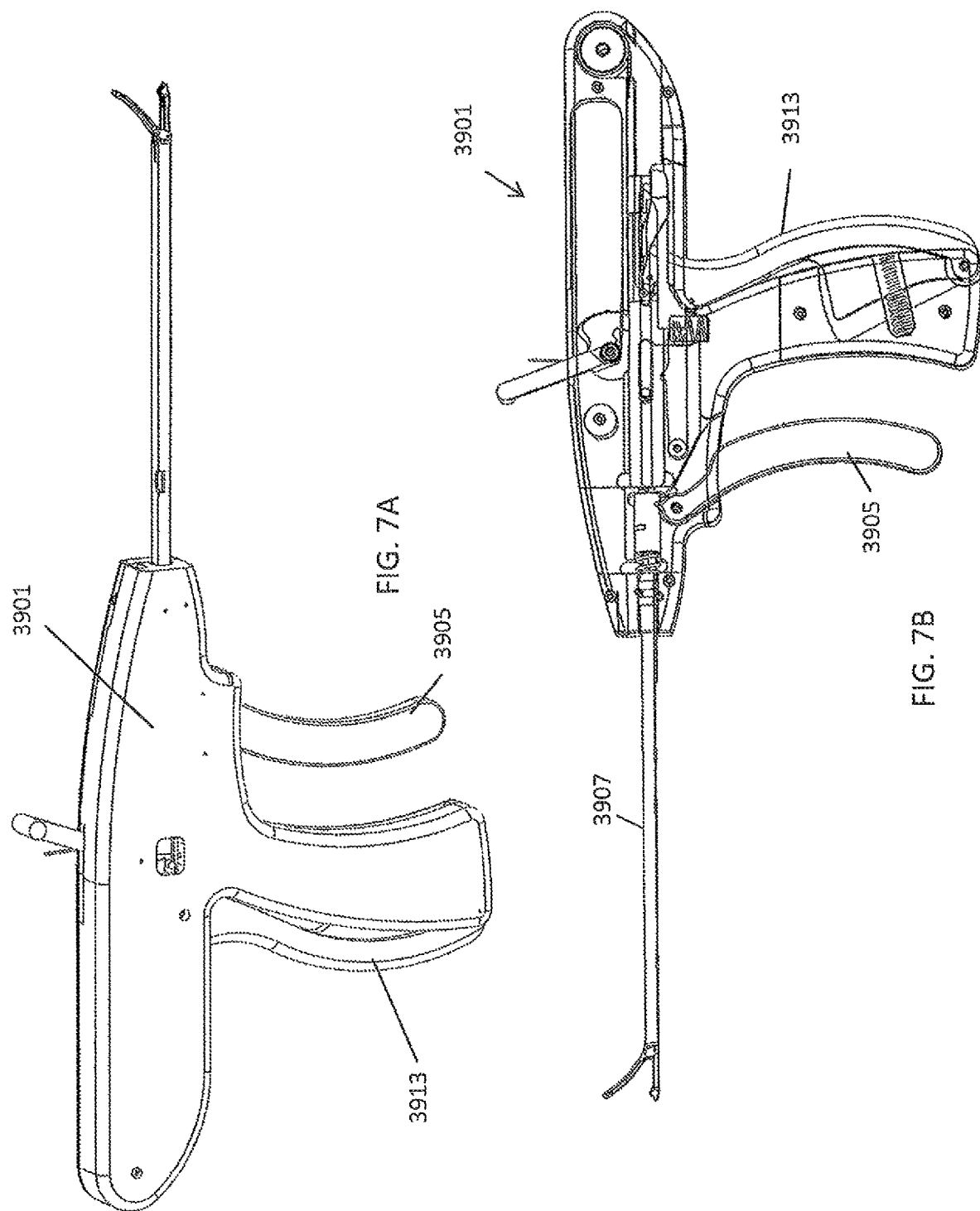

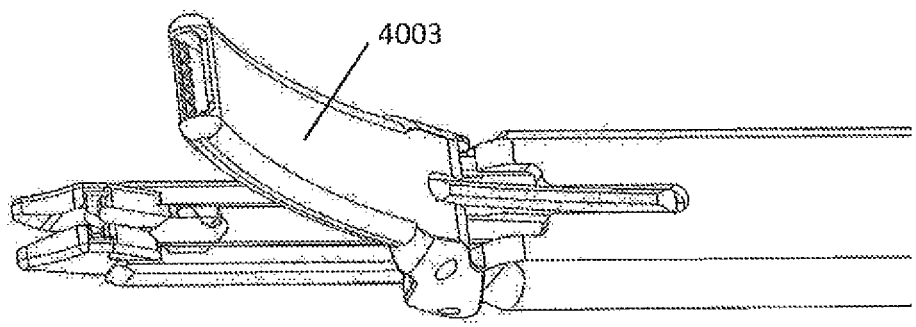
FIG. 8A
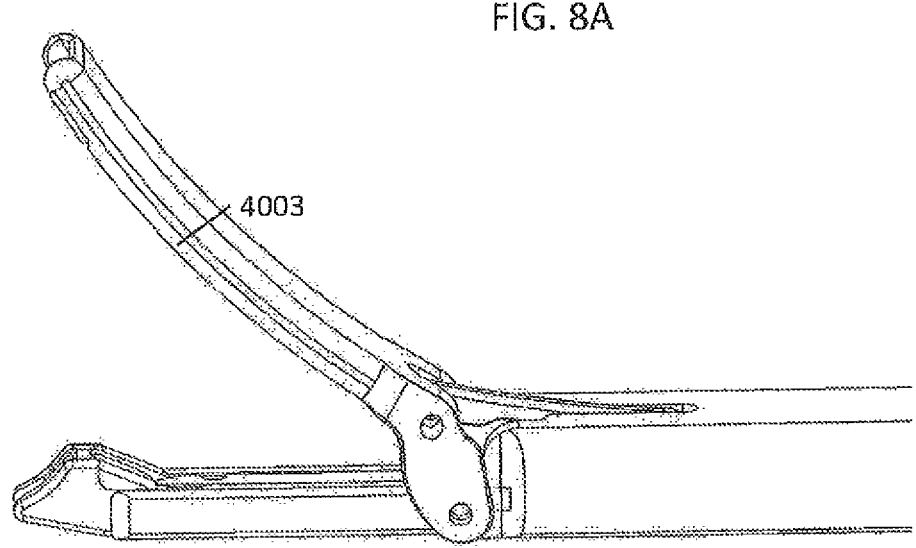
FIG. 8B
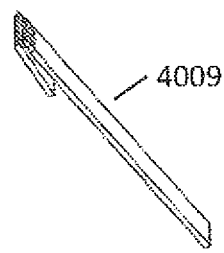
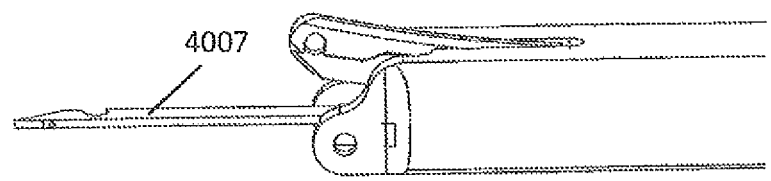
FIG. 8C

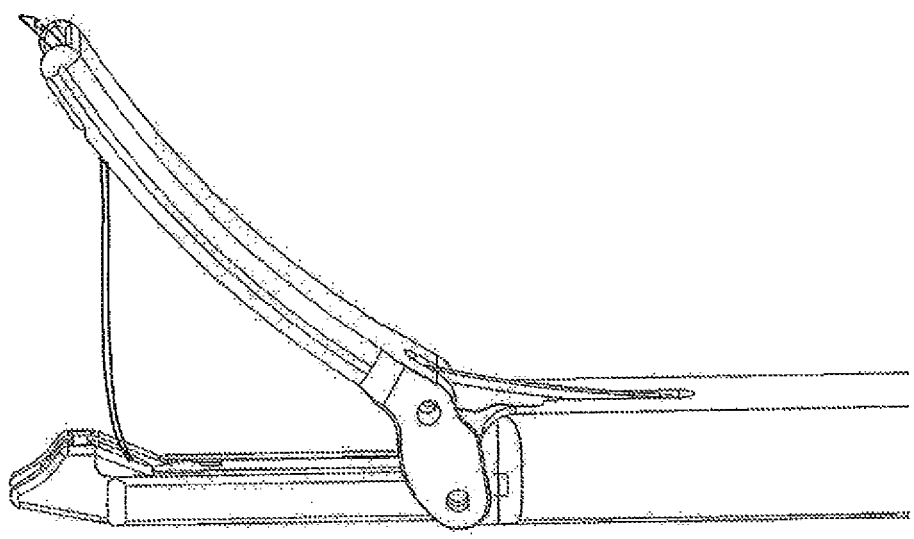
FIG. 8D
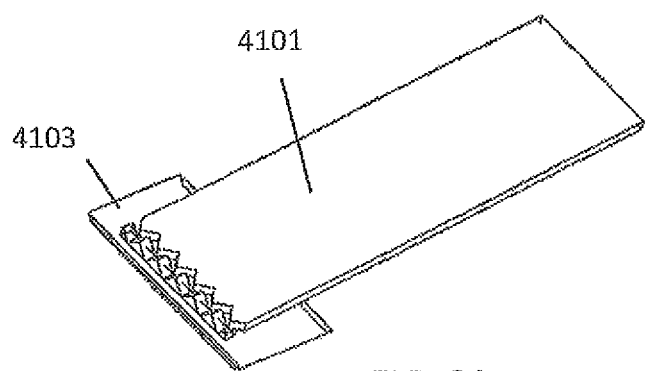
FIG. 9A
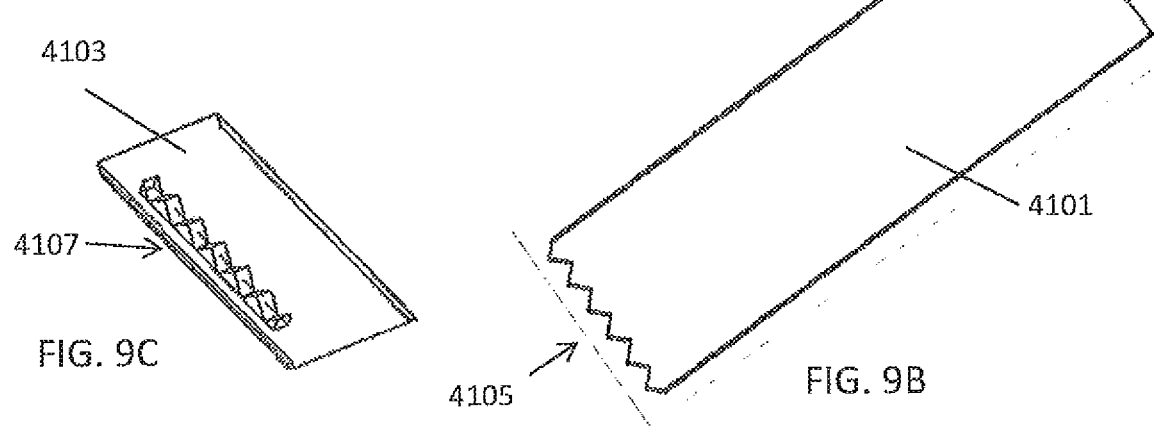
FIG. 9C
FIG. 9B

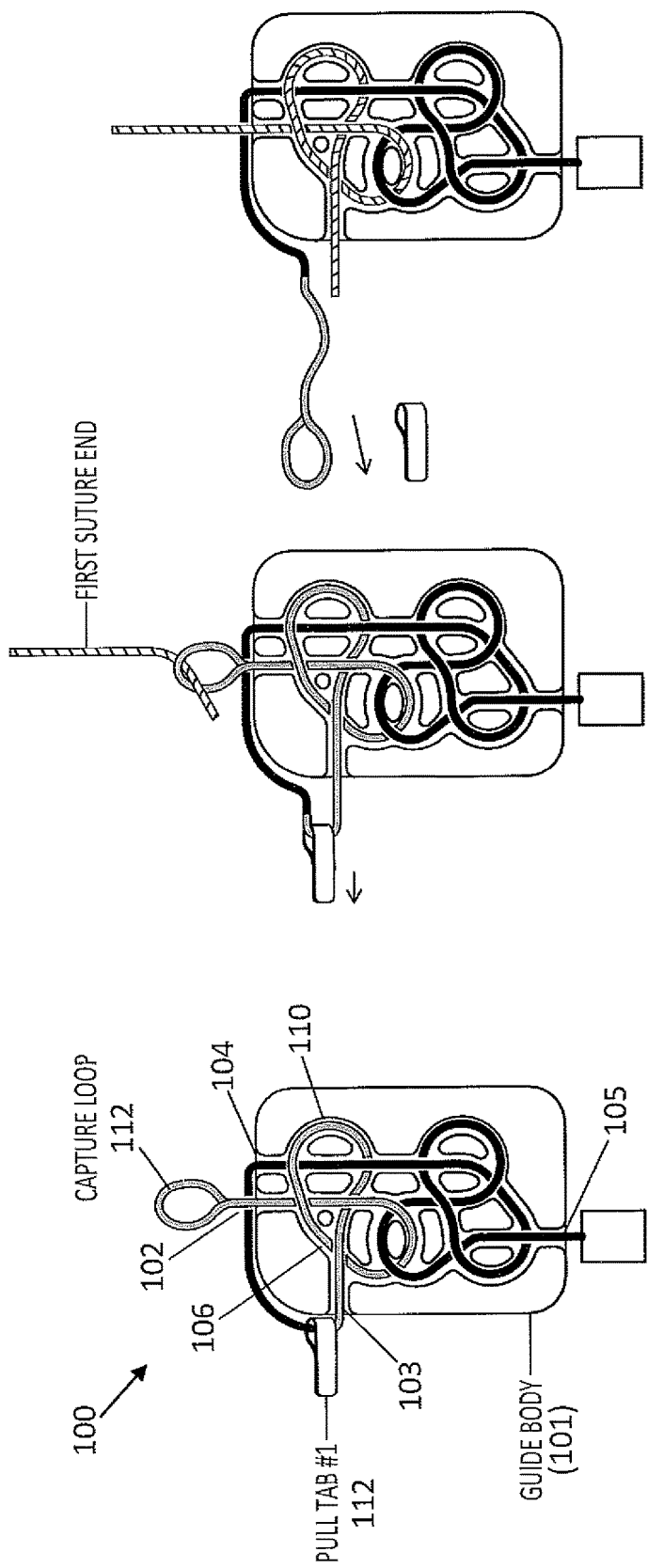

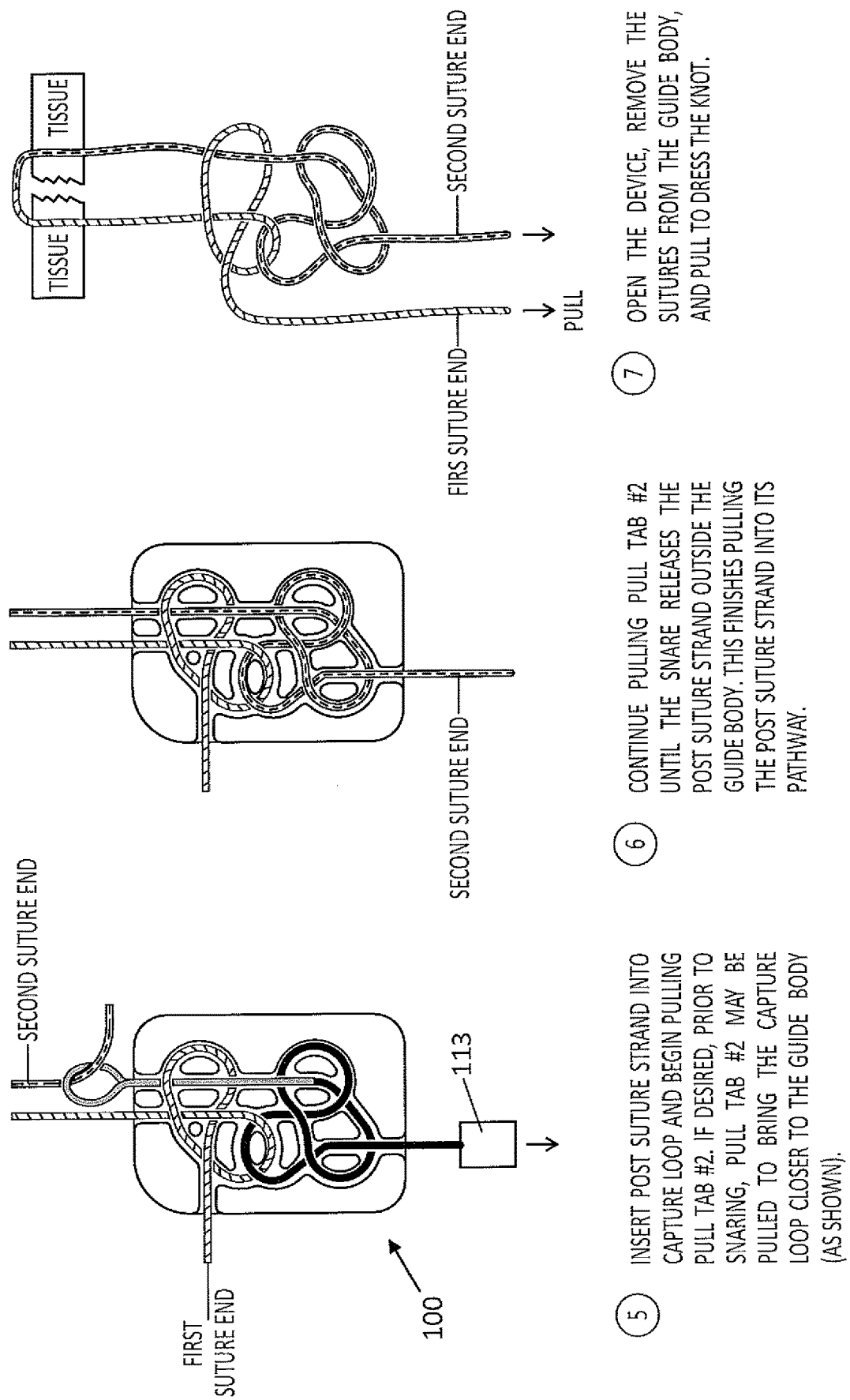

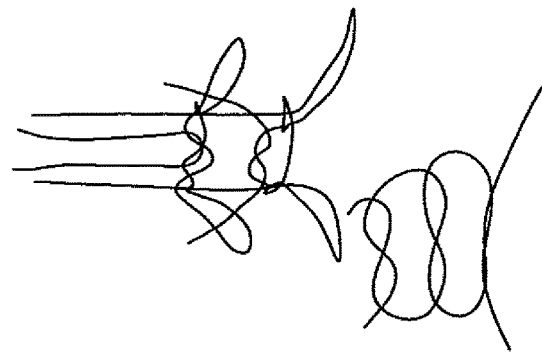
FIG. 33
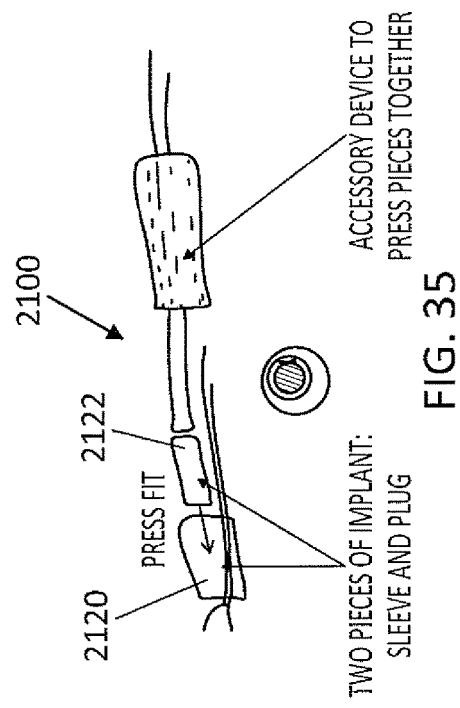
FIG. 35
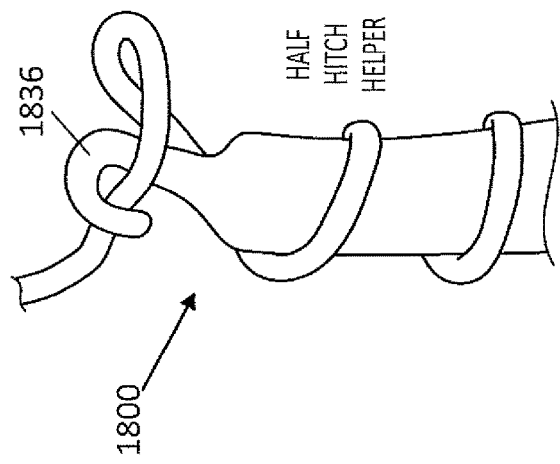
FIG. 32
FIG. 34

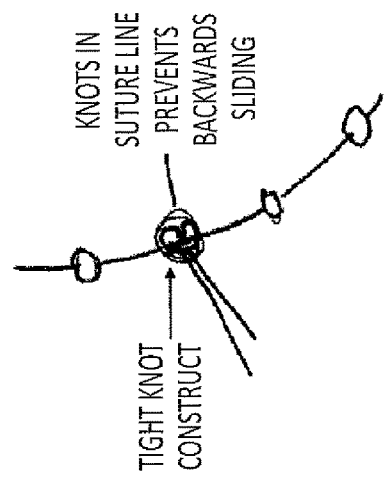
FIG. 40
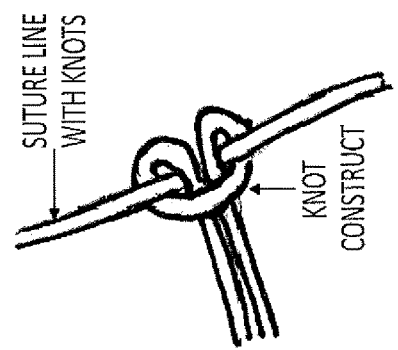
FIG. 41B
FIG. 38
FIG. 41A
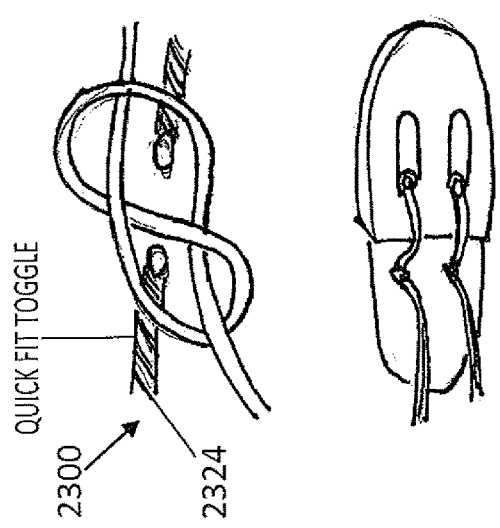
FIG. 37
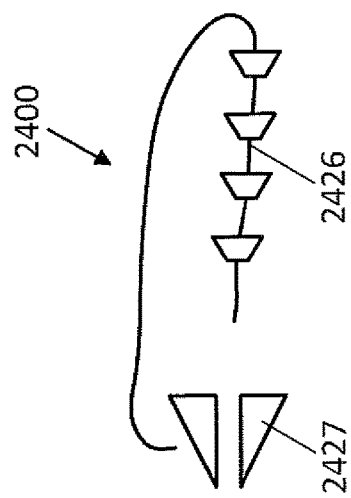
FIG. 39

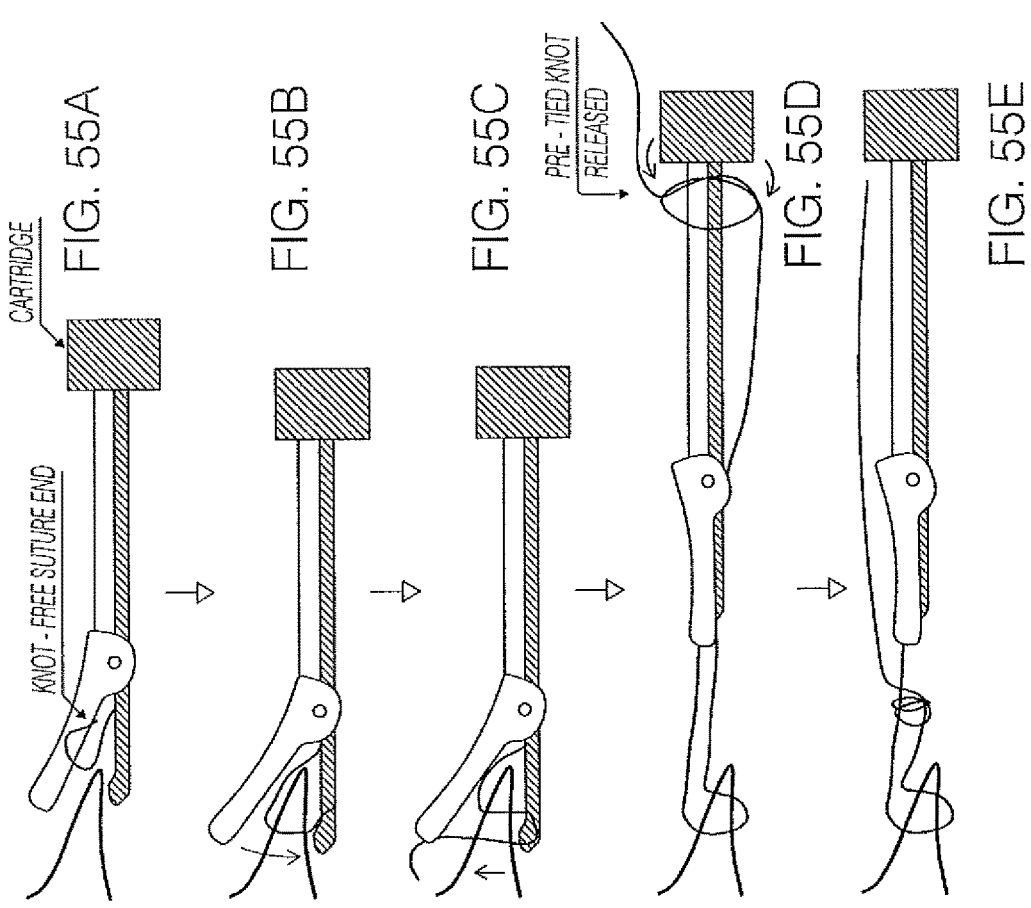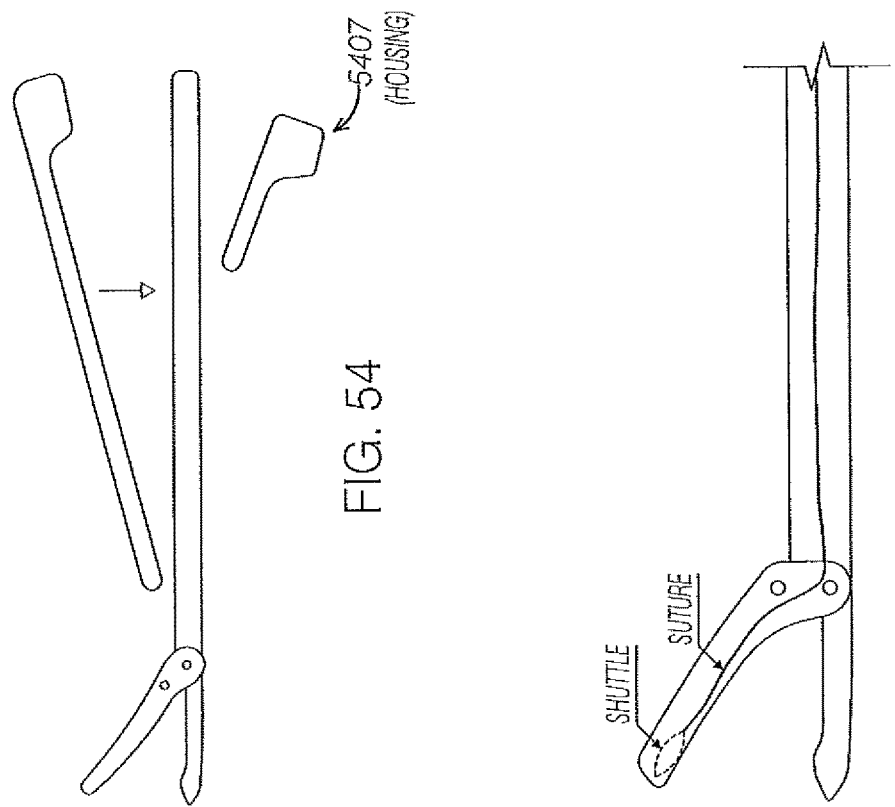

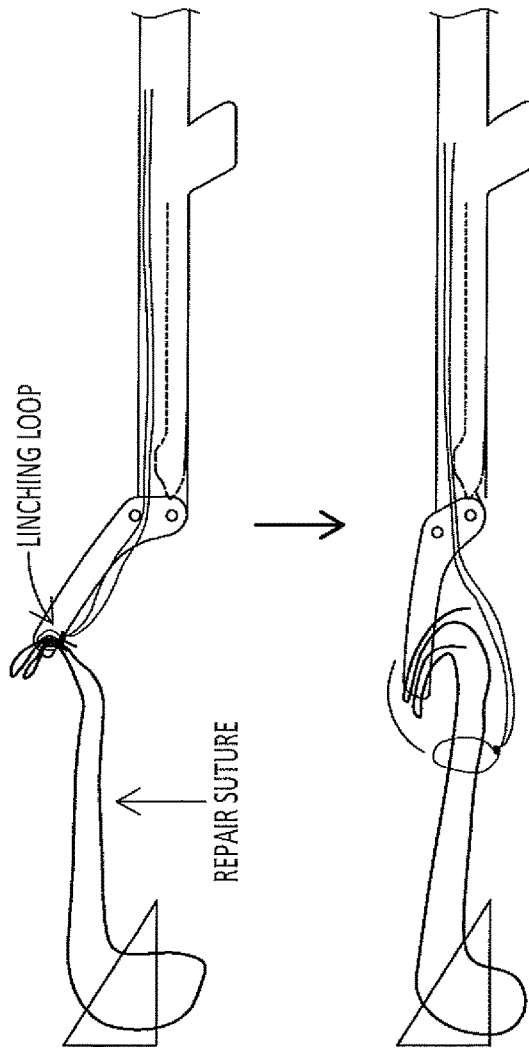
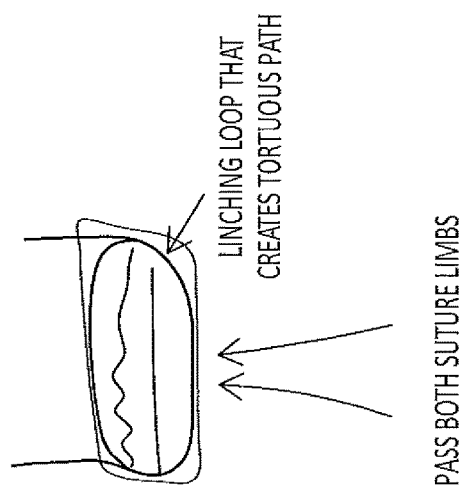
FIG. 57
FIG. 58
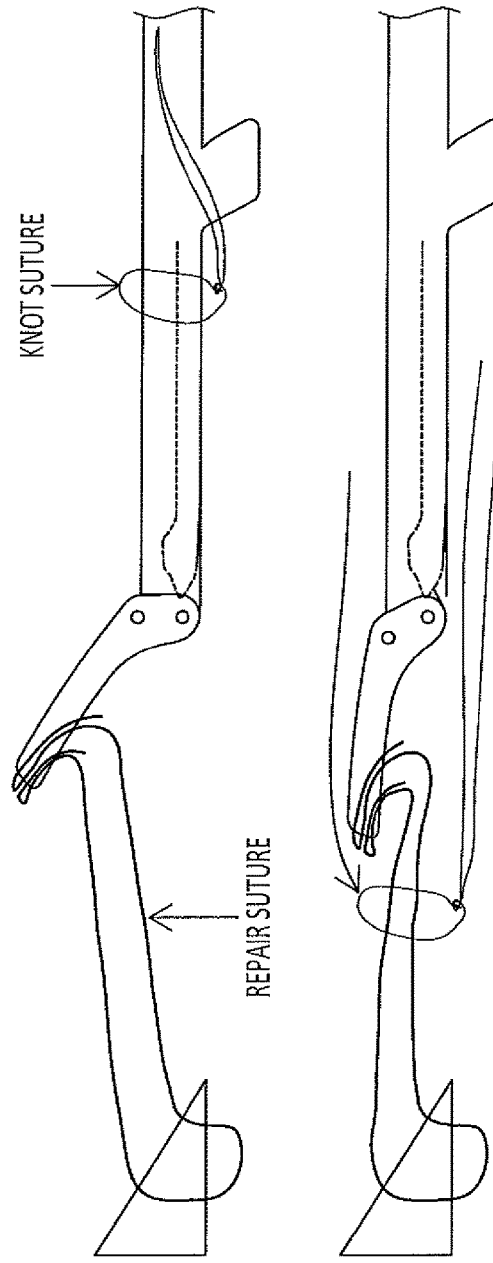
FIG. 59A
FIG. 59B

PRE-TIED SURGICAL KNOTS FOR USE WITH SUTURE PASSERS

CROSS REFERENCE TO RELATED APPLICATIONS

This patent application claims priority as a continuation to U.S. patent application Ser. No. 15/132,211 filed Apr. 18, 2016, which claims priority as a continuation-in-part to U.S. patent application Ser. No. 13/758,994, filed on Feb. 4, 2013 and titled "PRE-TIED SURGICAL KNOTS FOR USE WITH SUTURE PASSERS, now U.S. Pat. No. 9,314,234 which claims priority to U.S. Provisional Patent Application No. 61/698,528, filed on Sep. 7, 2012 and titled "PRE-TIED SURGICAL KNOTS FOR USE WITH SUTURE PASSERS."

This patent application also claims priority to U.S. Provisional Patent Application No. 62/236,758, filed Oct. 2, 2015 and titled "KNOT TYING ACCESSORY". Each of these patent applications is herein incorporated by reference in its entirety.

The pre-tied knots described herein may be used, in particular, with, or as part of any of the suture passer devices and systems described in the following patent applications, each of which is herein incorporated by reference in its entirety. Specifically: U.S. patent application Ser. No. 11/773,388, filed on Jul. 3, 2007, titled "METHODS AND DEVICES FOR CONTINUOUS SUTURE PASSING," now Publication No. US-2009-0012538-A1; U.S. patent application Ser. No. 12/972,222, filed on Dec. 17, 2010, titled "METHODS AND DEVICES FOR CONTINUOUS SUTURE PASSING," now Publication No. US-2011-0087246-A1; U.S. patent application Ser. No. 13/462,760, filed on May 2, 2012, titled "METHODS OF MENISCUS REPAIR," now Publication No. US-2012-0239062-A1; U.S. patent application Ser. No. 13/006,966, filed on Jan. 14, 2011, titled "METHODS FOR CONTINUOUS SUTURE PASSING," now Publication No. US-2011-0130773-A1; U.S. patent application Ser. No. 13/090,089, filed on Apr. 19, 2011, titled "METHODS OF MENISCUS REPAIR," now Publication No. US-2011-0218557-A1; U.S. patent application Ser. No. 12/291,159, filed on Nov. 5, 2008, titled "SUTURE PASSING INSTRUMENT AND METHOD," now Publication No. US-2010-0331863-A2; U.S. patent application Ser. No. 12/972,168, filed on Dec. 17, 2010, titled "SUTURE PASSING INSTRUMENT AND METHOD," now Publication No. US-2011-0152892-A1; U.S. patent application Ser. No. 13/062,664, filed on Apr. 19, 2011, titled "KNOTLESS SUTURE ANCHORS," now Publication No. US-2011-0190815-A1; U.S. patent application Ser. No. 12/620,029, filed on Nov. 17, 2009, titled "METHODS OF SUTURING AND REPAIRING TISSUE USING A CONTINUOUS SUTURE PASSER DEVICE," now Publication No. US-2010-0130990-A1; U.S. patent application Ser. No. 12/942,803, filed on Nov. 9, 2010, titled "DEVICES, SYSTEMS AND METHODS FOR MENISCUS REPAIR," now Publication No. US-2011-0112556-A1; U.S. patent application Ser. No. 13/462,728, filed on May 2, 2012, titled "DEVICES, SYSTEMS AND METHODS FOR MENISCUS REPAIR," now Publication No. US-2012-0265221-A1; U.S. patent application Ser. No. 13/114,983, filed on May 24, 2011, titled "SUTURING AND REPAIRING TISSUE USING IN VIVO SUTURE LOADING," now Publication No. US-2011-0270280-A1; U.S. patent application Ser. No. 13/347,184, filed on Jan. 10, 2012, titled "IMPLANT AND METHOD FOR REPAIR OF THE ANTERIOR CRUCIATE LIGAMENT," now Publication No. US-2012-0179254-A1; U.S. patent application Ser. No. 13/247,892, filed on Sep. 28, 2011, titled "MENISCUS REPAIR," now Publication No. US-2012-0283750-A1; U.S. patent application Ser. No. 13/323,391, filed on Dec. 12, 2011, titled "SUTURE PASSER DEVICES AND METHODS," now Publication No. US-2012-0283753-A1; and U.S. patent application Ser. No. 13/462,773, filed on May 2, 2012, titled "SUTURE PASSER DEVICES AND METHODS," now Publication No. US-2012-0283754-A1, each of which is incorporated by reference in its entirety.

Many of the pre-tied knot variations described herein were developed for use with one or more of these suture passer devices, and thus may be particularly well adapted for use with these systems. However, the pre-tied knot methods and systems described herein may also be used with other suture passers, or even without suture passers, in order to secure one or more sutures.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to suturing techniques, devices and methods, including pre-tied knots for surgical use and methods of forming these knots as well as sutures, suture passers, and other devices including or for forming surgical knots. More particularly, described herein are pre-tied suturing knots and methods of using them minimally invasively (e.g., endoscopically). Also described herein are suture methods that use a pre-tied knot (or other fastener) attached to the suture to aid in passing the suture, as well as suture passers adapted for use with suture that has a knot, fastener or other enlarged-diameter region so that the enlarged region (e.g., knot) may be passed through tissue. Finally, described herein are accessory devices, methods, and kits for tying knots in sutures.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

During or after performance of a surgical procedure, tissues must be stitched or sutured to allow or encourage healing. Suturing, that is, the tying a tissue with a suture (e.g., thread), is well-known in the art. Moreover, pre-tied sutures and methods of suturing for external surgical use likewise are known, such as is described in U.S. Pat. No. 3,580,256 to Wilkinson et al. The Wilkinson patent describes a pre-tied suture that is encased in a see-through material, taking the form of a thin, flat wafer. In use, the surgeon stitches the tissue together and then directs the needle through the loops in the wafer and draws it tight in order to make the knot. Clearly, such a convention could not be used for endoscopic and other internal surgical techniques.

In contrast, minimally invasive surgery, such as endoscopic surgery, is performed within the interior of a body, including a body cavity or hollow organ, with the help of an endoscope or similar device to visualize the interior portions of the body where the surgery is to be performed. Small, low-profile or compact devices, such as suture passers, may be used to pass a suture through the tissue, and subsequently tie off the suture. The surgeon may observe the surgical procedure through a visual device whose output is displayed on a video monitor.

In order to perform the suturing within patient's body, a suture passer with a tissue penetrator (e.g., needle) element may pass through the tissue one or more times (including through a tissue and a non-tissue material, such as an implant, graft, etc.). The tissue penetrator may pass a suture directly, or it may pass an element that can later pull a suture through the tissue. A problem may arise in manipulating the tissue penetrator (e.g., needle) for easily tying a knot for closing the surgical incision in situ. It is challenging to tie off or otherwise secure the free end or ends of a suture, particularly minimally invasively. Thus, it is to be appreciated that a pre-tied suture, employable with a suture passer or grasping instrument, could greatly facilitate minimally invasive and other surgical procedures (even including open procedures). The present invention is directed to such methods and systems for knotting suture that allow a pre-tied knot to be present, pre-attached or pre-tied onto the suture before performing the surgical procedure.

It is also desirable to suture tissue using a suture passer that can reliably transfer a suture through the tissue without dropping the suture. Described herein are suture passers and methods of passing sutures that enhance reliability by passing a suture that is pre-knotted or otherwise includes an enlarged region on the suture (e.g., near the end region of a suture) to reliably pass the suture (including the knot) through the tissue.

Presently, sutures that are tied to maintain a wound in a closed position are hand-tied by the surgeon performing the procedure. Forming the suture knot and tying off the suture knot such that the knot does not slip or is too slack with respect to the tissue opening can be a challenging final step in what may already be a challenging and arduous procedure. In some instances, there is limited space and clearance for a surgeon to make the necessary movements of the tool or of their hand in the area that is being sutured, such as areas near bone. In those instances, tying a steadfast suture against the tissue to be held together may be challenging. Finally, while an operating room is technically sterile, it would still be advantageous to lessen the time an area being operated on is left open to potential infectious agents. Thus, decreasing the time it takes to tie off a suture is desirable.

While suture-related instruments such as suture passers and knot pushers have been developed to aid in reducing suturing time and suturing difficult to access areas of the body, these devices still fall short of being able to quickly tie adequate suture knots. For example, suture pushers may be able to stitch tissue even in hard to reach areas, but once a suture requires tying off, it is still a challenge for a surgeon to easily loop the suture ends together using a suture pusher.

Surgical staples are an alternative to sutures for quickly closing a wound. Unfortunately, surgical staples leave unpleasing closure marks upon healing. Thus, it would be desirable to have a device for providing an easy way to tie off a suture where there is no steep learning curve for using such a device.

SUMMARY OF THE DISCLOSURE

The present invention relates to pre-tied knots. In particular, described herein are pre-tied knots that maybe used percutaneously with a suture passer. The pre-tied knots may include a knot body and a leader snare. The suture with a pre-tied knot may (prior to being knotted to the other end or a different suture) be passed through the tissue. Thus, the pre-tied knots described herein are particularly helpful for use with suture passers that may be used minimally invasively (e.g. percutaneously). Also described are methods of knotting a suture using the pre-tied knots described herein, including in particular, methods of percutaneously repairing a torn meniscus using these pre-tied knots.

In general, described herein are sutures including pre-tied knots. The pre-tied knot may include a knot body that is secured to, and may be formed of, the suture. The pre-tied knot may also include a leader snare that is tied to the suture by the knot body. The leader snare typically includes a first end with a loop region (e.g., a bight) that can be threaded to hold an end of the suture, and a second end which is a tail or pull tail that can be pulled on to pull the leader snare out of the knot body. When an end of the suture is threaded into the loop/bight region, pulling the tail of the leader snare results in closing the loop of suture at the knot body. The loop can then be cinched and/or the knot body tightened to securely knot the loop.

For example a suture may have a pre-tied knot including: an elongate flexible length of suture (formed of suture material) having a first end and a second end; a knot body formed from the suture material at a region near the first end of the suture, the knot body having one or more loops of the suture material, wherein each loop has at least one crossing point; and a leader snare formed of a length of linear and flexible material that is distinct from the suture material forming the knot body, the leader snare passing through the one or more loops of the knot body, wherein the leader snare comprises a loop or bight extending from a first end of the knot body and a pull end extending from a second end of the knot body, wherein the knot body and leader snare are sufficiently flexible and narrow of profile to be pulled through a tissue behind a tissue penetrator. The tissue penetrator may be any of the tissue penetrators incorporated by reference above as part of a suture passer, or it may be a simple needle (including curved needles).

The knot body may have one, two, three, four, five or more loops of suture material. In some variations, the knot body includes three or more loops of suture material.

The leader snare may be formed of a second piece of suture material. The loop or bight of the leader snare may extend towards the second end of the suture and the pull end of the leader snare may extend towards the first end of the suture. In some variations, the material forming the leader snare has a larger diameter than the suture.

In some variations, the knot body is configured to slide along the length of the suture. In other variations the knot body is relatively fixed along the length of the suture.

Although the examples provided above include knot bodies formed of the suture (e.g., of the length of suture), in some variations the knot body is a separate length of material (e.g., suture material) that is tied to the length of suture. Alternatively, the knot body may be formed of a some other material (non-suture material) including polymeric materials, metals, alloys, ceramics, etc.

The pre-tied knot may be positioned at any position along the length of the elongate suture. In some variations the pre-tied knot body is located at the proximal or distal ends. In some variations the pre-tied knot is locate near the middle region of the suture. In some variations, the pre-tied knot is located proximal to the distal end of the device. As mentioned above, in some variations, the pre-tied knot body may be formed of a region of the elongate length of suture.

Any of the sutures having pre-tied knots described herein may be used to suture tissue, and in particular to knot a loop of suture through and/or around tissue. For example, described herein are methods of percutaneously tying a loop of suture around tissue using a pre-tied knot, wherein the suture has a proximal end, a distal end, and a pre-tied knot formed between the proximal and distal ends, wherein the pre-tied knot is tied around a leader snare so that a loop of the leader snare extends from the pre-tied knot in a first direction and a tail of the leader snare extends from the pre-tied knot in a second direction, the method comprising: percutaneously passing the distal end of the suture through the tissue; percutaneously passing the leader snare through the tissue; passing the distal end of the suture through the loop of the leader snare; forming a loop of suture by pulling the tail of the leader snare to draw the suture through the pre-tied knot while removing the leader snare from the pre-tied knot; and cinching the loop of suture around the tissue.

As mentioned, in some variation the methods may be used to knot a loop of suture using a suture passer. For example, percutaneously passing the distal end of the suture comprises using a suture passer to pass the distal end of the suture. Percutaneously passing the leader snare may comprise using the suture passer to pass the leader snare. Percutaneously passing the leader snare may comprise percutaneously passing the loop of the leader snare through the tissue.

Any of these methods may also be used to form a loop of suture around a torn meniscus. For example, percutaneously passing the distal end of the suture may comprise percutaneously passing the distal end of the suture from the inferior to the superior side of a meniscus.

Cinching may comprise pulling the distal end of the suture, which may reduce the size of the loop. Cinching may also or alternatively comprise tightening the pre-tied knot over the suture. For example, the knot body may be tightened by pulling an end of the length of material forming the knot body to reduce the size (e.g., diameter) of any loops forming the knot body. As mentioned, in some variations, the knot body of the pre-tied knot is formed from the suture; in some variations the knot body is formed of a separate length of suture or other material.

In one variation, a method of percutaneously forming a loop of suture around a tear in a meniscus using a pre-tied knot, wherein the suture has a proximal end, a distal end, and a pre-tied knot formed between the proximal and distal ends, and wherein the pre-tied knot is tied around a leader snare so that a loop of the leader snare extends from the pre-tied knot in a first direction and a tail of the leader snare extends from the pre-tied knot in a second direction, may include the steps of: percutaneously passing the distal end of the suture from an inferior surface to a superior surface of the meniscus; percutaneously passing the leader snare from the inferior surface to the superior surface of the meniscus; passing the distal end of the suture through the loop of the leader snare; forming a loop of suture by pulling the tail of the leader snare to draw the distal end of the suture from the superior surface to the inferior surface and through the pre-tied knot while removing the leader snare from the pre-tied knot; and cinching the loop of suture around the meniscus.

In some variations, a method of percutaneously forming a loop of suture around a tear in a meniscus using a pre-tied knot, wherein the suture has a proximal end, a distal end, and a pre-tied knot formed between the proximal and distal ends, wherein the pre-tied knot is tied around a leader snare so that a loop of the leader snare extends from the pre-tied knot in a first direction and a tail of the leader snare extends from the pre-tied knot in a second direction, includes: percutaneously passing the distal end of the suture from a superior surface to an inferior surface of the meniscus; percutaneously passing the leader snare from the superior surface to the inferior surface of the meniscus; passing the distal end of the suture through the loop of the leader snare; forming a loop of suture by pulling the tail of the leader snare to draw the distal end of the suture from the inferior surface to the superior surface and through the pre-tied knot while removing the leader snare from the pre-tied knot; and cinching the loop of suture around the meniscus.

Also described herein are methods of using a suture having a pre-tied suture knot. For example, described herein are methods of suturing tissue using a length of suture with a pre-tied knot, these methods including the steps of: passing a suture through a tissue, wherein the suture comprises a knot body at a region of a first end of the suture, the knot body having one or more loops of the suture around a leader snare, wherein each loop has at least one crossing point, and further wherein the leader snare comprises a loop or bight formed of a length of linear and flexible material extending from a first end of the knot body and a pull end extending from a second end of the knot body; passing a second end of the suture through the loop or bight of the leader snare; pulling the pull end of the leader snare to draw the second end of the suture through the knot body and removing the leader snare from the knot body; and tightening the knot body around the second end of the suture and knotting the suture.

The step of passing the suture through the tissue may further comprises passing the knot body through the tissue. As mentioned, the pre-tied knot may be sufficiently flexible and narrow diameter to pass through the tissue behind a tissue penetrator.

In some variations, the method also includes the step of sliding the knot body along the suture.

In some variations, the knot body may be tightened by pulling the first and second ends of the suture. Once the knot is tightened, the free ends of the suture may be cut and removed.

The step of passing the suture through the tissue may include passing the suture endoscopically using a suture passer. As mentioned above, in particular, the methods described herein may be used to repair a torn meniscus of the knee. Thus, the method may include passing the suture through the meniscus tissue. In some variations, passing the suture comprises passing the second end of the suture through a first region of the tissue and passing the first end of the suture and the knot body through a second region of the tissue.

In some variations, described herein are method of passing a suture through tissue using a tissue passers in which the portion of the suture passed by the tissue passer includes a knot (or other enlarged region) that is driven through the tissue. Although it is counterintuitive to pass a knotted portion of a suture through the tissue during repair of the tissue, the inventors have found this method to be surprisingly effective. Also described herein are suture passers that may be used in even the most constricted anatomical regions for minimally invasive (e.g., arthroscopically) passing a suture including a knotted region through the tissue. In some variations the devices and methods may be adapted to pass multiple lengths of suture (having multiple knots or enlarged regions on the suture) through the tissue using the same device without having to remove the device from the tissue to reload between passes.

Also described herein are devices, methods and kits for forming a simple or complex suture knot at a first and a second end of a piece of suture. The devices and methods disclosed herein are able to quickly and easily form a non-slipping knot that can be positioned close to the tissue sections to be closed. While it is contemplated that the knot tying accessories will be reusable, it is also contemplated that sterile kits be provide the have guide threads pre-threaded through the knot tying device ready for immediate use when needed.

The devices and methods described herein are for quickly tying off two free ends of a suture. The devices of the present invention comprise a guide body having internal pathways, a guide thread that is able to thread the guide body. The guide body can be opened and closed. In one example, the guide body includes openings disposed on the guide body where the sections of the guide thread is exposed at these openings. The guide body has a top and a bottom side that fit together when closed. The guide body may be opened to expose an interior space comprising a series of pathways that are disposed on the top and bottom side of the guide body. The series of pathways may be only on one side of the guide body or a complete pathway may be formed when the top and bottom sides are fitted together. In other instances, the pathways on the top and bottom are different and aid in forming different portions of the suture knot. The interior space including a convoluted pathway that crosses over itself at more than one location within the guide body. The convoluted pathway in some examples are essentially planar and a piece of guide thread can be wound in a particular pattern through the convoluted pathway.

The convoluted pathway with in the internal space of the guide body may include a series of channels in which the guide thread can be placed. In other examples, the convoluted pathway is delineated with posts or a series of protruding bodies that allow for the guide body to be wound past some or all of the posts or protruding bodies. There may be more than one path through the convoluted pathway that the guide thread can take when placed within the convoluted pathway. In some instances, the convoluted pathway may be defined by a combination of channels and protruding bodies. Whether the convoluted pathway is a series of channels, protruding bodies, or a combination of both, the path that the guide thread take within the guiding bodies generally take on soft curves able to easily slight within a channel or past the protruding bodies.

In an exemplary embodiment, the guide thread has a capture loop on one end while the other end is free. The length of the guide thread is such that there is not an excess of thread length once the guide thread has been laced through the desired channels or past the series of protruding bodies. Once properly placed within the guide body, the end of the guide thread having the capture loop extends from the guide body at a first location. A bight of guide thread is exposed at a second location with regard to the guide body, and the free end of the guide thread trails out of and away from the guide body at a third location.

The capture loop of the guide thread functions to securely hold a piece of suture so that the corresponding length of suture may be pulled through the entire length of the convoluted pathway without breaking free. The capture loop may also be a sliding knot that is able to cinch down and hold onto a piece of suture. In some examples, the capture is constructed from the same length of thread as the guide thread and is made from the same material. In other examples, the capture loop can be constructed from a material different than that of the guide thread. In some instances, the capture loop may be constructed from a metallic material. The capture loop may have a collapsible state for coupling and holding onto a suture end, and the capture loop may have an open state where the suture end is initially thread through the capture loop and when the suture is ready to be released after being threaded through the convoluted pathway of the guide body.

The knot tying device may also include pull tabs. The pull tabs are releasably coupled to the guide thread at locations where the guide thread is exposed with regards to the guide body. The pull tabs, when pulled in the proper sequence, aid a user in pulling the guide thread and the appropriate suture end through the convoluted pathway of the guide body such that the suture ends replace the guide thread within the convoluted pathway of the guide body.

The knot tying devices disclosed herein also have other forms that are able to maintain the guide thread in a particular pattern. In some other examples, the free suture ends may be directly threaded into the knot tying device, where the suture end may be wound around the device in a pattern for forming a knot. Some of the knot tying devices described below may be used in conjunction with existing suturing devices such a suture passer or a suture knot pusher.

In some examples of the knot tying device shown, no actual accessory device is provided for. In these embodiments, the suture itself has a unique element. For example, the suture may have a pre-formed knot bundle where the pre-formed knot bundle is maintained within a suturing device such as a suture passer or a suture pusher.

Also described herein are methods for using the various embodiments of the knot tying devices described. In some instances, instructions may be included with any of the knot tying devices included to aid the user in using the device. In other instances, there may be markings on the actual device for instructing the user on how to thread the guide thread within the convoluted pathway of the guide body and the order for pull the pull tabs that lead to replacing the guide thread with the suture ends.

Finally, also described herein are kits that may be provided for either a single use or multiple uses. The advantage of having a single use device is that the device will be maintained within a sterile environment until needed. Also, the surgeon performing the suturing will be ensured that he will have all the elements of the knot tying accessory at his disposal when the time comes for tying off a suture.

BRIEF DESCRIPTION OF THE DRAWINGS

FIGS. 5A-5K illustrate another variation of a pre-tied knot. FIGS. 5B and 5K show the pre-tied knot used with a suture anchor.

FIGS. 7A-7C show one variation of a suture passer.

FIGS. 8A, 8B, and 8D show top and two side perspective views, respectively of the distal end of the suture passer shown in FIG. 7A.

FIG. 8C illustrates the arrangement of the tissue penetrator and suture stripper in the distal end region of the suture passer of FIG. 7A.

FIGS. 9A-9C show a suture stripper including a stripper plate (FIG. 9B) and base (FIG. 9C).

FIGS. 14A-14J illustrate one method of passing a suture having knotted ends as described herein.

FIGS. 15A-15F are drawings of a first embodiment of a knot tying accessory where a guide thread with has been placed within a convoluted path of a guide body. The guide thread includes a capture loop at one end. A first and a second pull tab are shown attached to the guide thread. FIG. 15B is a drawing showing the first embodiment where a first suture end threaded through the capture loop and where the first pull tab has started to be pulled. FIG. 15C is a drawing showing the first embodiment where the first pull tab has completely pulled the guide thread and now the suture end has replaced a portion of the thread guide within the guide body. FIG. 15D is a drawing showing the first embodiment where a second suture leg/end has been threaded through the capture loop after the capture loop has traveled through a portion of the guide body and exited at the second opening on the guide body. FIG. 15E is a drawing showing the first embodiment wherein the second suture leg/end has been pulled through a latter portion of the guide body. FIG. 15F is a drawing showing the first embodiment where the first and the second ends of the suture has been removed from the guide body and is ready to be tightened against portions of tissue being sutured.

FIG. 25A shows the knot tying accessory in an open state while FIG. 25B shows the knot tying accessory in a closed state.

FIG. 30A shows a side view of this embodiment while FIG. 30B shows a top view.

FIG. 32 is a drawing showing a tool for easily forming a half hitch.

FIG. 33 is a drawing showing the formation of a stronger knot using two snares.

FIG. 34 is a drawing of a knot tying accessory device that are implantable.

FIG. 35 is a drawing of a second embodiment of an implantable knot tying accessory device having a sleeve and a plug.

FIG. 36B shows a top view where the top and bottom portions of the clasp are aligned. FIG. 36C is a top view of the accessory where the top and bottom portions of the clasp are not aligned. FIG. 36D is a cross-sectional view of the device.

FIG. 37 is a drawing showing another embodiment of an implantable knot tying accessory device having an implantable toggle.

FIG. 38 is a drawing showing another embodiment of an implantable knot tying accessory device having a structure for bringing together and maintaining tissue.

FIG. 39 is a drawing showing another concept for bringing together and maintaining tissue is a suture with knots.

FIG. 40 is a drawing showing a variation of concept for bringing together and maintaining tissue is a suture with knots having a loop formed from dividing the width of the suture in two.

FIGS. 41A and 41B is a drawing showing a suture line with knots can also be slid through a pre-tied, sliding knot construct such as a girth hitch.

FIG. 54 is an example of a suture passer cartridge pre-loaded with a knot.

FIGS. 55A-55E are other examples illustrating operation of a suture passer holding a pre-tied knot.

FIG. 56 is an example of a suture passer having a suture with a loop or shuttle region at one preloaded end (in the upper jaw).

FIGS. 57 and 58 illustrate another variation of a suture passer including a cinching loop that creates a path after passing the suture using the device, so that the knot may be formed automatically.

FIGS. 59A-59B illustrate a suture passer that includes a separate knot-forming element (suture, wire, etc.) that is passed over the ends of a suture that has been passed through the tissue, as illustrated. In this example the suture is passed and cinched, and all four ends may be trimmed or knotted together.

DETAILED DESCRIPTION

Figure 1A:
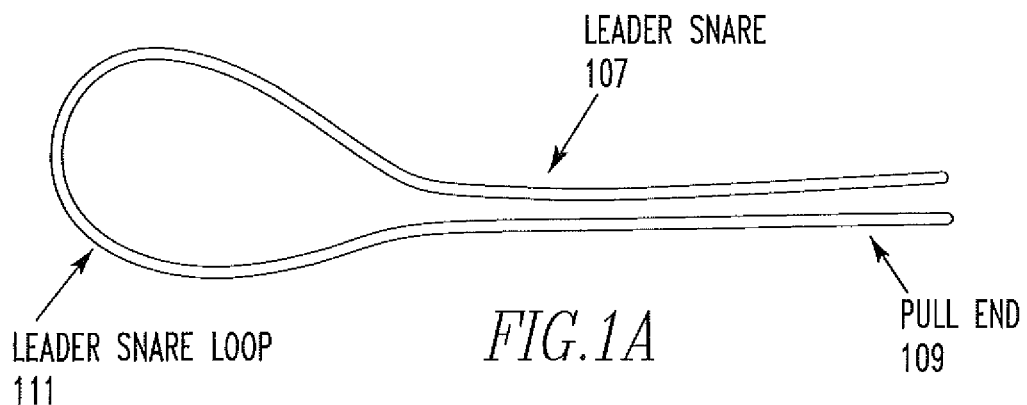
FIGS. 1A-1D show variations of pre-tied suture knots (FIGS. 1C and 1D) including a leader snare (FIG. 1A) that passes through one or more loops of a knot body (FIGS. 1B, 1C and 1D).

Described herein are sutures with pre-tied suture knots that are compatible for use in minimally invasive surgical techniques using a suture passer. The structure of different types of pre-tied knots are described herein, including variations that may result in different knots, variations formed of the suture material themselves, and variations formed of different material(s) that may be connected to the suture. In addition, methods of forming, placing and tying pre-tied knots are also described. Finally, examples of the use of a pre-tied knot to repair, anchor and otherwise fix tissue or tissue and implants (e.g., explants, implantable medical devices, and the like) are also provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

The pre-tied knots described herein may be used with any appropriate type of suture material, including any appropriate size, length and/or diameter of suture material. Examples of suture materials may include: surgical-grade sutures such as catgut (plain, chromic), silk, polyglycolic acid, polylactic acid, polydioxanone, nylon, polypropylene, etc.

A pre-tied knot may refer to one or more knots formed in a length of suture, and may generally include both the knot body as well as a leader snare that is knotted to the length of suture by the knot body. The pre-tied knot may be formed exclusively of suture material, or it may include one or more additional materials, and/or it may modify the suture material, or it may be formed of non-suture materials (such as metals, alloys, etc.). The pre-tied knot (e.g., the knot body of the pre-tied knot) may be loose or taut, and may be movable along a portion of the length of a suture or it may be fixed relative to a position on the length of suture. The knot body of the pre-tied knot may be formed of the same material as the suture on which the pre-tied knot is located, or it may be formed of a different material. The knot body may be fixed or moveable along the length of the suture from where it is positioned. The knot-body may also be tightenable. In some variations the knot body is formed at the end of the length of suture from the end of the suture material.

Structure of a Pre-Tied Knot

In general, a pre-tied suture knot as described herein may include a knot body region and a leader snare that passes through the knot body. The knot body ties the leader snare to the length of suture. In some variations the pre-tied knot is configured to tie together a first length of suture to second length of suture. The first and second lengths of suture may be on the same suture (e.g., forming a loop of suture) or they may be from different sutures.

As mentioned, any appropriate suture may be used with the pre-tied knots described herein. Thus a length of suture may be formed of any appropriate material, and particularly linear materials compatible for surgical use. A suture may be referred to as a suture or a suture thread, suture length, suture wire, suture braid, or the like. The suture may be made from appropriate materials, including biological materials, such as catgut suture and silk and synthetic materials, including the polyglycolic acid, polylactic acid, and polydioxanone, nylon and polypropylene. Sutures may be coated (e.g., with antimicrobial substances, growth-promoting substances, or the like), and may come in any appropriate sizes or ranges of sized. For example a suture of diameter from less than 0.01 mm diameter to greater than 0.8 mm may be used to form the suture. The suture may be monofilament or multifilament (e.g., braided).

In some variations, the knot-body of the pre-tied suture typically may include one or more loops through which the leader snare, and ultimately one or more ends of the suture, is positioned. The loop or loops may be cinched, tighten, and/or closed around the leader snare and/or suture, as described in more detail below. The loop(s) of the knot body typically extends along a region of the length of the suture.

In some variations, the knot body may be configured as a suture trap that allows one-way movement of a length of suture through the suture trap.

In some variations the knot body is formed and/or positioned near one end, e.g., a first end, of the suture. Although generally the knot body may be formed from a portion of the length of the suture, in some variations the knot body is instead formed of a separate material that is not part of the suture length. In some variations the knot body is formed of a different length of suture material. In other variations the knot body is not formed of suture material, for example, the knot body may be formed as a trap, clasp, or the like that can be cinched down onto the suture and/or that allows the suture to be pulled through in only one direction, while preventing withdrawal (and loosening) of the suture from the knot body.

As mentioned, the knot body may be slideable along the length of the suture, or it may be relatively fixed along the length of the suture.

A leader snare typically includes a flexible elongate (e.g., linear) body that extend through the knot body. One end of the leader snare may include a snare region, which may be a loop, hook, clasp, or the like, for holding an end of the suture, and a pull end which may be used to draw the leader snare through the knot body after a portion (e.g., the end) of the suture is coupled to the leader snare. This end of the leader snare may be referred to as a loop region or bight region. Drawing the leader snare through the knot body by pulling on the pull end of the leader snare may result in pulling the end of the suture through the knot body, removing the leader snare, and allowing the knot body to form a knot with the knot body to knot the suture. Both ends of the suture may then be drawn to shorten the suture and knot it in the tissue, as illustrated below.

The leader snare may be formed of a separate material from the suture and/or knot body. However, in principle, the leader snare could be formed of one end (e.g., the first end) of the suture. In use, the leader snare is configured to be pulled through the knot body after one end of the leader snare is coupled with a length (e.g., the second end region) of the suture. Thus, the leader snare may be held within one or more loops of the knot body. The leader snare may be loosely held, e.g., without tightening the loop(s) of the knot body to tightly over the leader snare. In some variations the leader snare comprises a material that reduces the friction between the leader snare and the suture material. For example, the leader snare may be coated with a "slippery" material (e.g., wax, polymeric coatings, etc.). In some variation the leader snare may have a tapered width so that it can be readily drawn out in one direction (e.g., towards the first end of the suture) by pulling on the pull end. For example the length of the leader snare body held within the loop(s) of the knot body may have a larger diameter at the proximal end (closest to the pull end) that tapers towards the opposite end (the coupling end of the leader snare, e.g., the loop end. In some variations the diameter of the leader snare may be greater than the diameter of the suture. For example, the leader snare may be formed of a suture material that has a larger (e.g., 1.5×, 2×, 3×, etc.) diameter than the diameter of the suture and/or the knot body. This may allow the end of the suture that is pulled through the knot body by the leader snare to be readily slid through the knot body to tighten the suture before knotting it.

As mentioned, the leader snare may be formed of any appropriate material. In some variations, the leader snare is formed of a flexible material. The leader snare may be completely or partially flexible. For example, the leader snare may be formed of a suture material that is identical or similar to the material forming the suture and/or knot body. In some variations, the leader snare is relatively incompressible. For example, at least a portion of the leader snare may be formed of a relatively non-compressible material, including plastics (e.g., polymeric materials). Preventing compression of the body region of the leader snare may help keep the knot body open even when pulling on the ends of the suture to pull the suture through the tissue (e.g., pulling on the first end of the suture proximal to the knot body).

In some variations, the pre-tied knot may include a second pull-string that is passed through the knot body, completely or in part. Removing this pull-string (which may be a string, wire, rod, etc.) may loosen the knot body around the leader snare, and allow it to be more readily drawn through the knot body, and may also allow the end of the suture pulled through the knot body to be more easily slid through the knot body (allowing it to be more easily tightened over the tissue).

The leader snare includes a suture coupling end which may secure a portion (e.g., the second or distal end) of the suture so that it can be pulled through the knot body. As illustrated herein, in some variations the leader snare includes a bight or loop region through which the suture can be placed. Any appropriate coupling means may be used, including non-loop configurations, such as hooks, graspers (e.g., clamps), adhesives, or the like. A bight may refer to any curved section and/or loop in a linear material (e.g., string, wire, rope, fiber, braid, suture, etc.).

Figure 2A:
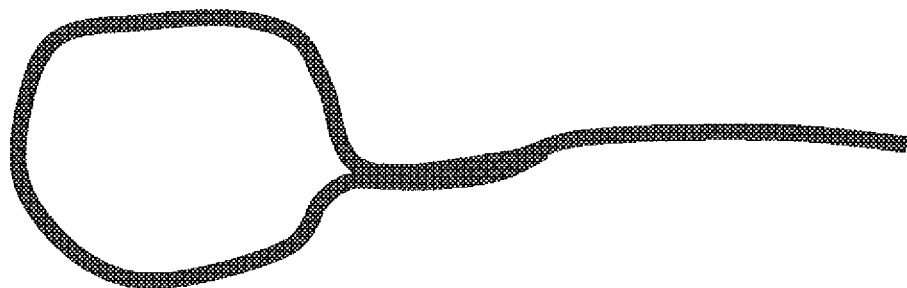
FIGS. 2A and 2B show two variations of leader snares similar to that shown in FIG. 1A.
Figure 2B:
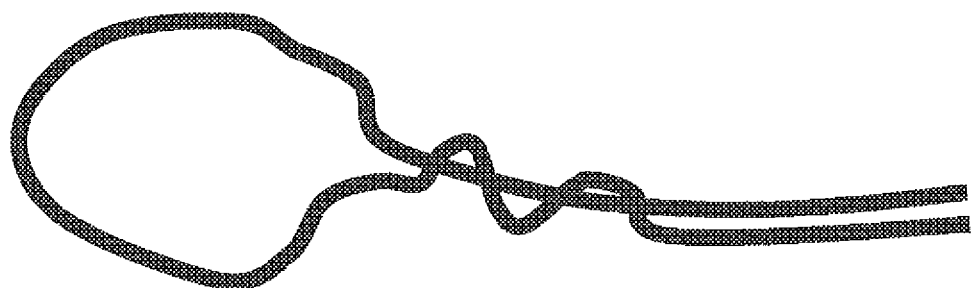

FIGS. 1A, 2A and 2B illustrate variations of leader snares that may be used with the pre-tied knots described herein. For example, in FIG. 1A, the leader snare includes a distal loop region 111 that is formed from the suture material forming the leader snare 107. The loop is formed by doubling the suture material over on itself. The end of the leader snare opposite the loop is the pull end 109, and consists of the two ends of the suture. In some variations (e.g., FIG. 2A) the pull end is only a single end. For example, the loop of the leader snare may be formed by securing the ends of the loop together leaving a single end region. In FIG. 2B, the suture forming the leader snare has been shaped into the loop region and the suture has been wrapped around itself; alternatively, the ends of the fiber forming the leader snare may be connected, woven or otherwise attached to each other.

Figure 1B:
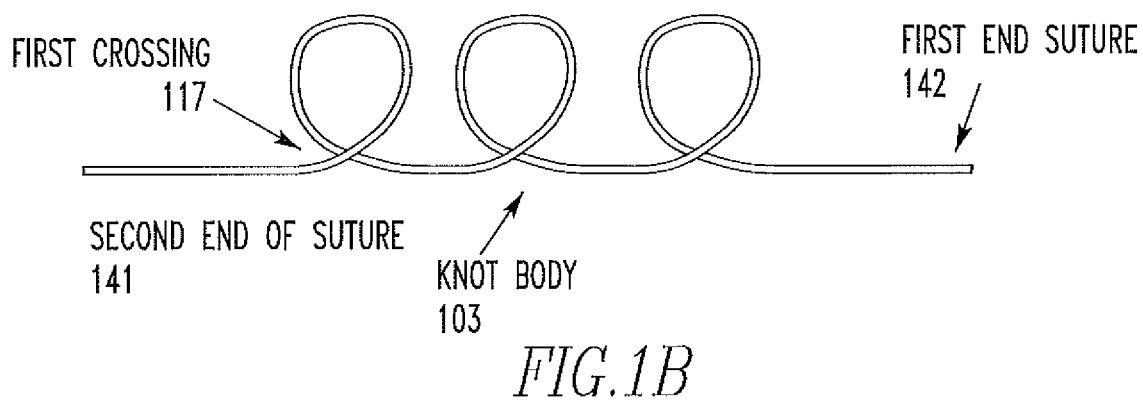
Figure 1C:
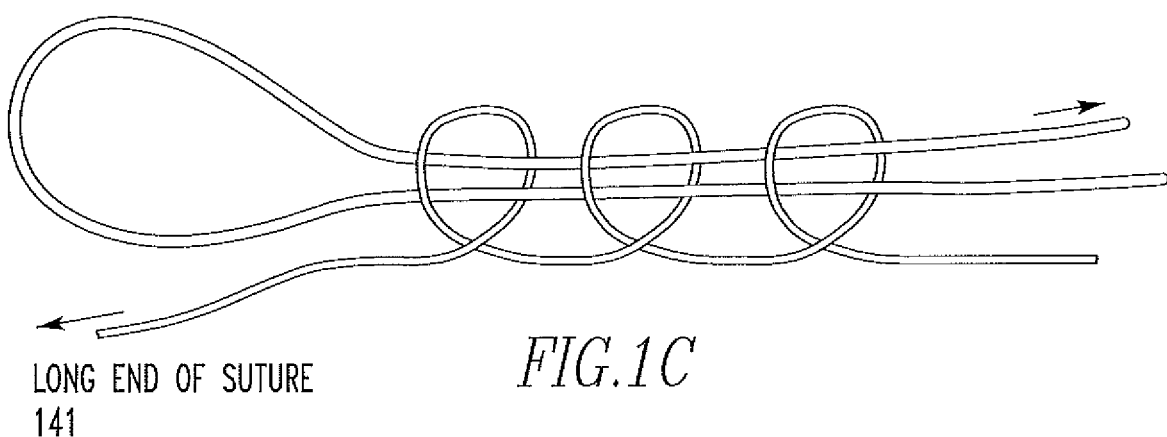

FIG. 1B shows one variation of a knot body that may be used as part of a pre-tied knot, as shown in FIG. 1C. In this example, the knot body 103 includes three loops, where each loop includes a single crossing 117. The loops are formed from the suture material near the first end of the suture 142. The leader snare 107 shown in FIG. 1A is positioned within the knot body 103 as shown in FIG. 1C, so that the leader snare loop 111 extends towards the long end of the suture (the second end 141) while the pull end of the leader snare extends proximally towards the first end of the suture 142.

Figure 1D:
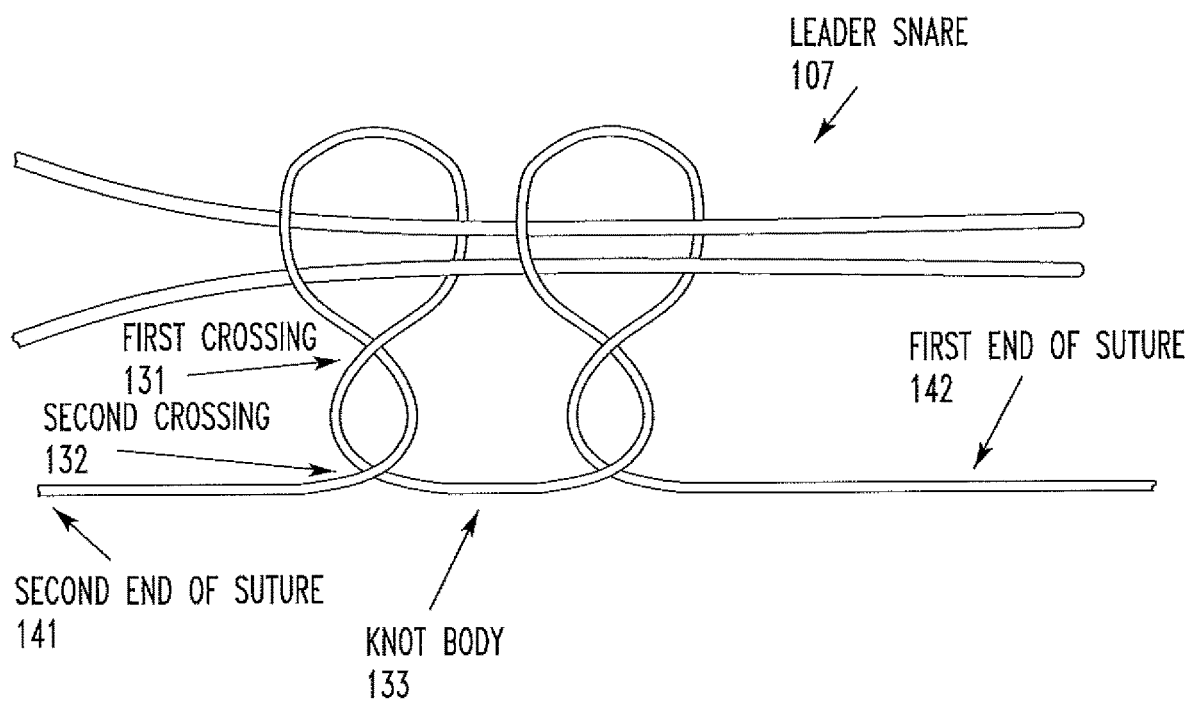

Another variation of a pre-tied knot is shown in FIG. 1D. In this example, the same leader snare 107 shown in FIG. 1A is illustrated within a knot body 133 formed from two loops (though more could be used), each loop formed to have two crossings 131, 132.

In some variations, the pull-string described above may be passed through the same loop as the leader snare, or it may be passed through a separate region of the knot body (such as the loop(s) formed between the first and second crossings 131, 132.

Figure 2C:
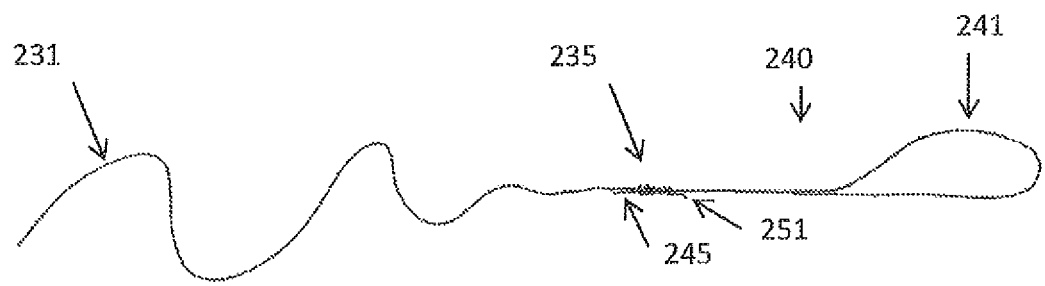
FIG. 2C shows another variation of a length of suture including a pre-tied knot formed of a leader snare similar to the one shown in FIG. 1A.
Figure 2D:
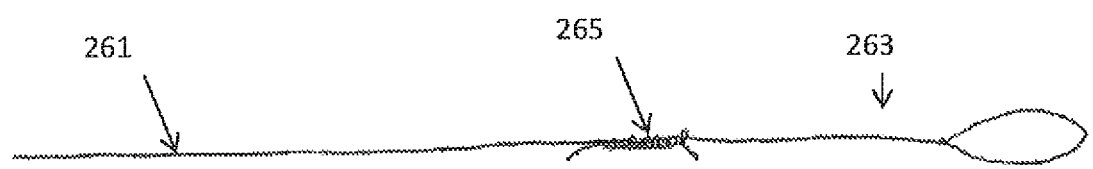
FIG. 2D shows another example of a length of suture including a pre-tied knot, where the pre-tied knot includes a leader snare similar to the one shown in FIG. 2A.
Figure 2E:
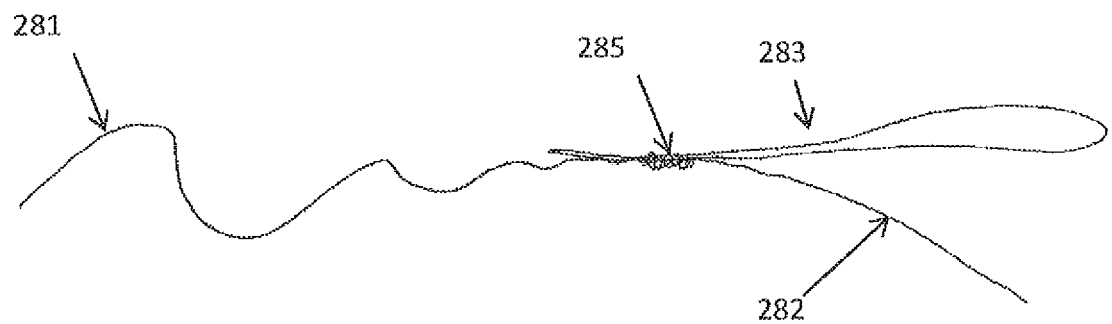
FIG. 2E shows another variation of a length of suture having a per-tied knot, wherein the pre-tied knot is located more towards the medial region of the length of suture than the distal or proximal end regions of the length of suture. Note that the direction of the bight region (to the left, or proximal end) and the direction of the tail of the leader snare may be reversed in any of the variations described herein.

FIGS. 2C-2E illustrate other variations of sutures having pre-tied knots. For example, in FIG. 2C, the length of suture 231 has a proximal and distal end, with the pre-tied knot body 235 formed at the proximal end region 251. A leader snare 240 similar to the leader snare of FIG. 1A, is knotted to the proximal end of the suture 231 by the pre-tied knot body 235, so that the bight region 241 of the leader snare extends proximally from the knot body and the tail (pull tail) 245 extends distally.

FIG. 2D shows another example of a length of suture 261 that has a pre-tied knot body near the proximal end of the length of suture. A leader snare 263, similar to the one shown in FIG. 2A, extends proximally and is tied to the suture by the pre-tied knot body 265. In this example, the leader snare has a loop formed at one end of the leader snare. In some variations the leader snare is a single (e.g., doubled-over) length of suture material forming a loop at one end, and the pull tail at the other end. In some variations the entire leader snare is a loop (closed loop) of material. In FIG. 2D, the tail of the leader snare extends distally and the loop/bight region extends proximally; however, in any of these variations this direction may be reversed, and the direction of the loop/bight may be distal while the tail is proximal.

In FIG. 2E, the pre-tied knot is located away from the proximal 282 and distal 283 ends of the length of suture, and is positioned more medially. In this example, the pre-tied knot body 285 ties the leader snare 832 to the region between the proximal 282 and distal 283 ends of the suture. Either, or both, ends of the suture may be passed through the bight region of the leader snare and pulled through the pre-tied knot body to knot the suture.

Methods of Forming, Positioning and Tying Pre-Tied Knot

As mentioned, a pre-tied knot may be formed at any region of a suture, and it may be slideable or fixed relative to the suture. The pre-tied knot is typically formed before inserting the device into the patient. The pre-tied knot may be made manually or automatically. The loops of the knot body may be formed over the leader snare by sequentially looping a length of suture over the leader snare and twisting the loop to form one or more crossings. In some variations a loop is formed by twisting a bight of suture from a length of suture and passing the leader snare through the loops; the knot body may be tightened slightly over the leader snare to hold it within the knot body.

In use, a suture having a pre-tied knot positioned at one end of the suture may be passed through tissue and an end of the suture may be pulled through the pre-tied knot by passing the end of the suture through the leader snare and pulling the tail or pull end of the leader snare to pull the entire leader snare though the knot body. The knot may be tightened. In some variations, the knot is tightened after pulling the end of the suture through the knot body by pulling one or both ends of the suture to tighten the loop. The knot body may also or alternatively be tightened down on the length of suture to complete the knot. Any loose ends of the suture can then be cut. This entire procedure may be performed minimally invasively (e.g., through a cannula and/or using an endoscope).

For example, FIGS. 3A-3G illustrate one variation of a method for repairing tissue and placing a pre-tied knot in a suture. In this example, the tissue being repaired is the knee meniscus, and the repair may be performed minimally invasively using a suture passer to pass the suture through the tissue, including positioning the pre-tied knot and using the pre-tied knot to secure the suture. Although many of the examples described herein are shown with respect to meniscus, these methods and apparatuses may be used to suture any appropriate tissue, and are not limited to meniscus.

Figure 3A:
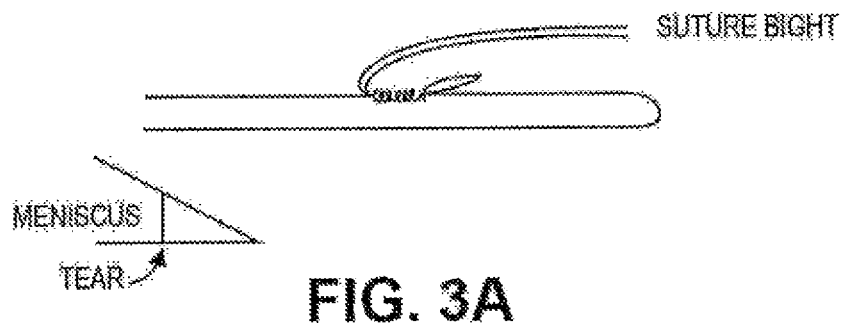
FIGS. 3A-3G illustrate one variation of a method for suturing tissue and knotting the suture with a pre-tied knot such as the pre-tied knot shown in FIG. 1C. In this example the tissue is a torn meniscus that is being repaired endoscopically to form a vertical loop repair, extending through the meniscus twice between the superior and inferior surfaces of the meniscus.
Figure 3B:
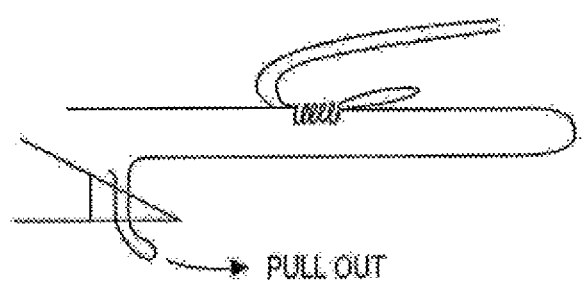
Figure 3C:
Figure 3D:
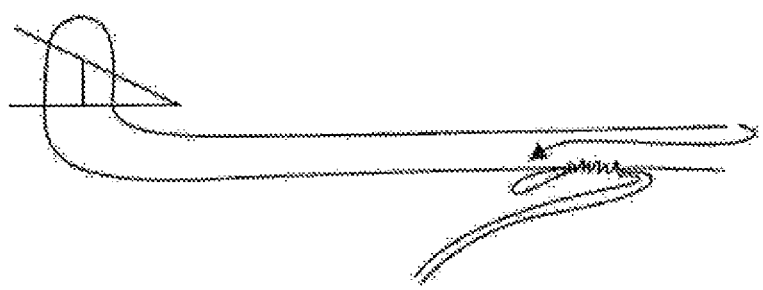

In FIG. 3A, a schematic view of a portion of a torn meniscus (shown in partial cross-section on the left) is shown. A suture including a pre-tied knot (including a leader snare, referred to as a "suture bight" in this example) is passed through the meniscus and around the tear. In FIG. 3B, the distal end of the suture is first passed through the more apical region of the meniscus from the superior to the inferior side of the meniscus, to the apical side of the tear. Thereafter, the proximal end of the suture is passed from the superior to the inferior side of the meniscus on the opposite side of the tear, as shown in FIG. 3C. In FIG. 3D, the proximal end of the suture, including the pre-tied knot, is then drawn through the meniscus tissue.

As discussed briefly above, the pre-tied knots described herein in some variations are sufficiently flexible and low-profile that they may be passed through the tissue without substantially damaging the tissue. In FIG. 3D, the pre-tied knot (including the knot body and the leader snare) is pulled through the tissue by the suture passer, which may include a tissue penetrator that can pull the suture through the tissue. Once in position, the distal end of the suture may be passed through the large loop of the leader snare, as shown in FIG.

Figure 3E:
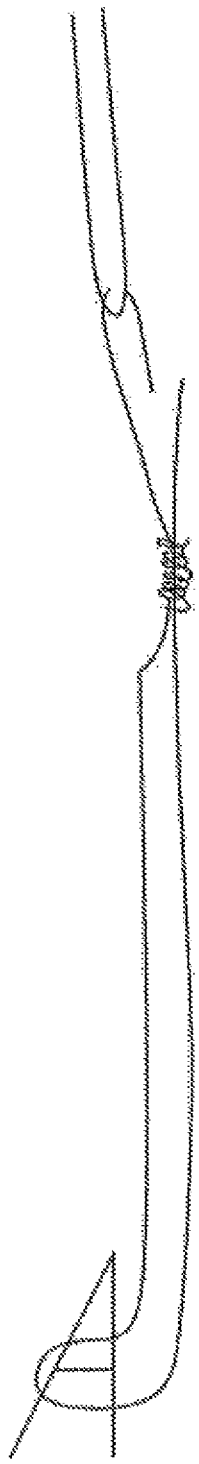
Figure 3F:
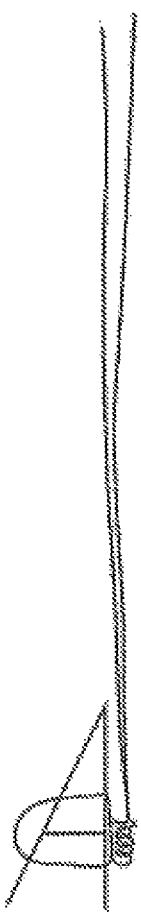
Figure 3G:

3D. The pull end of the leader snare may then be drawn proximally, as shown in FIG. 3E, which results in the distal end of the suture passing through the knot body of the pre-tied knot. In FIG. 3F the pre-tied knot is moved towards the tissue by pulling the distal end of the suture, constricting the suture loop formed after pulling the distal end through the knot body around the tissue. Once the tissue is secured, the knot body may be tightened around the suture to tighten the knot, for example by pulling the proximal end of the suture. As shown in FIG. 3G, the ends of the suture may then be cut, leaving the tissue sutured.

Figure 4A:
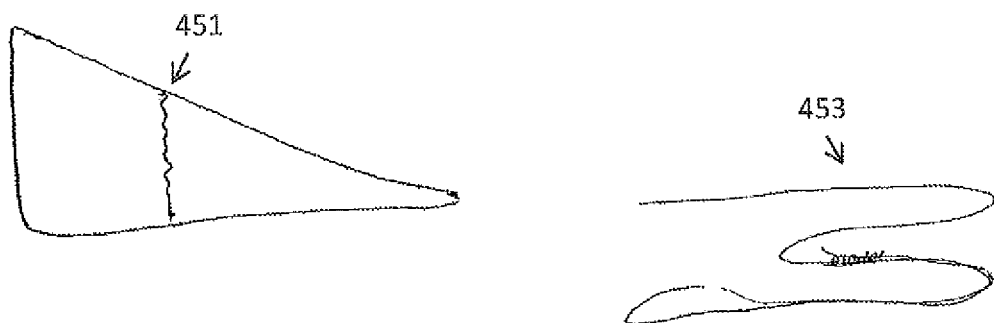
FIGS. 4A-4H show another variation of a method for arthroscopically repairing a torn meniscus by forming a loop of suture around the tear.
Figure 4B:
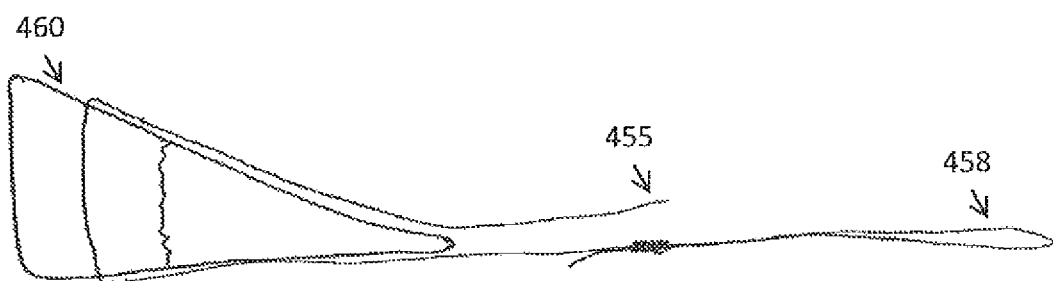
Figure 4C:
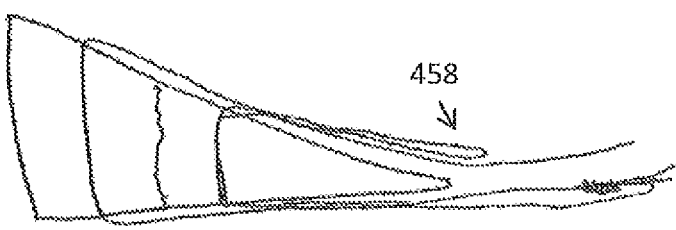

FIGS. 4A-4H illustrate another variation of a method for repairing (arthroscopically) a torn meniscus by forming a loop of suture around the tear. In this example a suture passer (as described in more detail below) may be used to pass the suture through the meniscus of the knee during an arthroscopic procedure. FIG. 4A illustrates the length of suture having a pre-tied knot (similar to that shown in FIG. 2C) that may be used to repair the torn meniscus 451. As shown in FIG. 4B, the distal end of the suture 455 may be initially passed through the meniscus (e.g., from the inferior side of the meniscus to the superior side 460 of the meniscus) on one side of the tear, as shown. In this example, the distal end of the suture may exit the knee region, so that the distal end of the suture extends from an opening in the knee (or out of a cannula, if one is used). The loop region (bight region) of the leader snare may be loaded in to the suture passer (not shown) and passed through the meniscus on the opposite side of the tear, as shown in FIG. 4C. In this example, the bight region is passed from the inferior to the superior surfaces of the meniscus. All or a portion of the bight region may also extend out of the knee (e.g., out of the access opening made into the knee) or it may remain within the tissue. Similarly, a portion of the suture, including the knot body and/or the tail of the leader snare, may extend from the knee so that it can be easily manipulated. Alternatively, it may be within the tissue and manipulated using one or more arthroscopic tools.

Figure 4D:
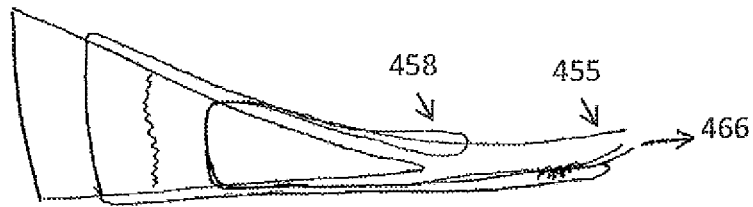
Figure 4E:
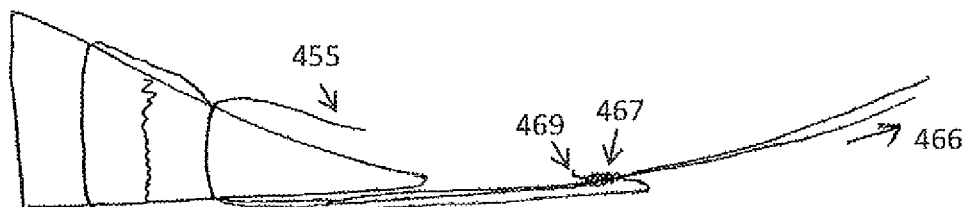
Figure 4F:
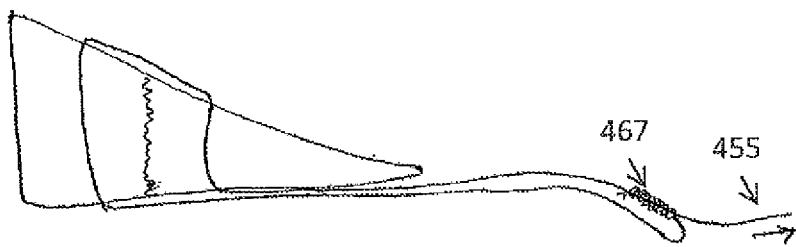
Figure 4G:
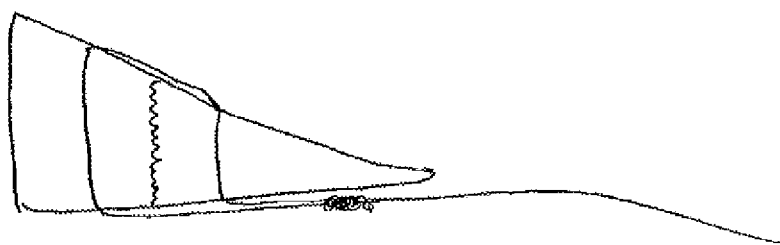
Figure 4H:
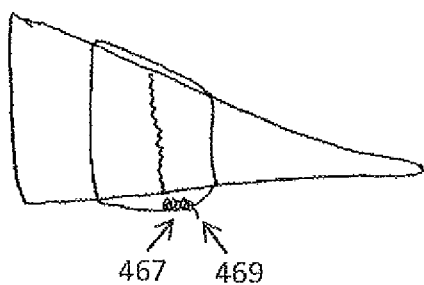

The distal end of the suture 455 may then be passed through the loop of the bight region 458, as shown in FIG. 4D, and thereafter the tail of the leader snare may then be pulled (proximally in this example, as shown by arrow 466) to draw the bight region and the captured distal end of the suture back through the meniscus in the same path already taken by the bight region of the leader snare, as shown in FIG. 4E. Finally, in FIG. 4F, the entire snare leader has been removed, pulling the distal end of the suture through the pre-tied knot body. The distal end of the suture 455 then extends proximally from the knot body in this example. The knot loop formed my then be cinched around the meniscus as shown in FIGS. 4G and 4H. In this example, the loop is cinched by pulling either (or both) puling on the distal end of the suture 455 and/or pushing on the knot body 467. Once cinched, the pre-tied knot body may also be tightened. For example, one end 469 of the pre-tied knot body may be pulled to tighten the pre-tied knot body. The loose ends of the suture may be cut off, to leave the knot body on the inferior surface of the meniscus, with the loop of suture extending from the superior to the inferior surfaces and back, surrounding the torn region.

Figure 5A:
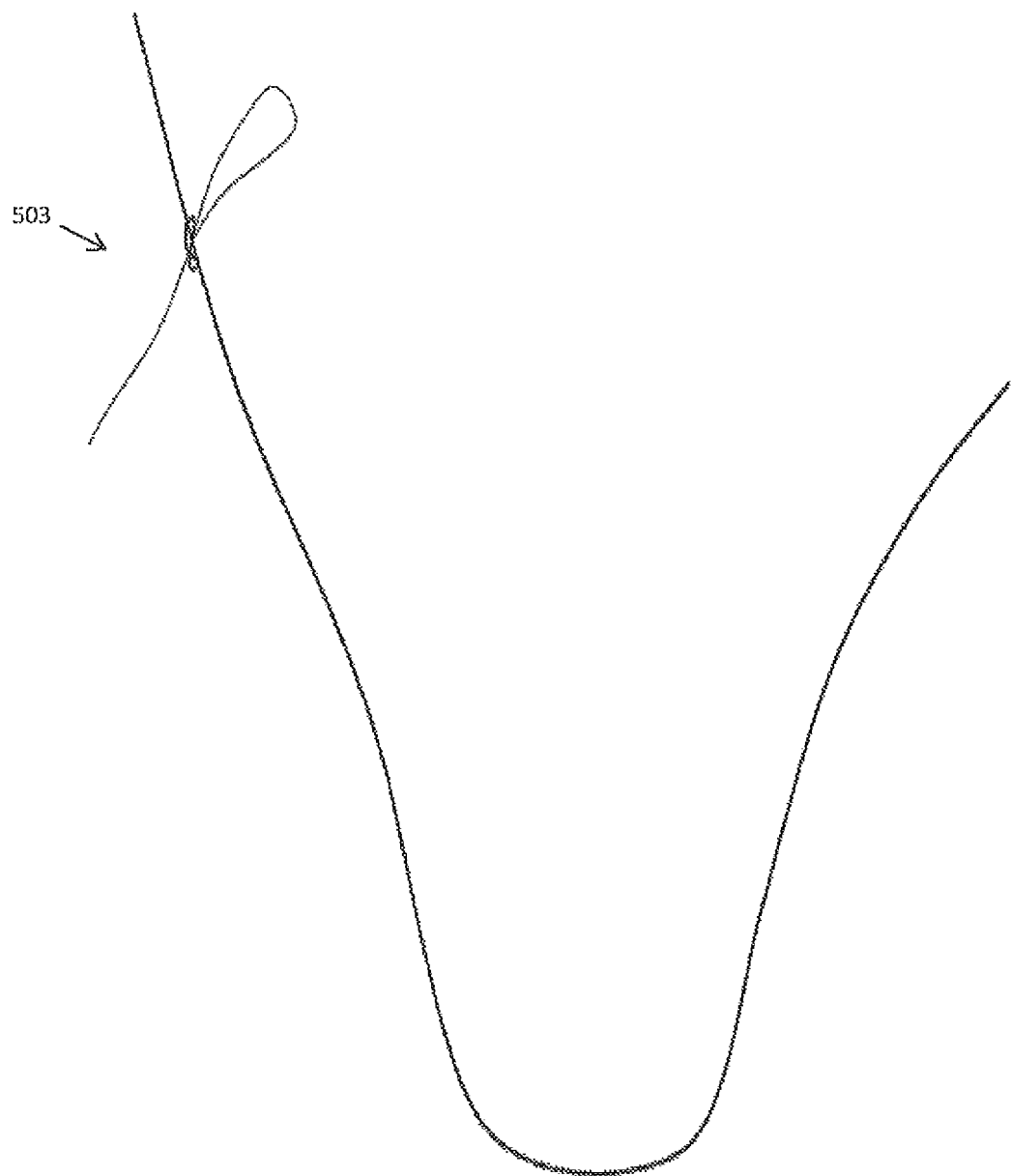

Another example of a pre-tied suture is shown in FIG. 5A. In this example a pre-tied sliding knot is positioned around a pull string 503 so that the opposite end of the suture can be easily pulled through the pre-tied knot. One or both suture strands of the suture can be passed through or around tissue. As mentioned above, the pre-tied knot and pull string can together travel through the tunnel made by the tissue penetrator.

Figure 5B:
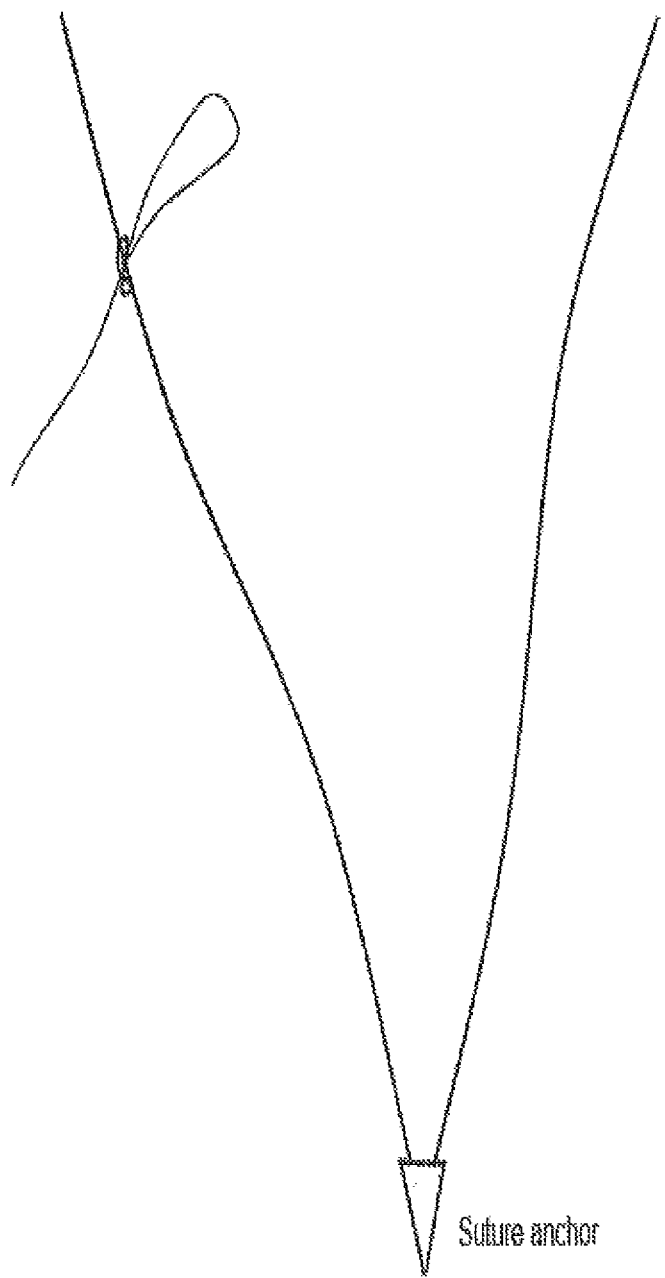

In some variations, the pre-tied knot is used with an anchor, as shown in FIG. 5B. In this example a suture anchor includes a length of suture extending from it, and a pre-tied knot is positioned at the proximal end of one length of suture, as shown.

Figure 5C:
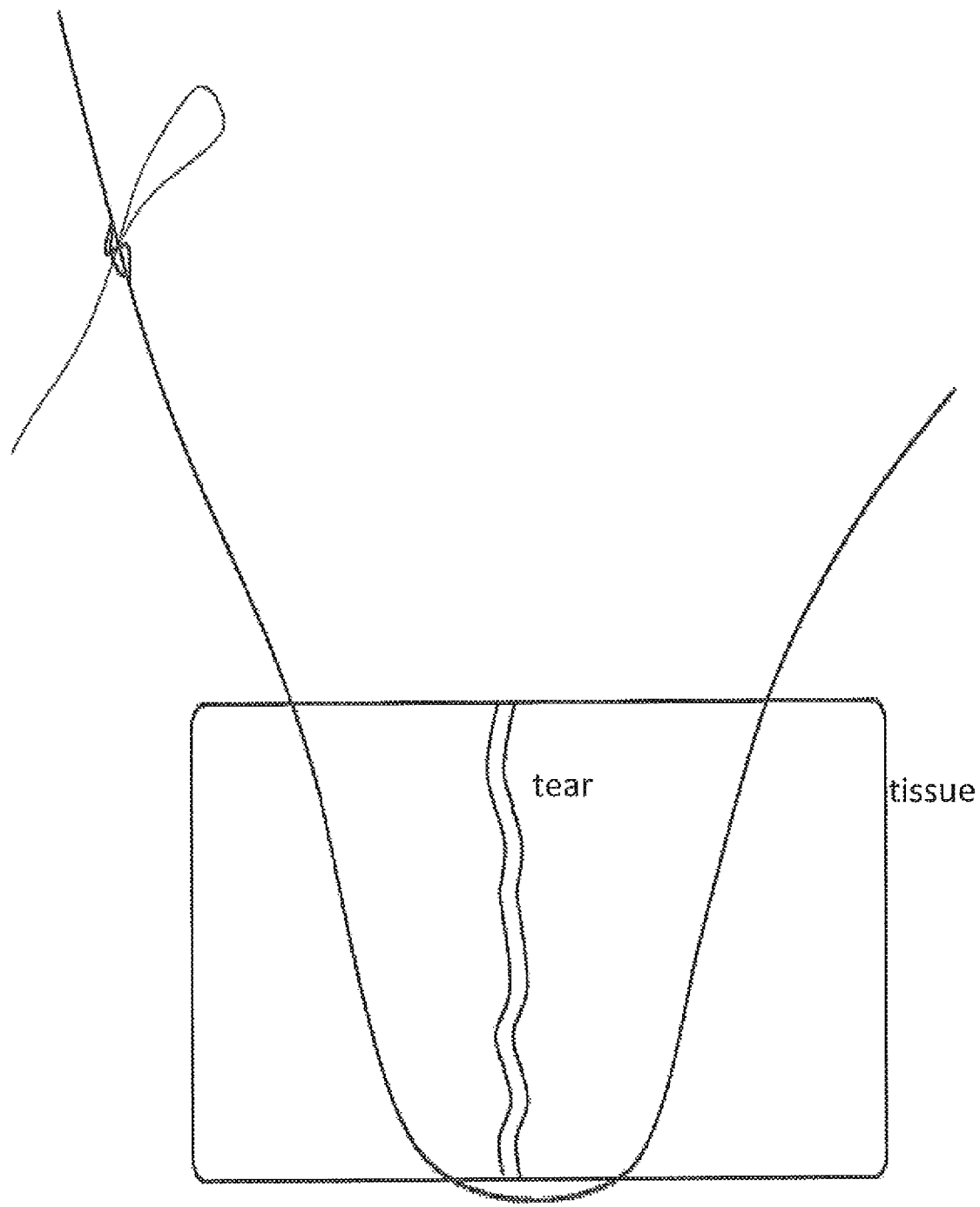
Figure 5D:
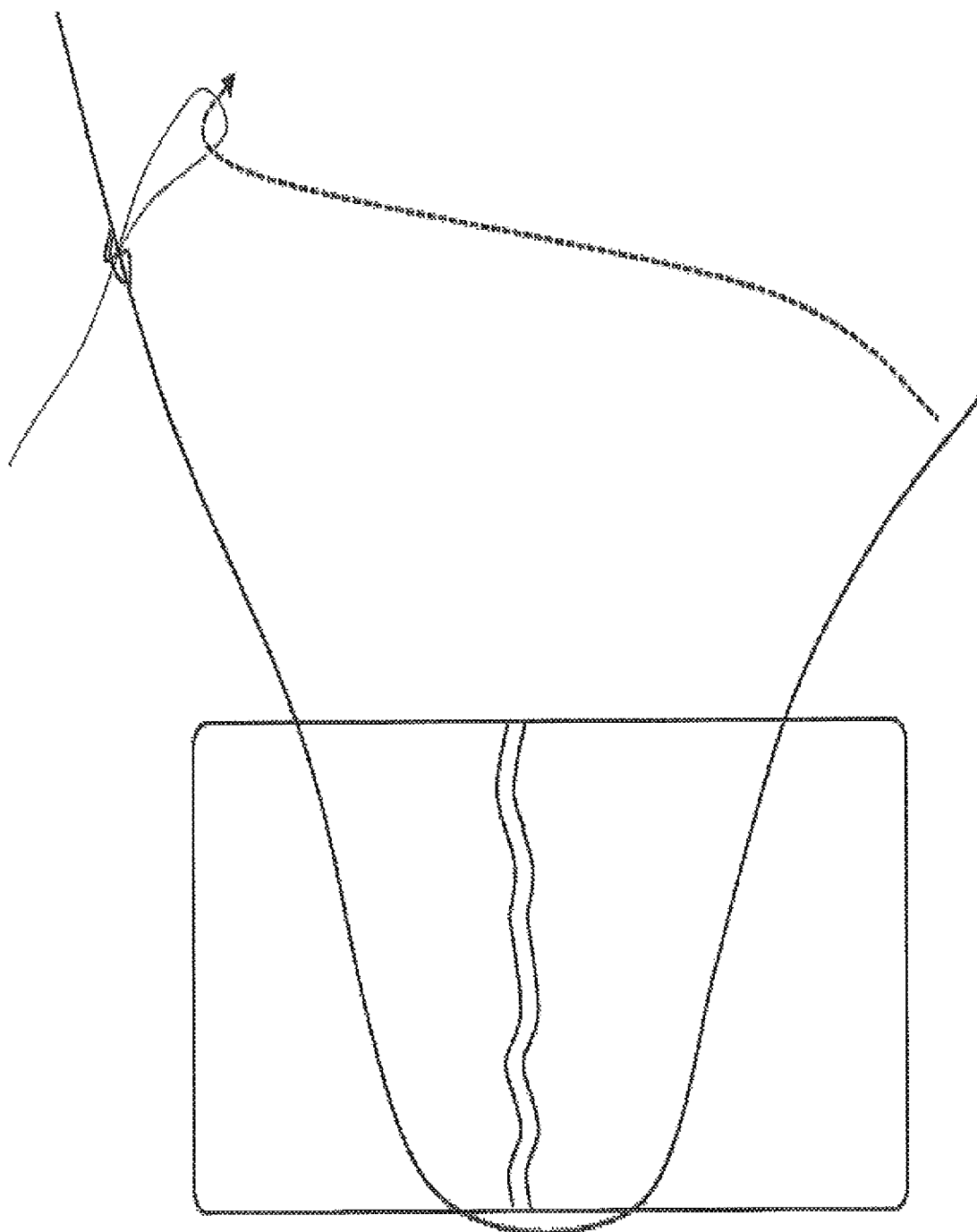
Figure 5E:
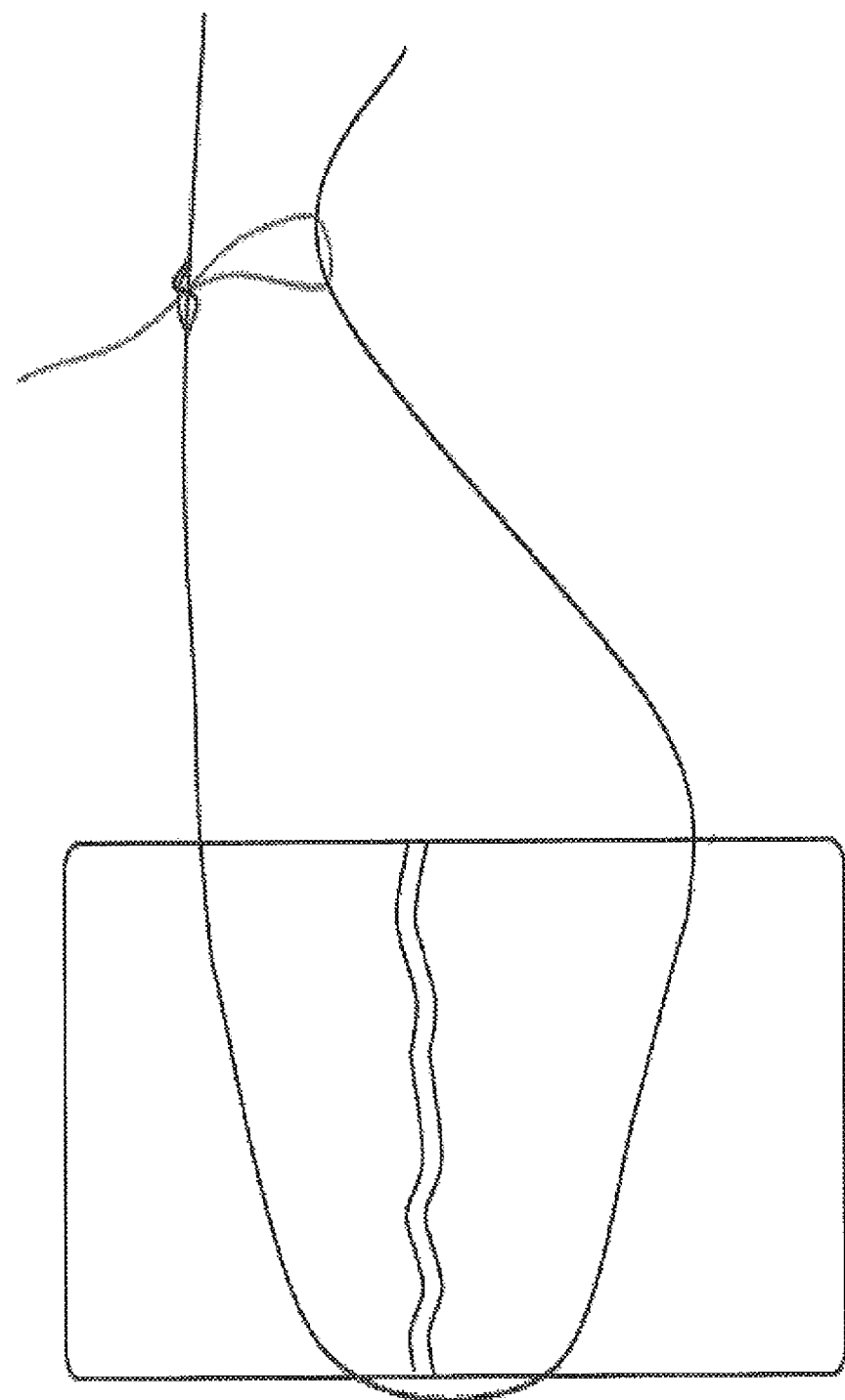
Figure 5F:
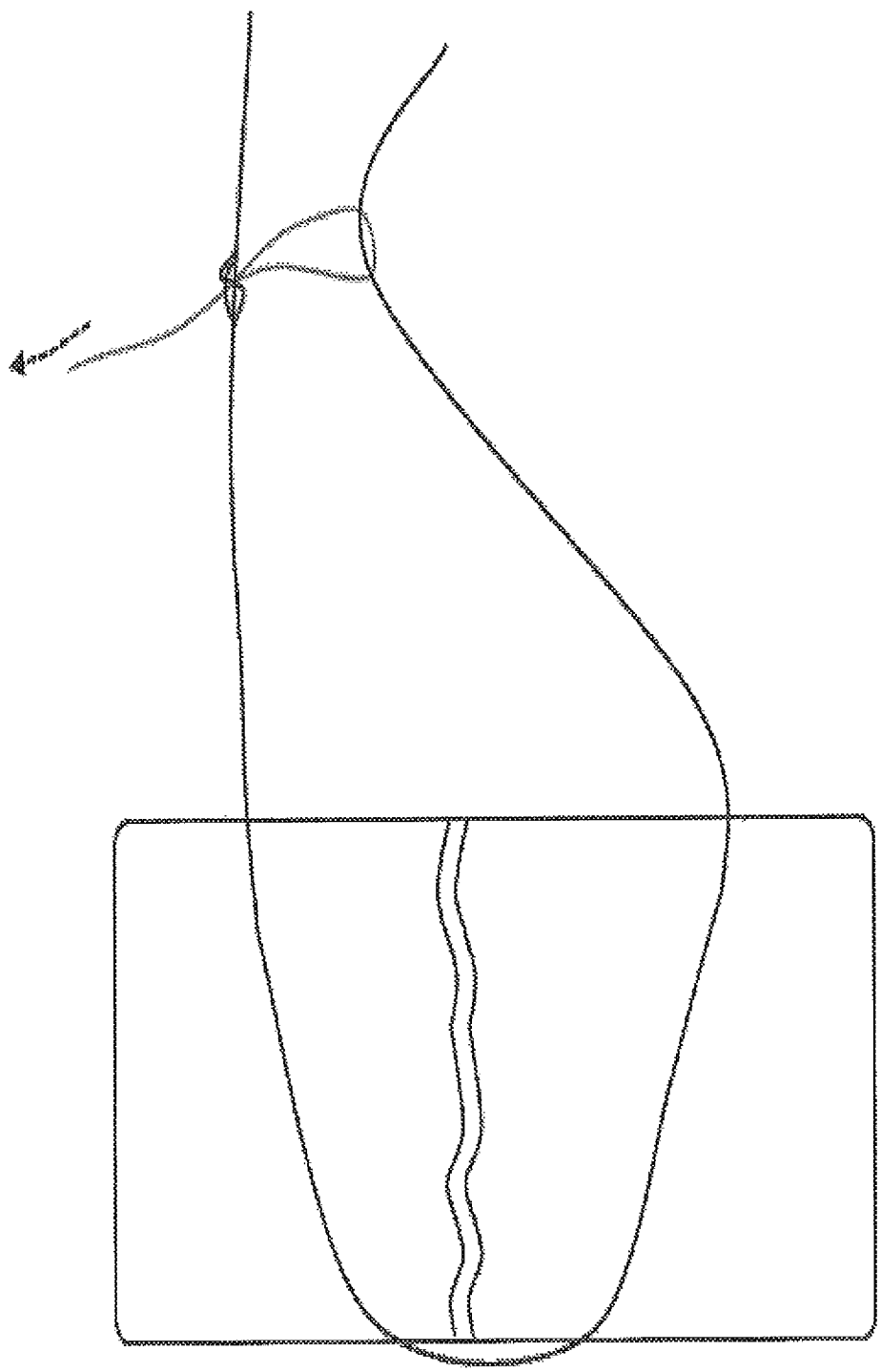
Figure 5G:
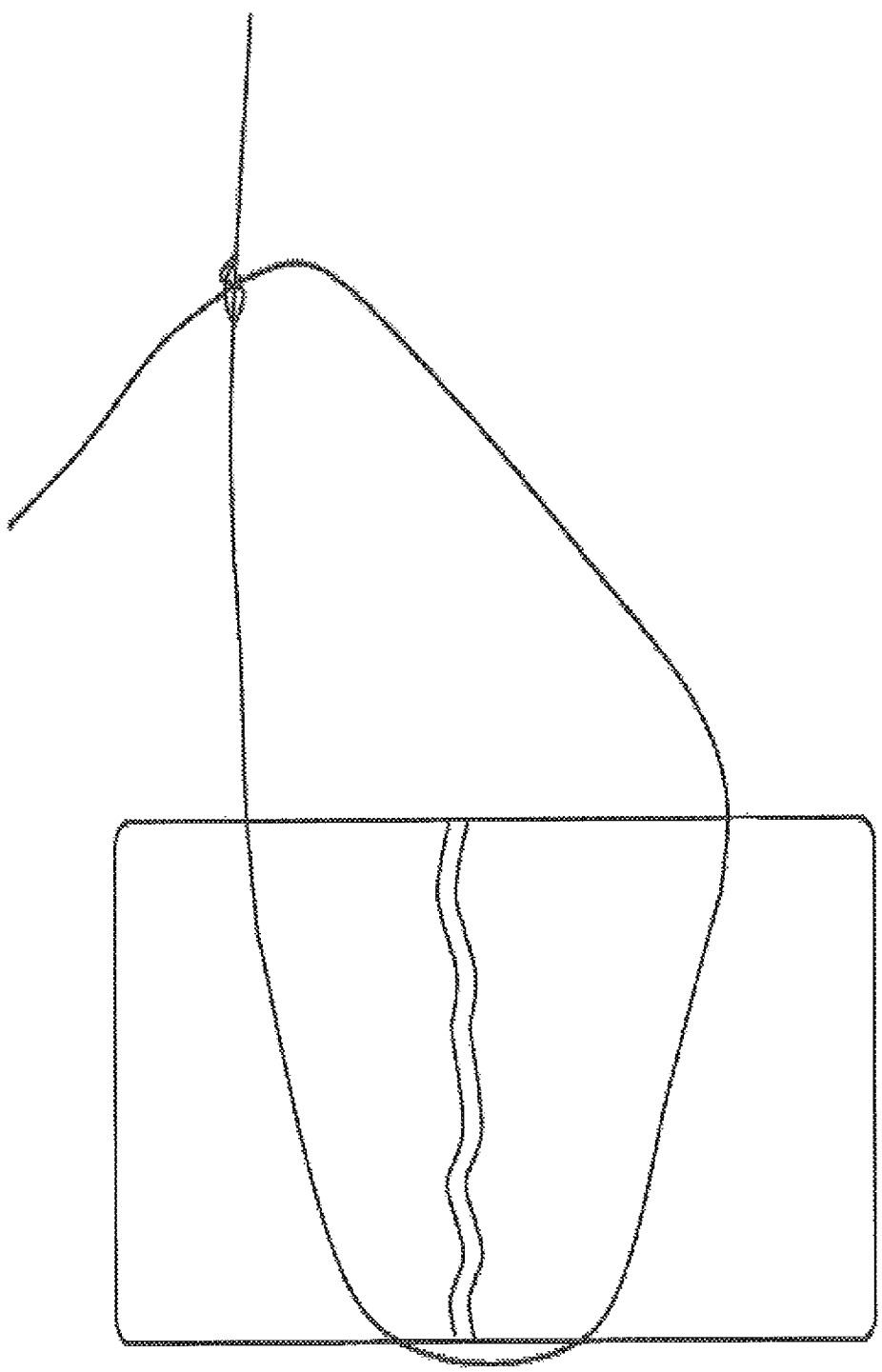
Figure 5H:
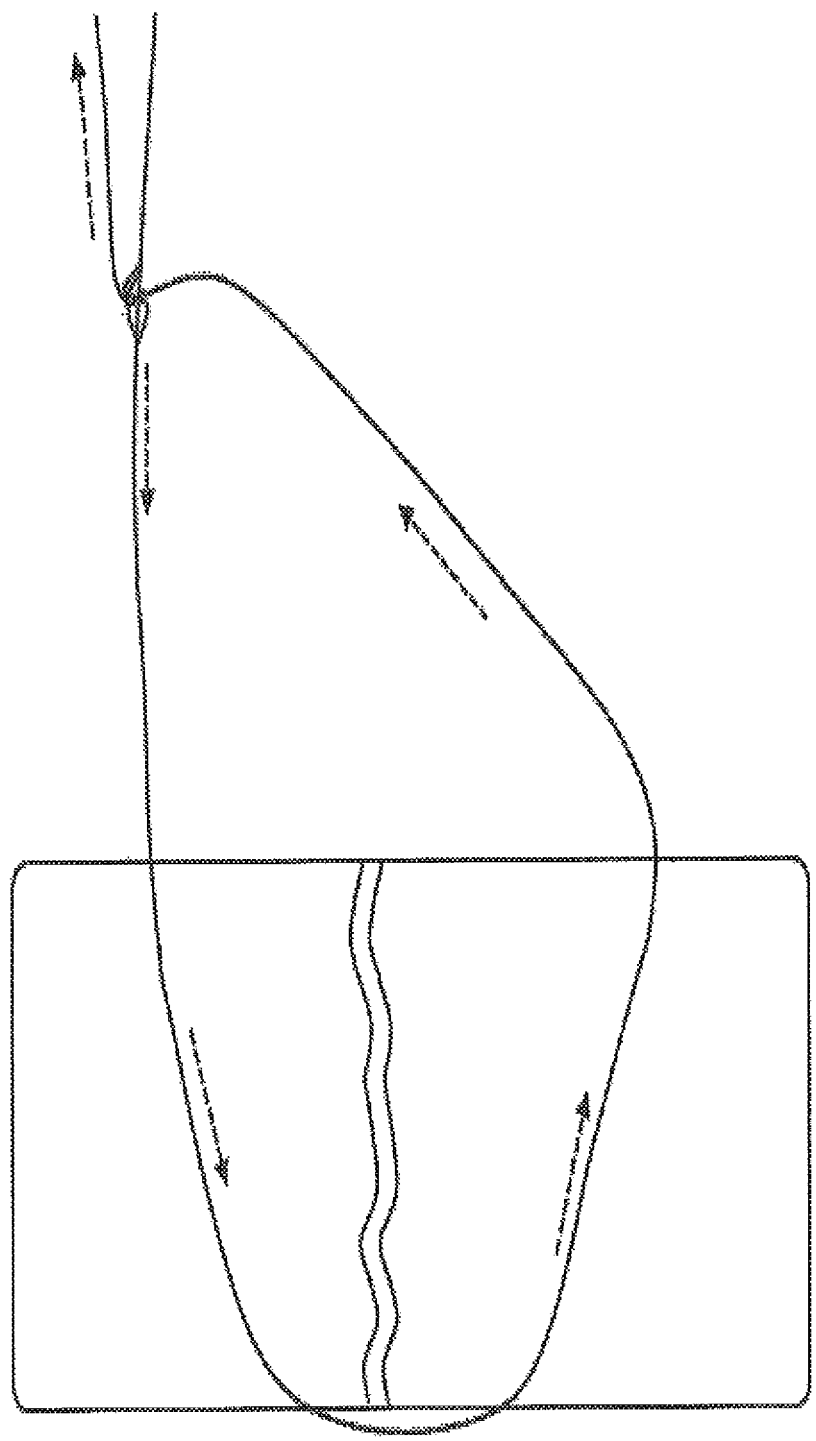

FIG. 5C illustrates one method of using a pre-tied knot to secure tissue. In this example, a suture including a pre-tied knot at one end has been passed through a region of tissue (around a tear in the tissue). As shown in FIGS. 5D-5E, the end of the suture opposite from the pre-tied knot may be drawn through the loop of the leader snare. In FIG. 5F, the pull end of the leader snare may then be pulled (arrow) to draw the end of the suture through the knot body, as shown, until the suture has been completely pulled through the knot body, and the leader snare removed from the suture, as shown in FIG. 5G. In FIG. 5H, the arrows indicate that the suture may be cinched down onto the tissue by pulling on the end of the suture that has been pulled through the knot body, as shown in FIG. 5I, resulting in jointing the torn tissue. The tissue may be secured with whatever tightness is desired. The knot may be tightened by pulling on the opposite end of the suture as mentioned, above, and the loose suture ends may be cut off. This entire procedure may be performed percutaneously.

Figure 5J:
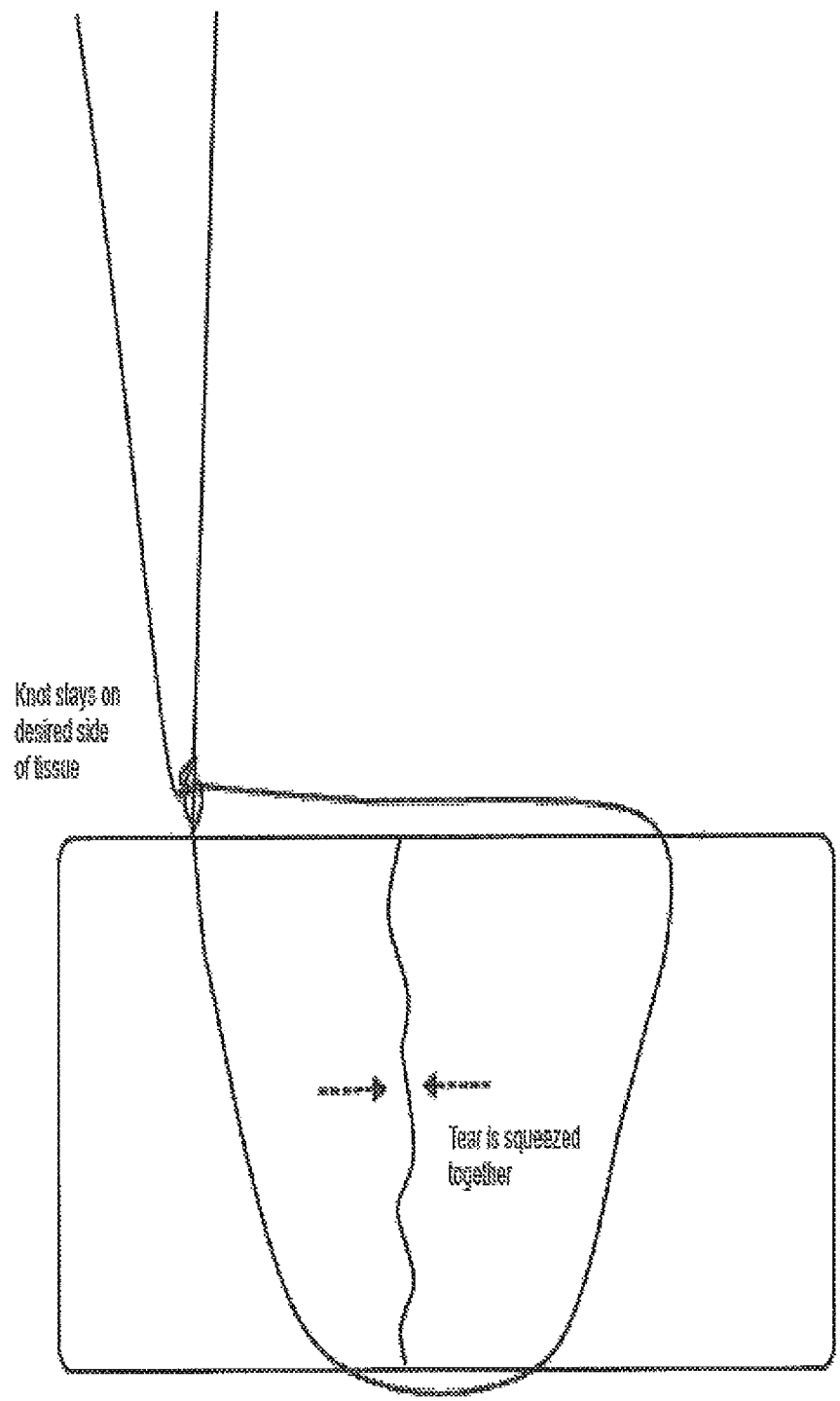
Figure 5K:
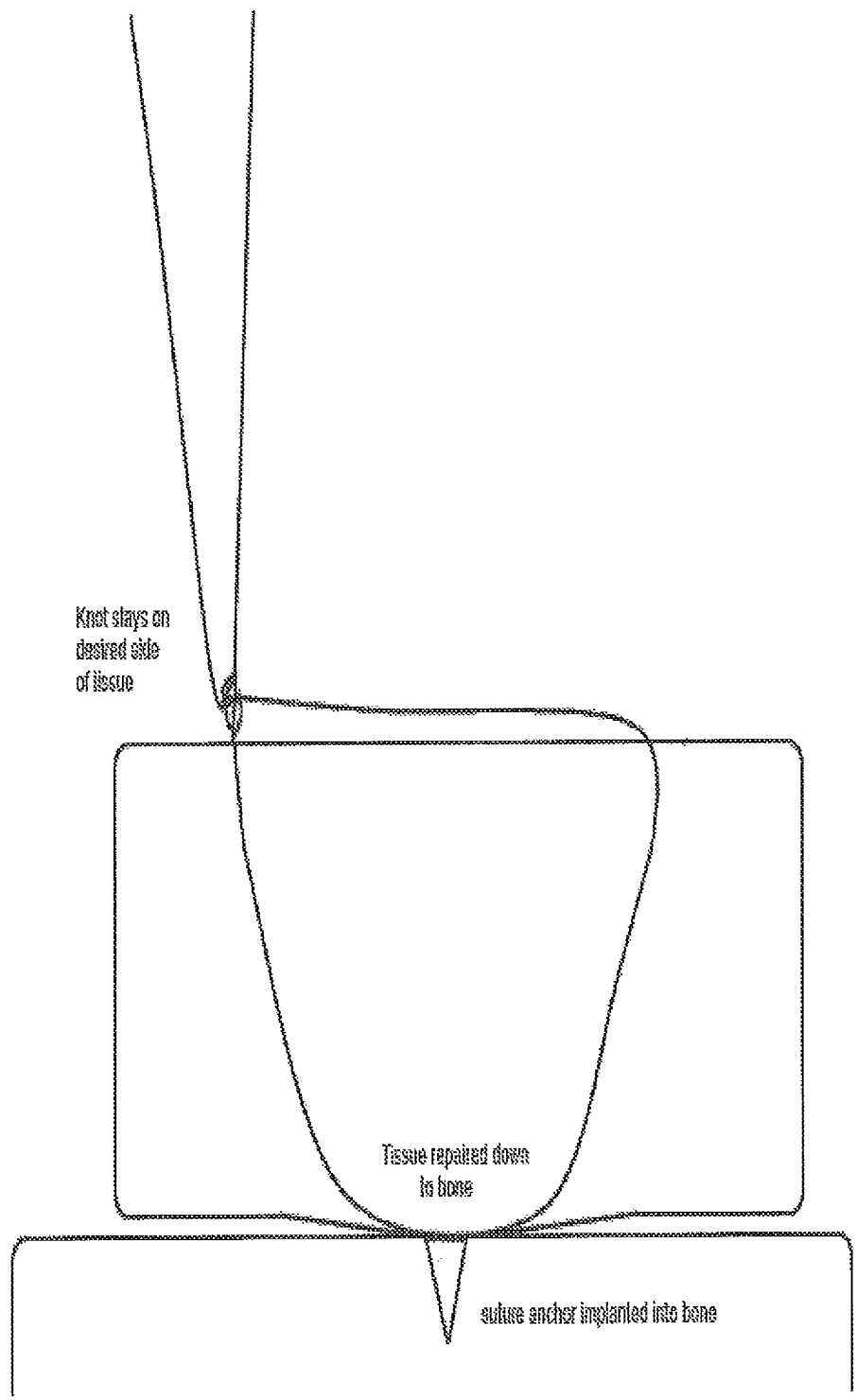

FIG. 5K shows a similar variation in which the suture is connected to an anchor that has been secured to the bone.

The examples shown above include pre-tied knots formed by looping a portion of a length of suture around itself one or more times to form the knot body which can be tightened over a leader snare and then used to secure a second region or length of suture through the knot body by cinching the knot body. In some variations the knot body forming a pre-tied knot is not formed (or not just formed) of a loop of suture length, but includes a suture trap region which permits only one-way movement of a length of suture through the knot body (e.g., suture trap).

Figure 6A:
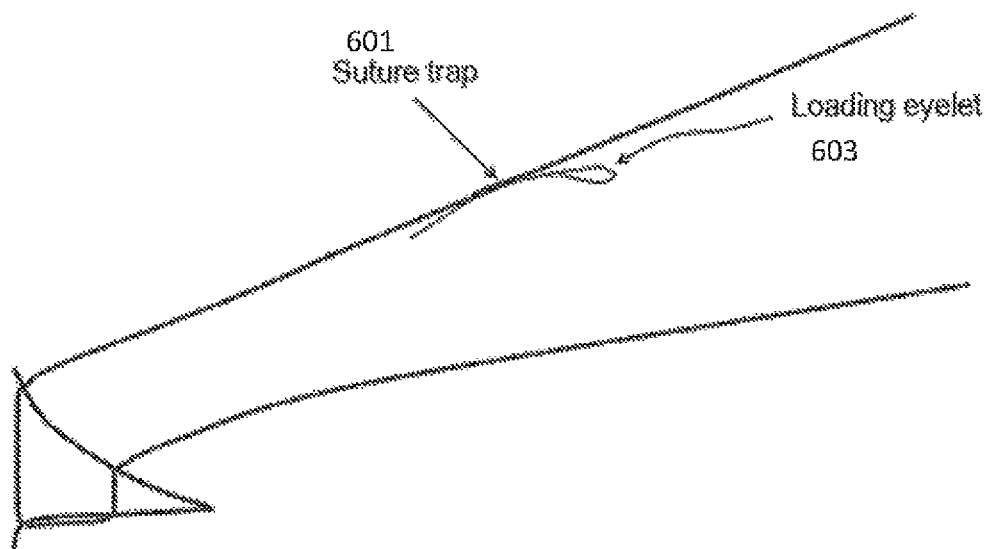
FIGS. 6A-6I illustrates another variation of a method for suturing tissue in which the pre-tied knot region is configured as a suture trap including a leader snare.

FIG. 6A illustrates one variation in which a knot body is formed of a suture trap that allows one-way passing (sliding) of a suture length. In this example, the suture trap 601 is coupled to the suture length and a leader snare 603 (which may also be referred to as a loading eyelet). The suture trap may be formed into the body of the suture, or it may be secured over or in the suture material. For example, the suture material may include a central lumen that may be opened at least partially to form a one-way channel for passage of a leader snare and/or suture length.

A one-way channel for a length of suture may be formed by including angled fibers, filaments, barbs, etc. within the channel that engage a suture to prevent its motion only when the suture is passing in a second direction; as the suture passes in a first direction the suture. For example, the suture trap may include internal barbs, cleats, rubber, braid, or other interference fit modifications that engage with a suture in a first direction, so that when suture is within, it cannot easily come out.

As illustrated above, a suture trap does not necessarily have to be a one-way channel for a suture length, but may be a constrictable channel that prevents withdrawal of a suture within the channel when under tension, but not when relaxed, similar to a woven finger-trap or finger-puzzle design. For example, a suture trap may be a modified section of a suture that acts as a 'finger trap' that constricts over a length of suture when under tension. The example shown above in FIGS. 3A-5K show variations such as this, in which the knot body is at least partially constricted around the leader snare.

As mentioned above a leader snare may be formed of a fine nitinol wire with a loop on the end or any string material.

Figure 6B:
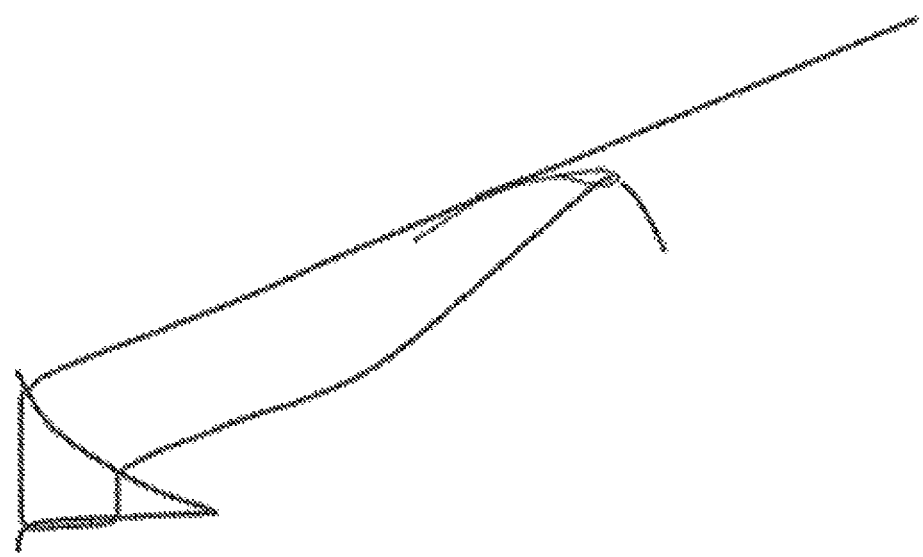
Figure 6C:
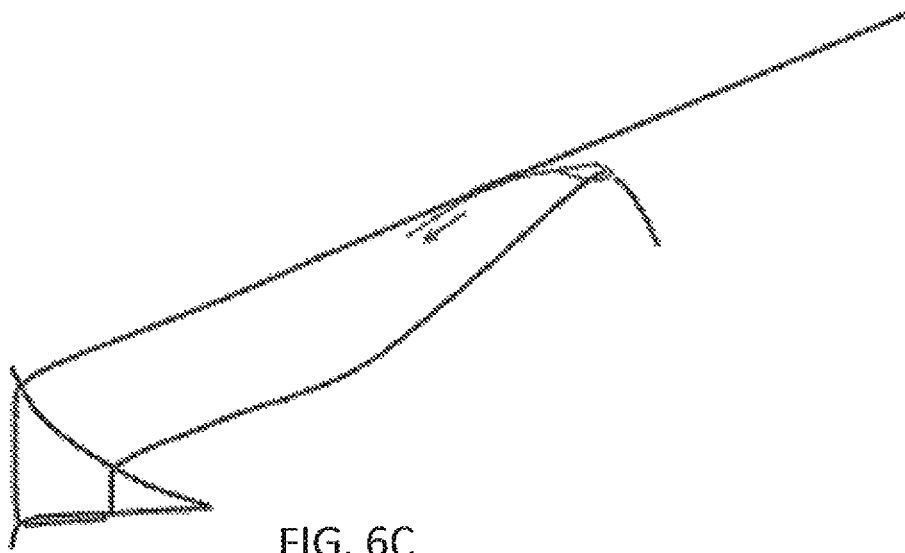
Figure 6D:
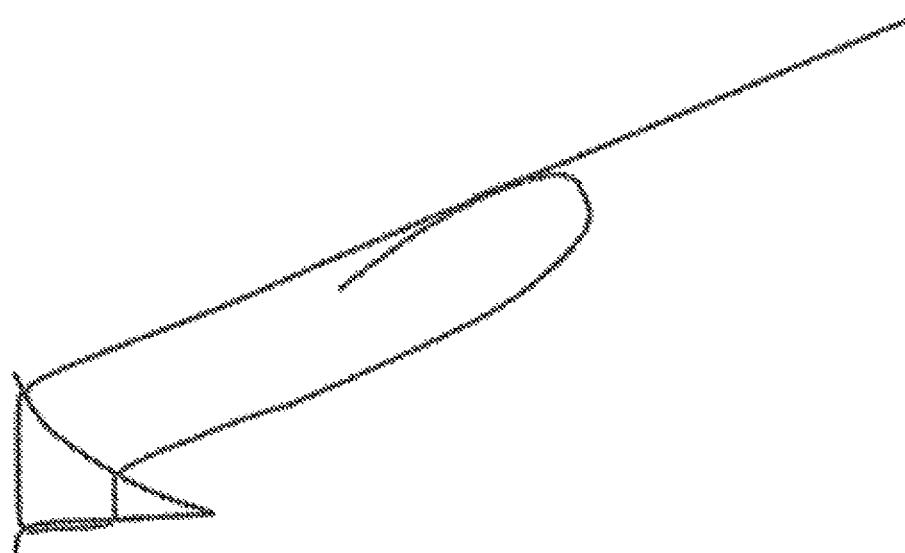

In FIG. 6A, the suture 600 includes a suture trap 601 connected to the suture. The suture body forms an enlarged region on the length of the suture, and a leader snare 603 passes through the suture trap. In some variations, the suture trap is formed from the suture length. For example, the suture length may be a woven material, and the suture trap (e.g., knot body) may be a passage into the woven body of the suture, along a length of a lumen within the woven body, and back out of the woven body. Once the suture has been passed through the tissue, as already shown in FIG. 6A, a second length of suture, in this case an opposite end of the suture passing through the tissue, may be passed through the eyelet of the leader snare, as shown in FIG. 6B. In FIG. 6C, the leader snare is then drawn through the knot body (suture trap), drawing the length of suture that has been passed through the eyelet of the leader snare. This length of suture material is thus left passing through the knot body, as shown in FIG. 6D.

As mentioned above, in some variations the suture trap variation of a knot body is configured to permit only sliding of the suture in a single direction (e.g., the direction of the arrow in FIG. 6C), so that the leader snare and the opposite suture length may be pulled to tighten or constrict the suture on the tissue, while preventing loosening of the loop formed by the suture. Thus, a suture strands may be secured within a suture trap in a one-way manner. For example, a suture trap may be formed as a twisting or braiding pathway within a channel through a region of the suture (defining the knot body), or a low-profile modified accessory may form the suture trap, which may be connected to the length of suture. Thus the knot body (suture trap) may include a pathway that will only allow a length of suture to be pulled into it and tightened in a one way manner. In some variations the suture trap may also include barbs within the tunnel in the suture at the 'suture trap' region, a rubbery material, glue or any interference fit or material could also be included. This may provide a knotless means of securing a suture. In some variations, as mentioned above, the knot body region (e.g., suture trap) may be passed through the tissue using a suture passer (e.g., following a needle hole created by a device, instrument or needle).

Figure 6E:
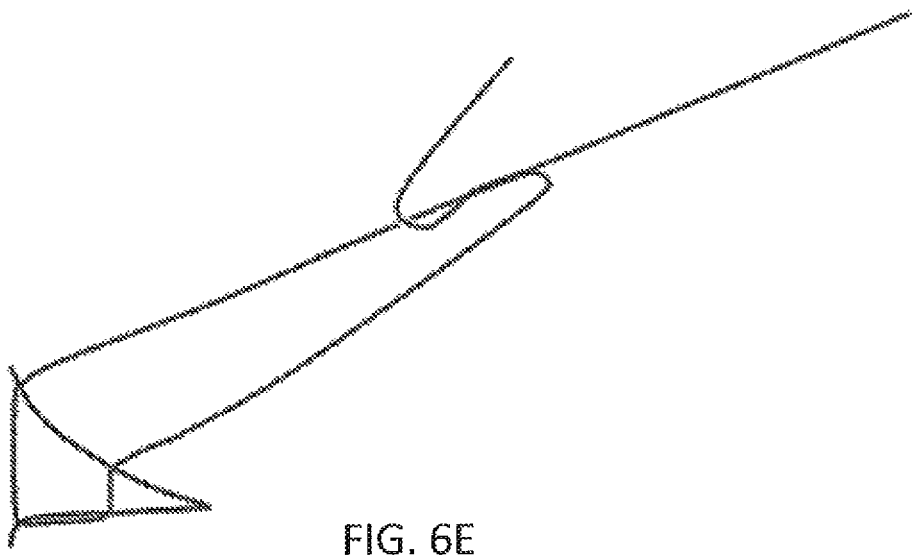
Figure 6F:
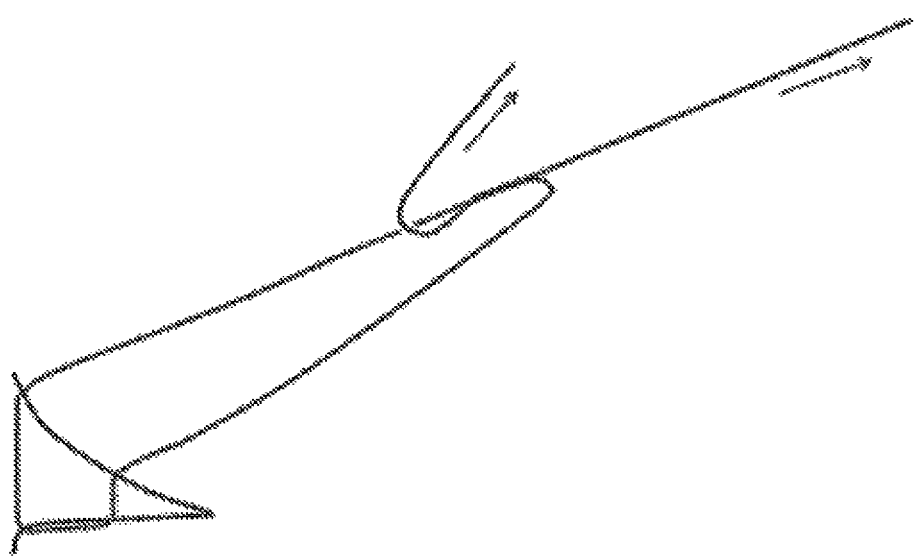
Figure 6G:
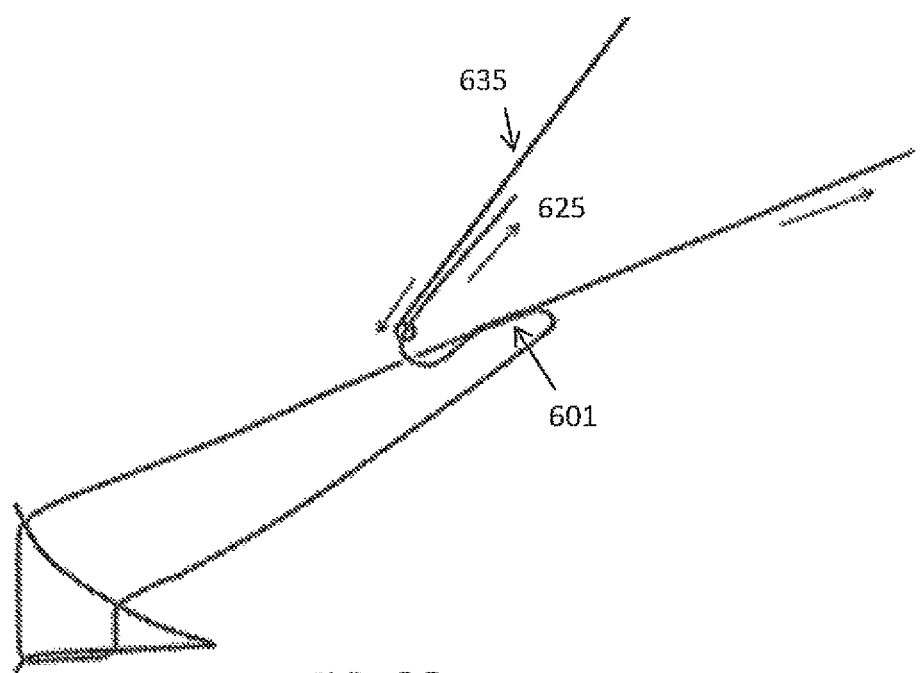
Figure 6H:
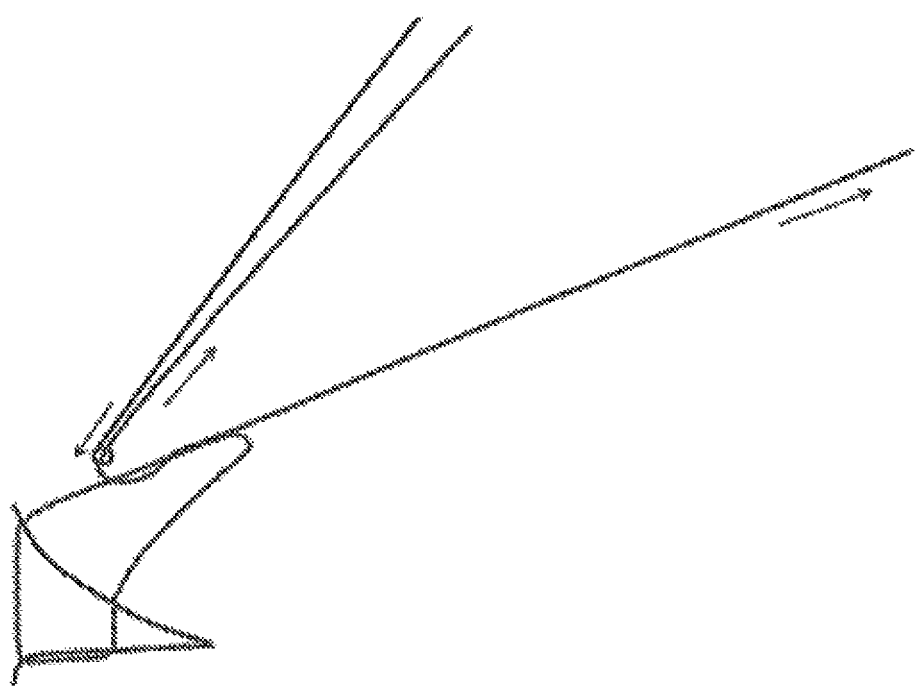
Figure 6I:
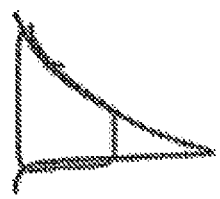

For example, in FIG. 6E the suture length that just passed through the suture trap may be pulled distally (as shown in FIG. 6F) to tighten the loop of suture around the tissue. In FIGS. 6G and 6H the distal end of the suture may be pulled 625, and the pre-tied knot (e.g., the suture trap region of the knot body) 601 may be pushed using a tool such as a knot pusher 635 to slide the trap region down to the tissue surface and tighten the loop of suture. FIG. 6I shows the completed loop tied around the tissue.

In any of the variations described herein, a knot pusher may be used to assist in tying or knotting the suture. In general, the knot pusher may be used to push a pre-tied knot body down the leg or length of suture (while holding the leg or length taut); once pushed to the tissue near where it is to be secured, the second length or leg of suture may be pulled to tighten the knot.

Figure 6J:
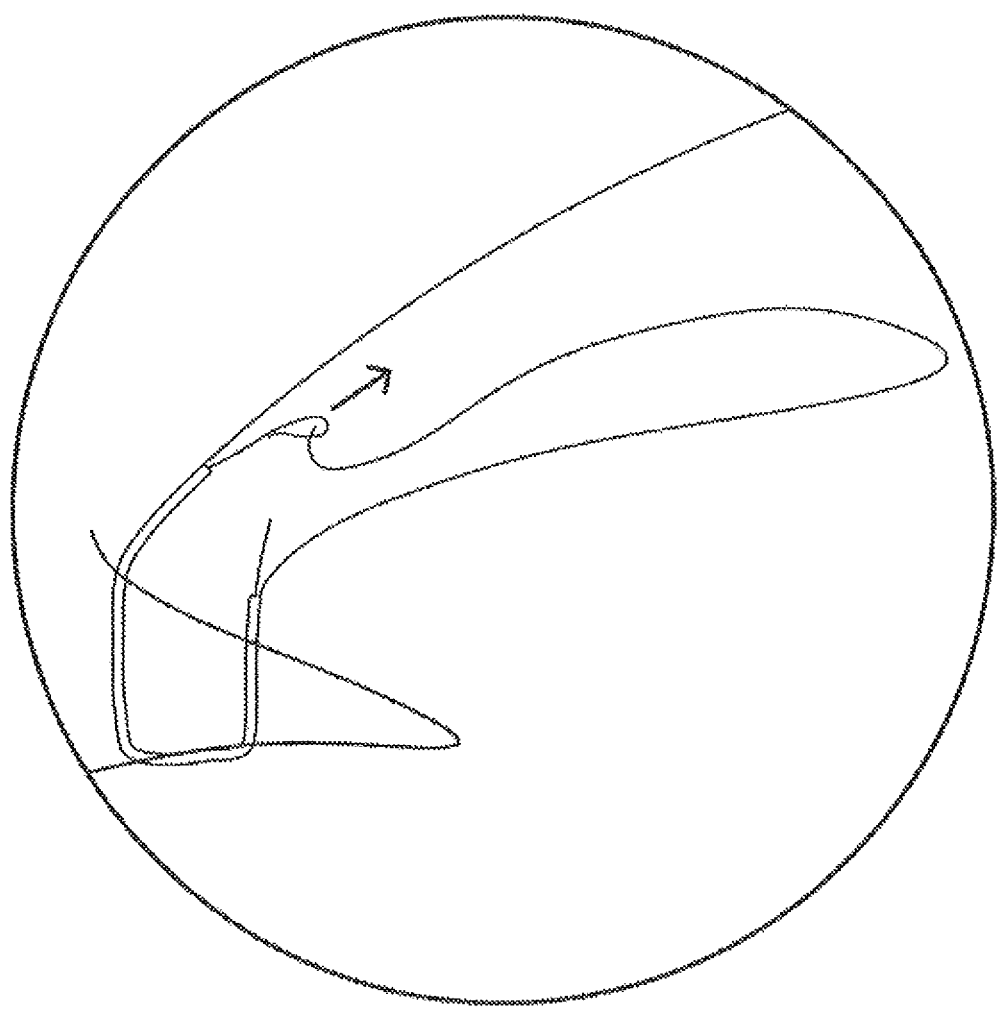
FIG. 6J shows another variation of a suture trap and leader snare for forming pre-tied knot with a suture.

A pre-tied knot may be any appropriate length. For example, a knot body of a pre-tied knot may be short (e.g., a few loops of suture, as described above), or it may be long. FIG. 6J shows one variation of a pre-tied knot body, con-figured as a suture trap, that is very long, and that has been passed through the tissue. In this example, as in FIGS. 6A-6I, the exemplary tissue is shown as knee meniscus, though these pre-tied knots may be used with any appropriate tissue. Passing the entire suture trap/knot body through the tissue in this manner may provide a very strong loop.

Any of the pre-tied knots described above may be pre-packaged within a suture anchor, or loadable into a suture anchor, for use in, as a non-limiting example, rotator cuff repair or labral repair in the shoulder, hip or any soft tissue that needs to be anchored to bone.

Although the description above is broken into parts and includes specific examples of variations of pre-tied knots, any of the features or elements described in any particular example or section may be incorporated into any of the other embodiments.

Pre-tied knots may also be used to suture tissue in another manner as described below. In particular, pre-tied knots may be used by the suture passer to help coordinate passage of the pre-tied knot and suture through the tissue.

Figure 7C:
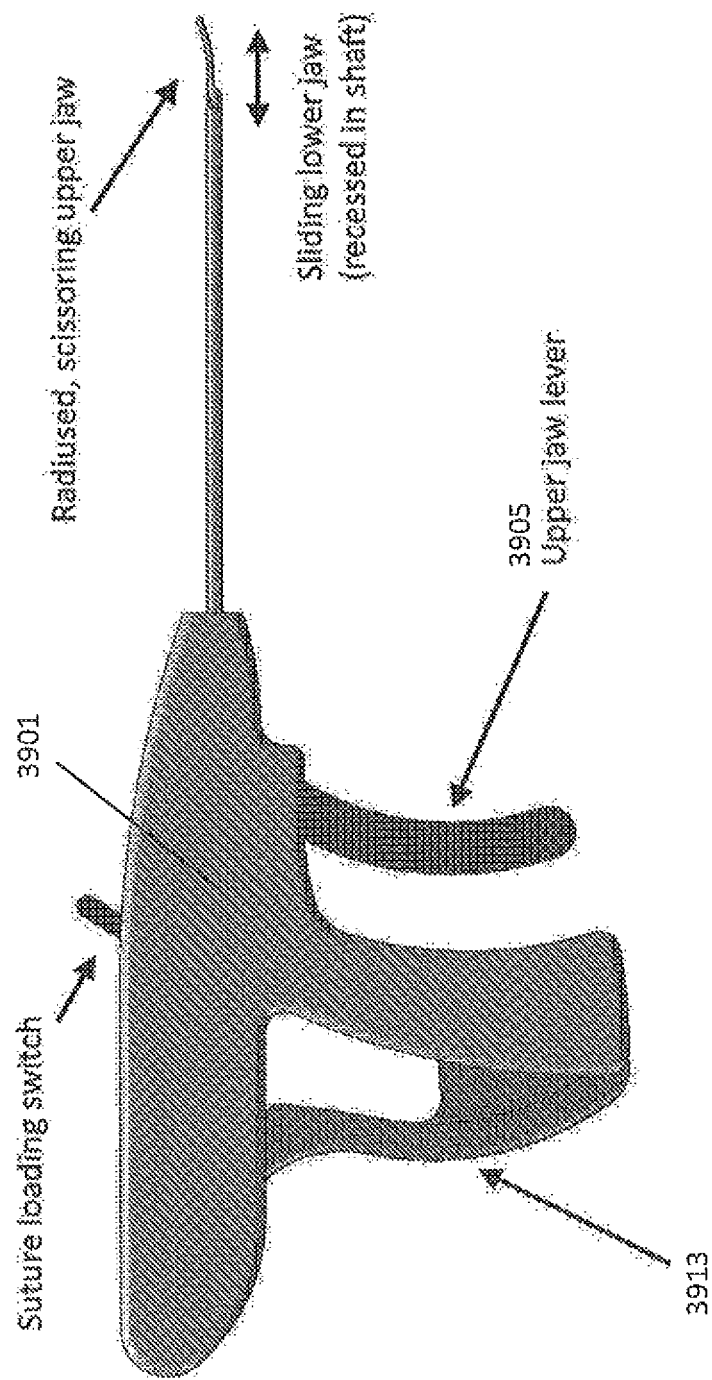

FIGS. 7A-7C illustrate one variation of a suture passer that may be used to place a suture having a pre-tied knot, as described above. Further, a suture passer such as the suture passer shown in FIGS. 7A-7C may also be adapted to suture tissue using one or more lengths of suture that includes a knot, so that the knot is passed through the tissue by the suture passer.

The suture passer of FIGS. 7A-7C has a tissue penetrator that extends distally from a distal opening in the upper jaw. The tissue penetrator travels in a sigmoidal path from the lower to upper jaw. In this variation, two lengths of a suture (including two lengths of the same suture, e.g., two ends of the same suture) can be loaded into the lower jaw and sequentially passed from the lower jaw, through different regions of the tissue and retained in the upper jaw, to pass a length of suture through the tissue. The suture passer show in FIGS. 7A-7C is also configured so that the upper jaw member can pivot to assume a different angle relative to the elongate body of the device, and the lower jaw member is axially extendable distally from the distal end of the elongate member to form a distal-facing mouth with the upper jaw member. The proximal handle includes a plurality of controls for controlling the pivoting of the upper jaw member, the axial sliding of the lower jaw member, and the extension/retraction of the tissue penetrator from the lower jaw member.

FIG. 7B shows the device of FIG. 7A with the outer housing of the proximal handle 3901 removed, revealing some of the connections between the controls and the device. In FIG. 7B, the distal most control 3905, the proximal handle is configured as a trigger or lever that controls the motion of the upper jaw member ("upper jaw control"). The upper jaw control may be pulled to reduce the angle of the upper jaw relative to the long axis of the elongate member 3907. In this variation the upper jaw control is pinned and allowed to drive a tendon in the elongate member distally when compressed to drive the upper jaw down (reducing the angle between the upper jaw and the long axis of the elongate member). This pivoting motion may also be referred to as scissoring (scissoring motion).

A distal control 3913 is also configured as a lever or trigger, and may be squeezed or otherwise actuated to extend and/or retract the lower jaw to form a distal-facing mouth with the upper jaw, as shown in FIGS. 7A-7B. In some variations the control is further configured to control deployment of the tissue penetrator in the sigmoidal path. For example, in some variations squeezing the distal control after completely extending the lower jaw may deploy the tissue penetrator from the lower to the upper jaw so that the distal end of the tissue penetrator extends out of the upper jaw. As it extends between the upper and lower jaw, the tissue penetrator may carry a first length (bight) of suture through the tissue. Upon reaching the opposite jaw member, the suture may be removed from the tissue penetrator and held (e.g., by a stripper) in the upper jaw. Upon release of the distal control, the tissue penetrator may withdraw back into the lower jaw. Actuating (e.g., squeezing) the distal control 3913 again may result in the extending the tissue penetrator (along with any second length of suture) back through the tissue from the lower jaw to the upper jaw, where the second length of suture can be retained. Alternately, in some variations, the controls (e.g., to control motion of the upper and/or lower jaw) may be separate from each other, and/or from extending/withdrawing the tissue penetrator. Additional controls may also be included in the proximal handle, include a suture loading control (e.g., switch, toggle, etc.) for loading and/or tensioning the suture within the lower jaw member.

FIGS. 8A-8D show an enlarged view of the distal end of the device of FIGS. 7A-7C. For example, in FIGS. 8A and 8B the upper jaw 4003 is thin and slightly radiused (e.g., curved), and is hinged to the elongate shaft region of the device. The upper jaw is also connected to a control (handle, etc.) on the proximal handle by a push/pull member (tendon, wire, rod, etc.), allowing adjustment of the angle of the upper jaw member relative to the elongate member.

Figure 10A:
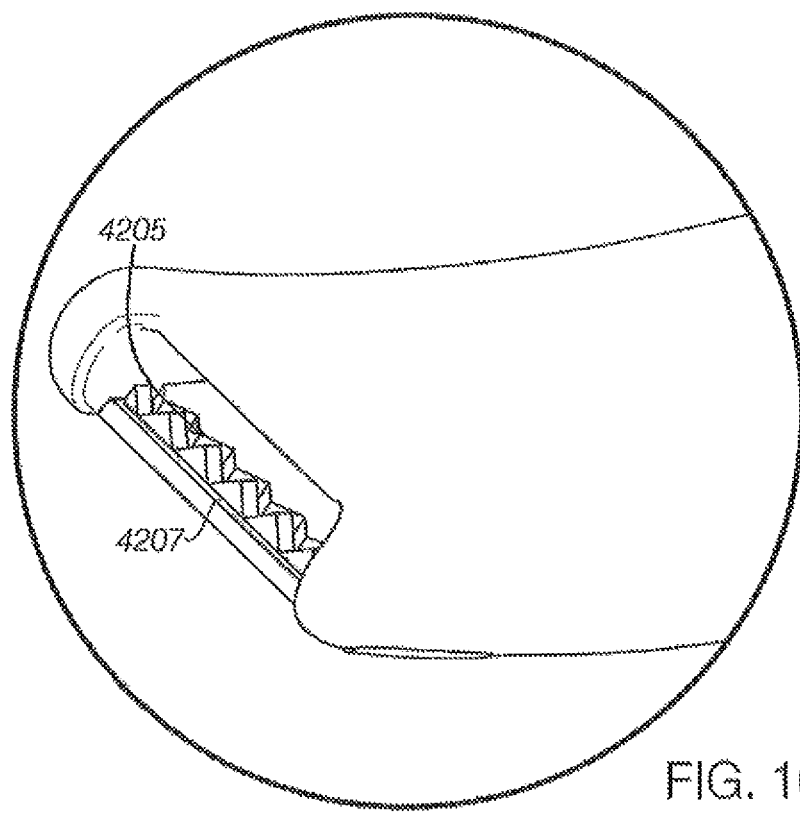
FIGS. 10A and 10B show side perspective views of the distal end region of a jaw member including a suture stripper.
Figure 10B:
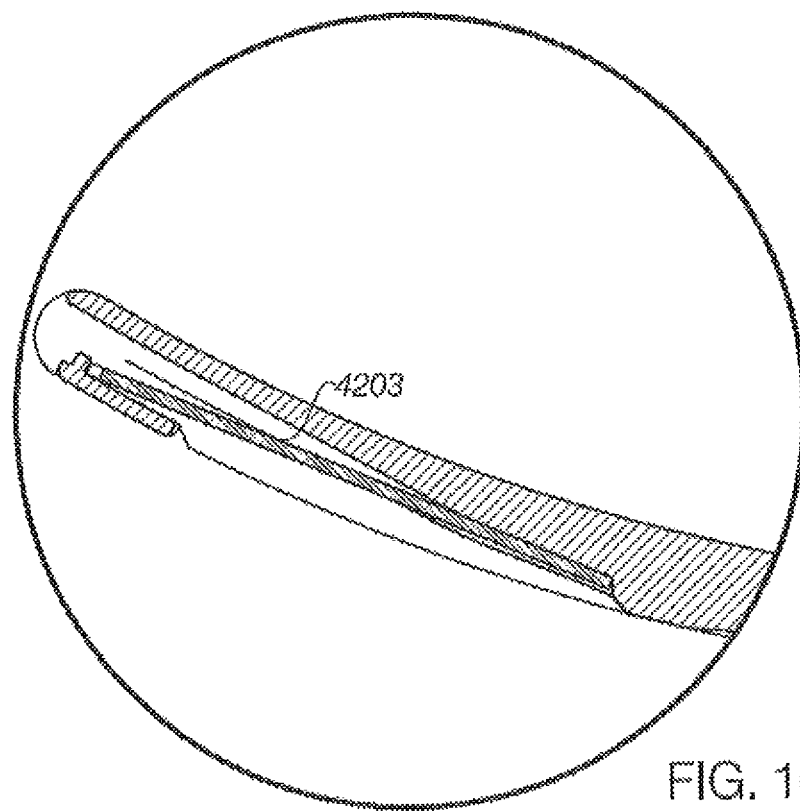

In FIG. 8C, the upper and lower jaw members have been removed from the distal end of the device shown in FIG. 8B, revealing the tissue penetrator 4007 within the lower jaw and the stripper 4009 in the upper jaw. FIG. 8D shows the distal end of the device of FIG. 8B after the tissue penetrator has been extended across the distal-facing mouth. FIGS. 10A and 10B illustrate one variation of an upper jaw region having a suture stripper. In FIG. 10A, the suture stripper is visible from the distal opening at the distal end of the jaw member. In this example, the stripper includes a stripper plate 4203 with a saw-toothed edge 4205. The jaw member also includes a receiver region for the stripper plate having a sawtooth edge 4207.

FIGS. 9A-9C show greater detail on one variation of a suture stripper that may be used. This variation is the same as the variation shown in FIGS. 10A and 10B. Although the examples provided herein show the suture stripper in the upper jaw member, in some variations a suture stripper may be present on the lower jaw member (e.g., where the tissue penetrator is configured to pass a length of suture from the upper jaw to the lower jaw). In FIG. 9A, the stripper includes a flexible plate 4101 that is fixed at the proximal end (e.g. to the upper jaw member), and pressed against a receiving plate 4103 at the distal end 4105. In some variations the receiver is not a separate receiving plate, but merely a region of the jaw member. Either or both the suture stripper plate 4101 and the receiver 4103 may include an edge that is adapted to catch the suture. In FIGS. 9A-9C, both the plate 4101 and receiver 4103 include edges having teeth 4105 and 4107. In this example the teeth are saw-tooth structures that are adjacent (or abutting) in the upper jaw member. The tissue penetrator may pass between the plate 4101 and the receiver 4103 by deflecting the plate 4101; as the end of the tissue penetrator passes the edges 4105 and 4107, a length of suture held by the tissue penetrator may be caught by the stripper and held between the plate and receiver as the tissue penetrator is withdrawn.

In practice, a suture passer having a distally-extending tissue penetrator (including a pre-tied knot) may be used to repair a tissue such as the meniscus of the knee. FIGS. 11A-11F illustrate one method of repairing a torn meniscus using a suture passer such as the one shown above in FIGS. 7A-7C.

The devices and methods described herein may be used to pass a loop of suture and specifically, may be used to form a vertical or horizontal stitch to repair tissue. When repairing the meniscus, a vertical stitch typically provides the strongest repair with the least amount of displacement relative to horizontal stitches or other "all-inside" approaches. The devices and methods described herein may also be referred to as "all-inside" devices and meniscal repair techniques allow the meniscus to be sutured directly. The suture passers described herein may place a fully-circumferential, vertical stitch around meniscal tears. This stitch may provide uniform compression along the entire height of the meniscus and maintain coaptation of the tear at both the inferior and superior meniscal surfaces. Further, because of the jaw and needle configuration, the distal extending tissue penetrator does not penetrate the capsule wall, reducing or eliminating risk to posterior neurovascular structures. These features may allow a greater healing response due to complete tissue coaptation along the entire substance of the tear, improved clinical outcomes due to the greater healing response and to the anatomic reduction and fixation of the meniscus tear, may avoid scalloping or puckering of the meniscus, and may result in less extrusion or peripheralization of the meniscus caused by over-tensioning of suture or hybrid tensioners to the capsule. These devices can also be used to treat radial, horizontal, flap, and other complex tears in addition to longitudinal tears.

In some variations, the suture passer devices described herein can be fired blindly where arthroscopy camera access is poor, as knee structures are protected from the needle path.

Returning now to FIGS. 7A-7C, as mentioned above, the device (e.g., in FIG. 7C) has a scissoring upper jaw that is curved (radiused). This curve may be configured to follow the radius of the femoral condyle. The lower jaw in this example is straight. The lower jaw may be recessed into the shaft, and may slide proximal-to-distal in order to slide under the meniscus along the tibial plateau after the upper jaw is in place along the superior surface of the meniscus. The lower jaw contains a flexible needle, which moves vertically from the lower to upper jaw.

Figure 11A:
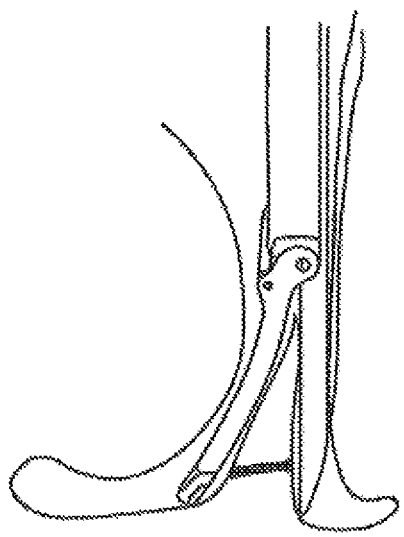
FIGS. 11A-11G and 12A illustrate one method of suturing a tissue in a loop using a suture passer such as the suture passer shown in FIG. 7A.

FIGS. 11A-11F illustrate one method of using a suture passer as illustrated in FIGS. 7A-7C to repair a torn meniscus. As mentioned, the upper jaw of the suture passer may be positioned between the superior surface of the meniscus and the femoral condyle, as shown in FIG. 11A. The thin and slightly curved upper jaw follows the curve of the femoral condyle. The lower jaw is retracted within the elongate body, and has been loaded with two lengths of suture (from end regions of the same suture).

Figure 11B:
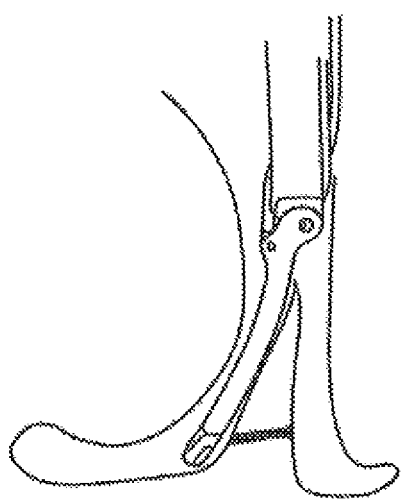
Figure 11C:
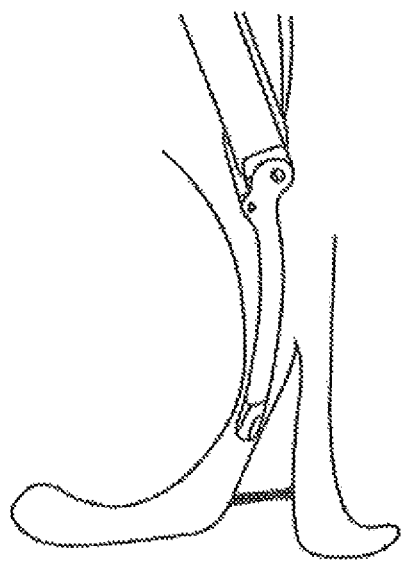

In FIG. 11B, the lower arm is initially retracted; after the upper arm is positioned adjacent to the torn region to be sutured, the lower jaw is extended underneath the meniscus, as shown in FIG. 11C. The sliding lower jaw may more easily accommodate the spatial constraints of the knee than a fixed or scissoring lower jaw. As described above, the lower jaw member in this exemplary device houses a flexible tissue penetrator (e.g., needle) that can be advanced through the meniscus to deliver suture bights from the lower jaw to the upper jaw. Once the device is in position distal to a longitudinal tear or adjacent to a radial tear, the tissue penetrator is advanced from the lower arm to the upper arm.

Figure 11D:
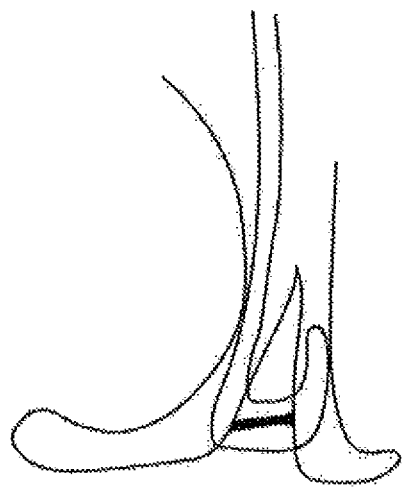
Figure 11E:
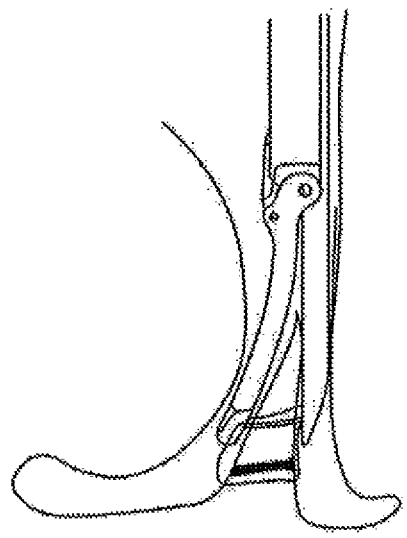

The tissue penetrator pulls one end of the suture strand from the lower jaw to the upper jaw, where it is retained. The tissue penetrator does not pass through the upper jaw, so the femoral condyle remains protected; instead the tissue penetrator extends from a distal opening in the upper jaw, as shown in FIG. 11D. The tissue penetrator is withdrawn into the lower jaw where it engages the opposite end of the suture strand. The device is then repositioned for the second bight, either proximal of a longitudinal tear (see FIG. 11E) or to the other side of a radial tear (not shown in the example). Once in position, the tissue penetrator is advanced to deposit the remaining suture bight in the upper jaw, as shown in FIG. 11E.

Figure 11F:
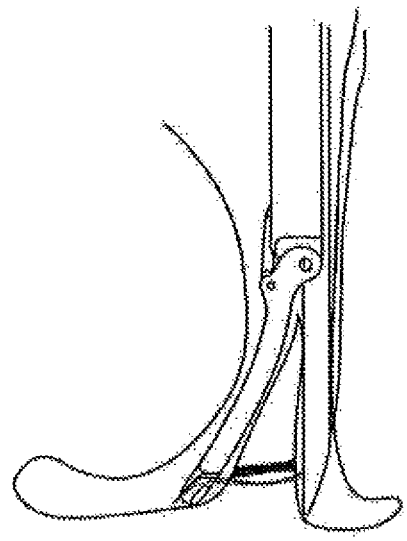
Figure 11G:
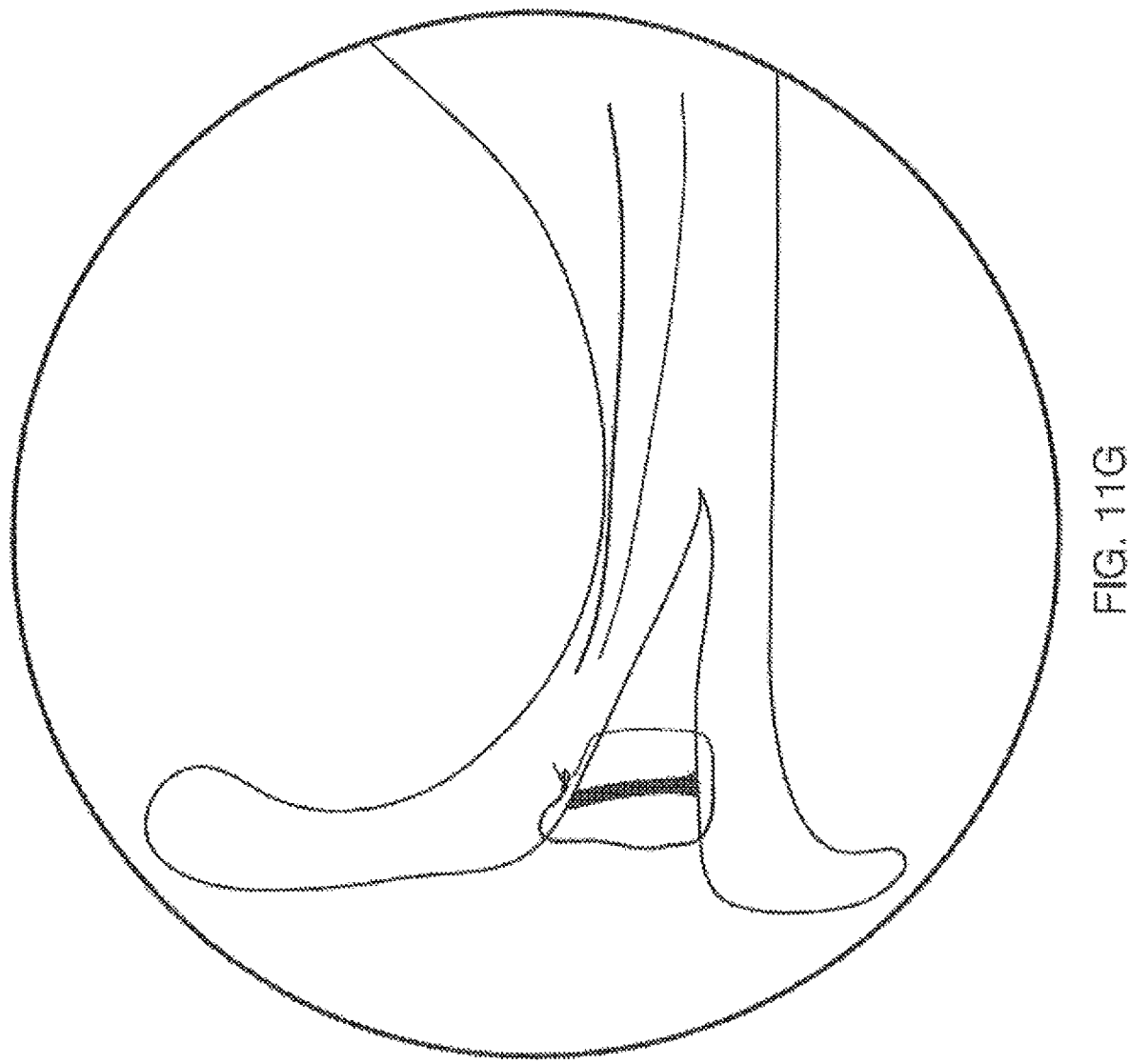
Figure 12C:
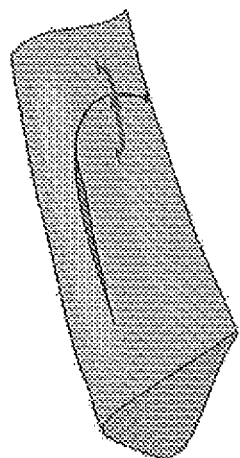
FIGS. 12B and 12C illustrate suturing complex meniscal tears, including those having a radial tear, using a suture passer such as the one shown in FIG. 7A.
Figure 12B:
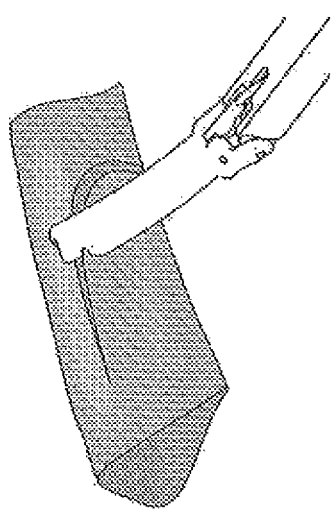
Figure 12A:
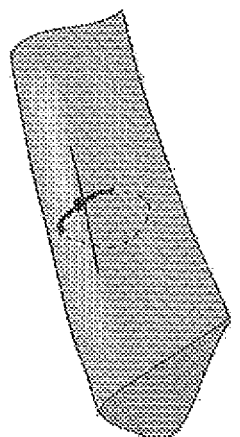

The tissue penetrator can then be brought back into the lower jaw, the lower jaw retracted, and the device may be withdrawn from the knee, leaving a suture loop surrounding the tear, as shown in FIG. 11F, with both ends exiting on the femoral side. A surgeon may then tie and advance a sliding knot (or individual throws) percutaneously, and the loose ends cut, as shown in FIG. 11G. Since both suture-ends may be retrieved through the same track, a cannula is not required to prevent tissue bridging. This may result in a fully-circumferential, vertical stitch around the tear, as shown in FIG. 11G. This vertical stitch completely surrounds the meniscal tear, bringing the superior and inferior margins of the tear in apposition along with the meniscal area in between. FIG. 12A shows a perspective view of a portion of a meniscus repaired in this manner. FIGS. 12B and 12C illustrate how the device and methods described above may also be used to suture more complex meniscal tears, including those having a radial tear.

Figure 13C:
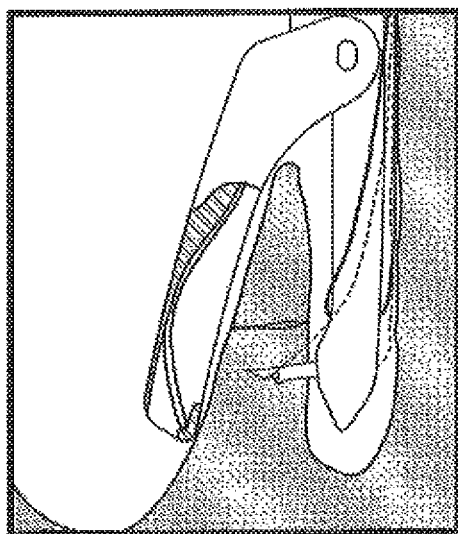
FIGS. 13A-13L show another illustrate of a method for suturing meniscal tissue similar to that shown in FIGS. 11A-11G.
Figure 13F:
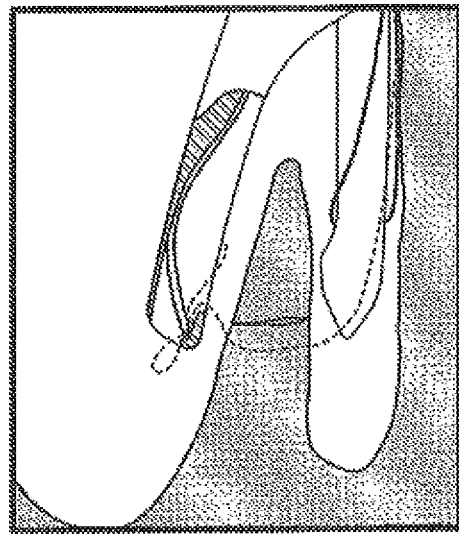
Figure 13B:
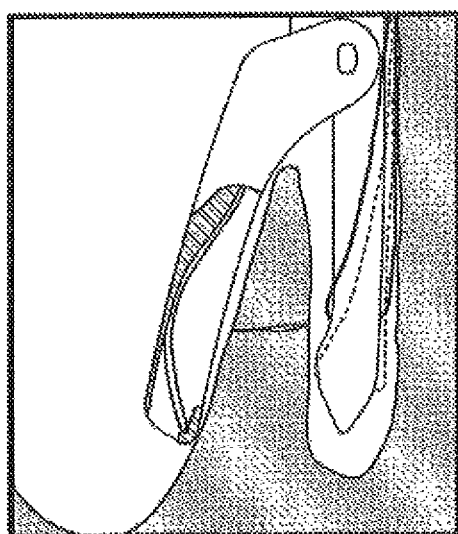
Figure 13E:
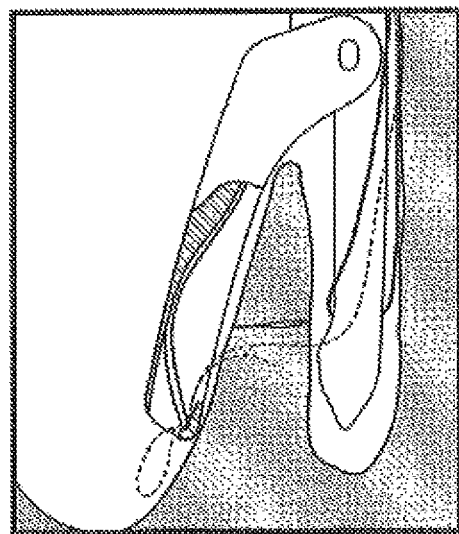
Figure 13A:
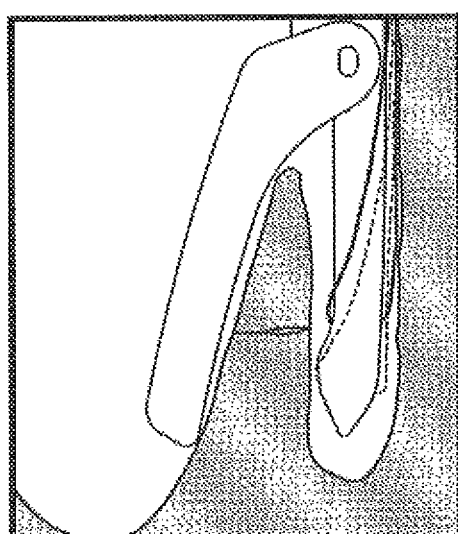
Figure 13D:
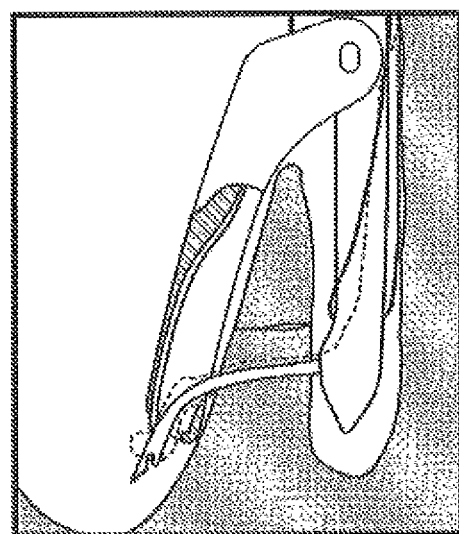

FIGS. 13A-13L illustrate another example of a method for suturing a torn meniscus by passing a loop of meniscus. As just described, the exemplary device shown in FIGS. 13A-13C may be used or other variations of the suture passer devices described herein may be used to suture a torn meniscus. In this example, two regions of a suture are initially loaded into the suture passer in the lower jaw. For example, the first length of suture may be loaded into the tissue penetrator and a second length of suture may be held in a holding region of the lower jaw; the lower jaw may be configured so that once the first length of suture has been passed into the upper jaw member and the tissue penetrator has been retracted, the second length of suture may be loaded into the tissue penetrator for passing through the tissue. In FIG. 13A, the ends of the suture are shown loaded into the lower jaw. In FIG. 13B and subsequent FIGS. 13C-13K, the upper jaw has been removed from the device shown in FIG. 13A to show the deflecting surface and suture stripper (a sheet of metal) in the upper jaw. In FIG. 13C, the tissue penetrator may then be extended from the lower jaw, carrying a length of suture, and pushed through the meniscus towards the upper jaw. The suture passer may then enter into the upper jaw and be deflected by the deflector region within the upper jaw so that it extends distally out of the upper jaw member, as shown in FIG. 13D. In this example, as the tissue penetrator pushes up into the upper jaw it pushes the stripper out of the way, allowing the suture to advance beyond the end of the stripper. In FIG. 13E, retracting the tissue penetrator leaves the suture held by the stripper in the upper jaw. The stripper places a downward force on the tissue penetrator as it retracts, this force strips the suture off of the tissue penetrator and then pins the suture length in the upper jaw.

Figure 13G:
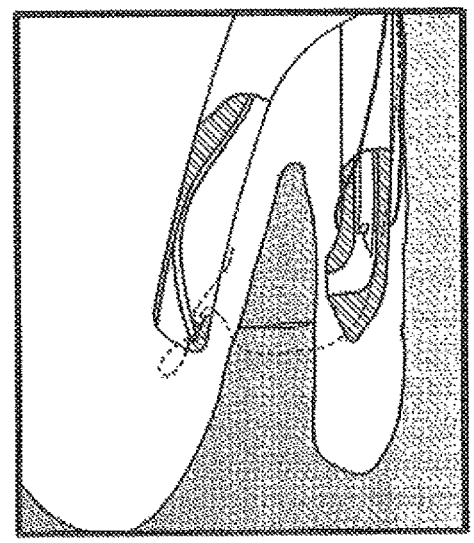

As shown in FIG. 13F, the device may then be repositioned to fire a second time. The device is moved to the second location. Moving the device does not dislodge the suture from the upper jaw, as it is secured by the stripper. Retracting the tissue penetrator into the lower jaw may cause the second end of the suture to be loaded into the tissue penetrator, as shown in FIG. 13G.

Figure 13H:
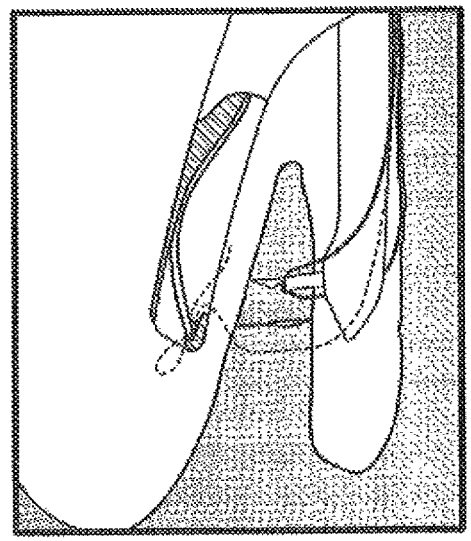
Figure 13I:
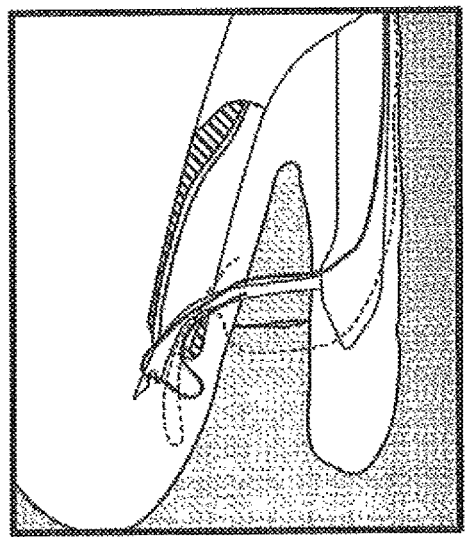
Figure 13J:
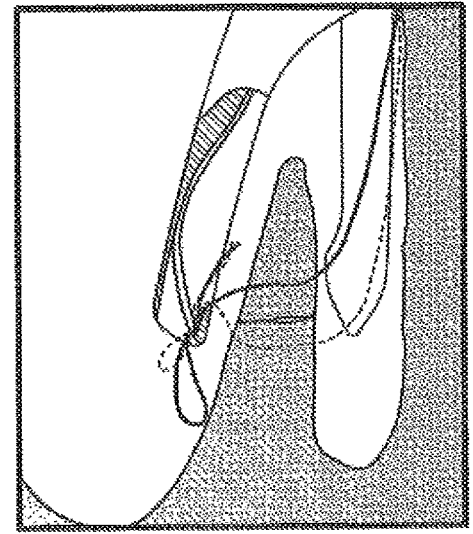
Figure 13K:
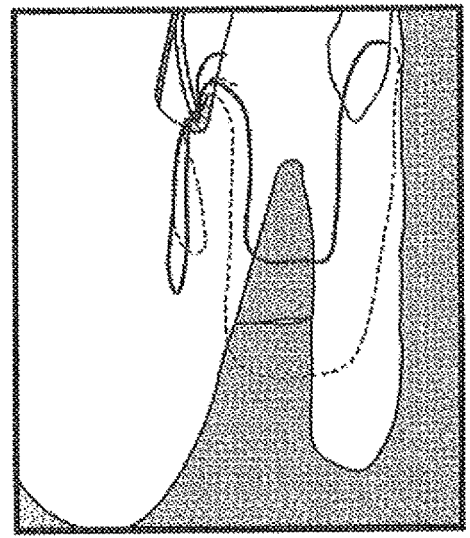
Figure 13L:
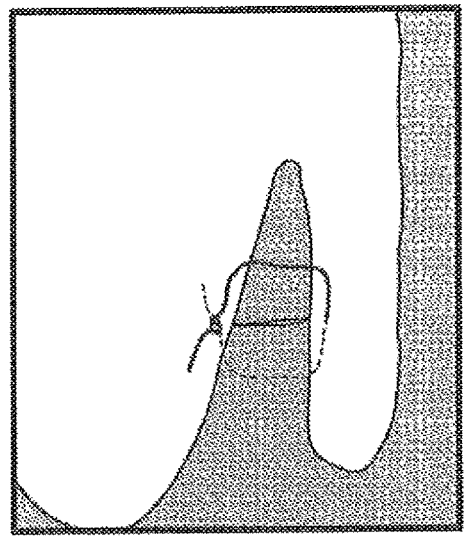

The tissue penetrator can then be extended back across the tissue from the second position on the opposite side of the meniscal tear, as shown in FIG. 13H. The tissue penetrator carries the second length of suture with it to the upper jaw, and past the stripper again, as shown in FIG. 13I. As before, withdrawing the tissue penetrator after extending it out of the distal end of the upper jaw so that the second length of suture extends beyond the stripper results in the stripper retaining the second length of suture along with the first length of suture, as shown in FIG. 13J. The device may then be retracted with both sutures pinned in the upper jaw, as shown in FIG. 13K. The device may be fully retraced, and the ends of the suture tied, as shown in FIG. 13L. As discussed above, the suture may be tied using a pre-tied knot. Thus, one or the other loop of suture lengths (bights) passed through the tissue as described above for FIGS. 13C/13D and 13H/13I may include a pre-tied knot that is passed with the length of suture.

Alternatively, in some variations a knot of suture may be passed through tissue using a suture passer as describe above in which a pre-tide knot is used to help secure the length of suture being passed to the device. For example, in some variations an end region of one or both (in variations in which two lengths of suture are being passed) lengths of suture are knotted, and this pre-tied knot may be passed through the tissue by the tissue penetrator. The pre-tied knot may or may not include a leader snare as described above. For example, in some variations two lengths of suture (from the same elongate suture) may be passed through a tissue; both lengths may be pre-knotted, however only one of the pre-tied knots may include a leader snare and be configured to allow another length of suture to be pulled through.

FIGS. 14A-14J illustrate a method of passing a suture (two length of suture in this example, though a single pass may also be performed) using a knot capture method in which the lengths of suture are knotted near their ends and the knots of suture are passed by a suture passer. In this example a plastic piece is used to represent tissue. Although these figures describe pre-knotted ends, in some variations the "knots" are formed by non-suture materials, or by means other than tying the suture. For example, as mentioned above in the general case, a "knot" may be formed exclusively from loops of suture, or it may be formed without looping the suture, and/or from non-suture material. For example, in FIGS. 14A-14J, the knots at the ends of the suture may be formed by heating the suture ends to create an enlarged region (e.g., a "mushroom head" feature), by crimping a metal piece that helps facilitate suture trapping, by creating an eye splice or eyelet in the ends of the suture which interact with the needle, etc. One or both knots in the suture may be formed in this manner. In general, such knots are formed by an enlarged region relative to the rest of the length of the suture.

Figure 14A:
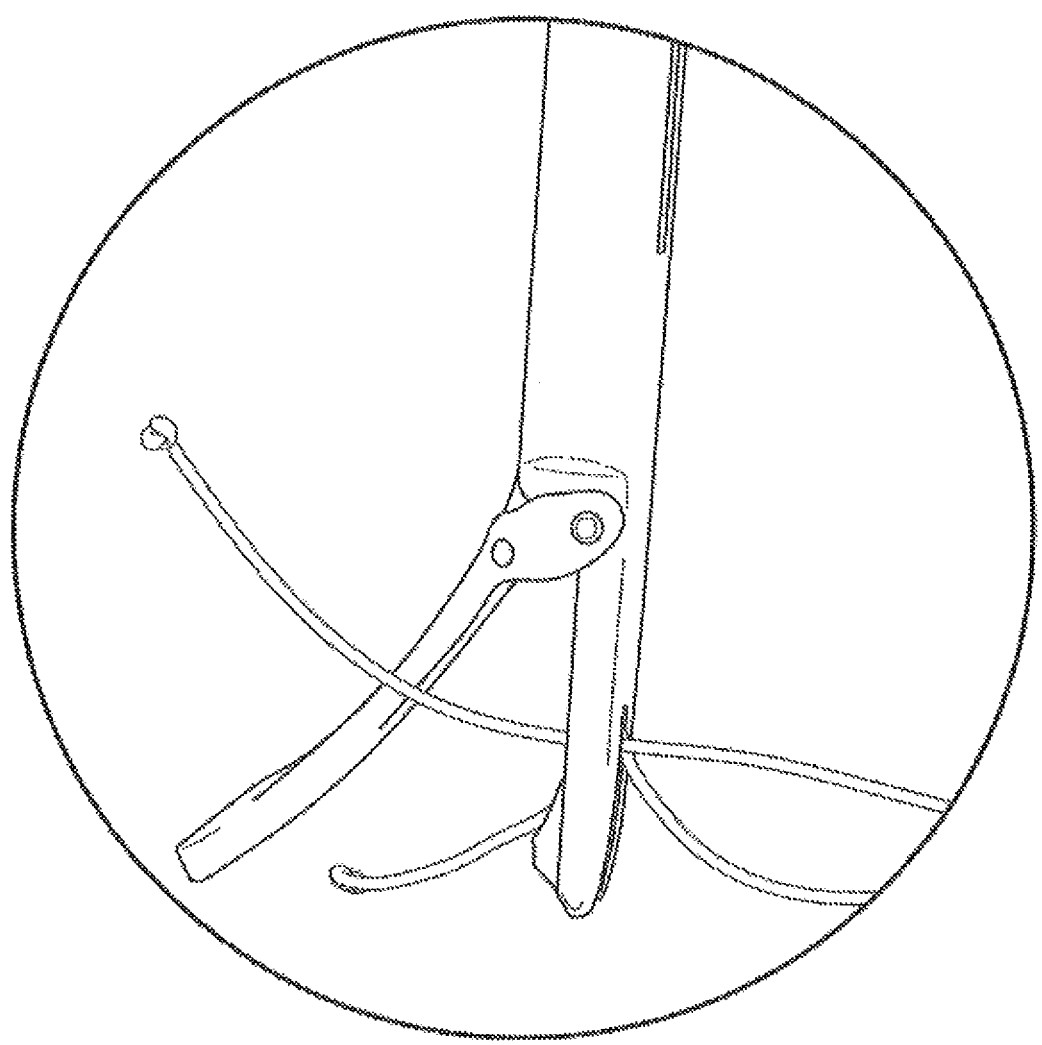
Figure 14B:
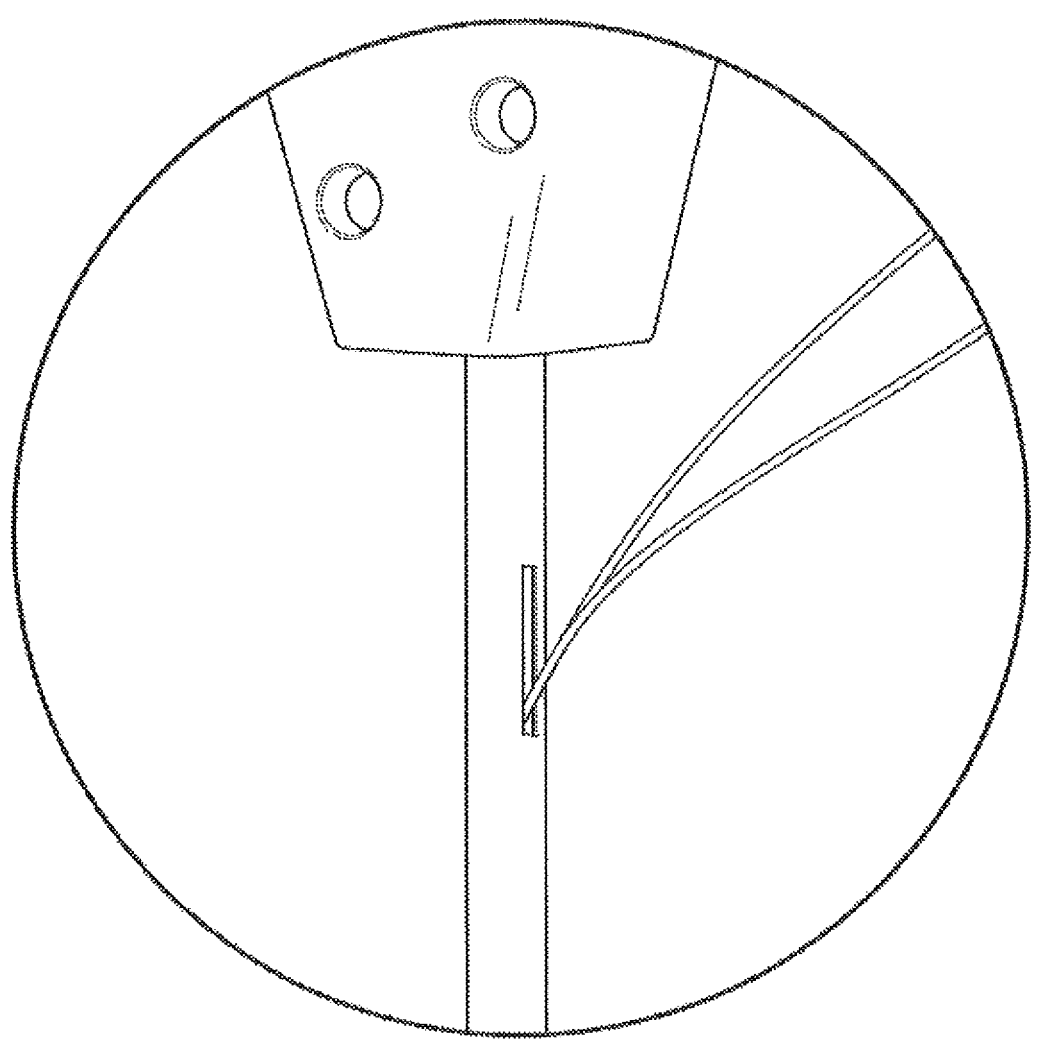

For example, in FIG. 14A an elongate line of suture is knotted at both ends, and these ends are loaded into the suture passer. In this example, the suture passer is similar to the variation shown above (e.g., in FIGS. 7A-7C), and the suture knots are pre-loaded into the lower law member, which is adapted to hold them. In some variations the entire line of suture is pre-loaded into the lower jaw. The tissue penetrator may include a suture retainer comprising a hooked region into which the narrower region of the suture (behind the knot at the end of the suture) may fit. The hook region may be smaller than the diameter of the knot. Thus, the suture end may be held securely in the hook region while passing the suture end through the tissue, and it may be uncoupled from the tissue penetrator when it is withdrawn in the opposite direction.

As mentioned above, in this example, the suture may be held within the tissue penetrator (e.g., in the body of the device) to protect it as it is being used. For example in FIG. 14B the suture extends through the lower jaw and through the elongate length of the member until it exits near the distal handle. Thus, the suture may be held within the body of the device either completely or partially. The knotted ends may be pulled taught into the lower jaw (FIG. 14C); the knotted ends may be completely pulled into the lower jaw, as shown in FIG. 14D. Once the device is pre-loaded with suture, the lower jaw may be retracted; the suture may be pulled taut proximally so that the distal knots remain in the lower jaw, even as it is retracted axially.

The device may be similar to the device described above, but may be adapted to hold one or (as shown in this example) more (e.g., 2) knots at the ends of the suture length.

Figure 14C:
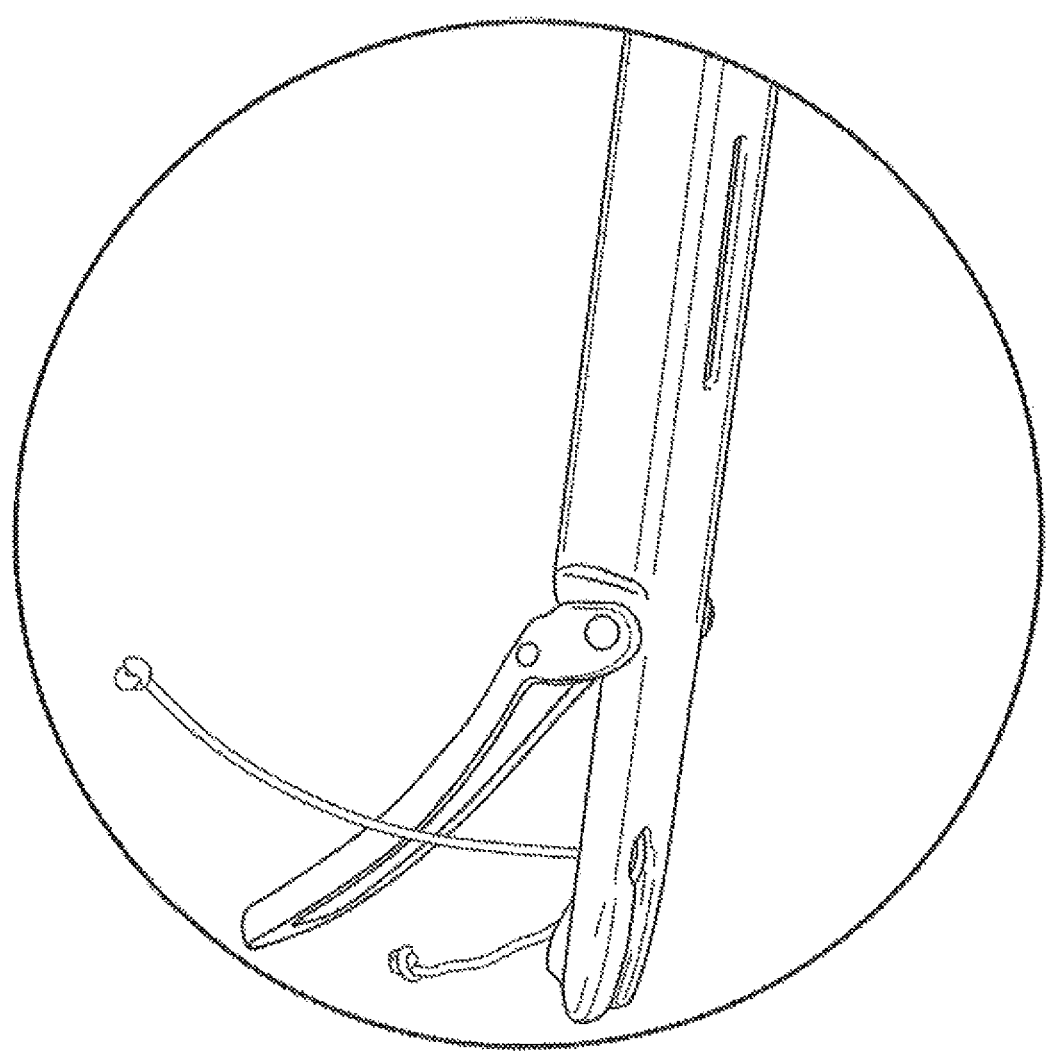
Figure 14D:
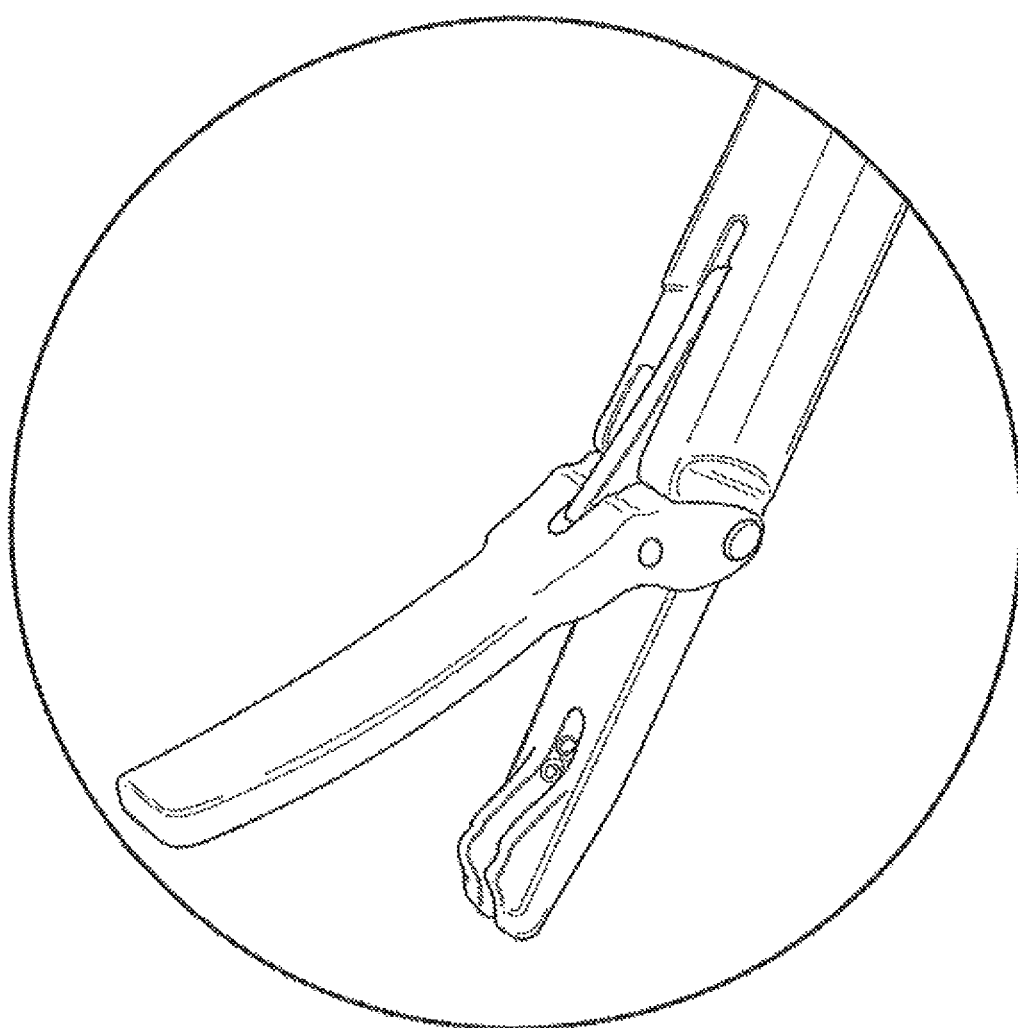
Figure 14E:
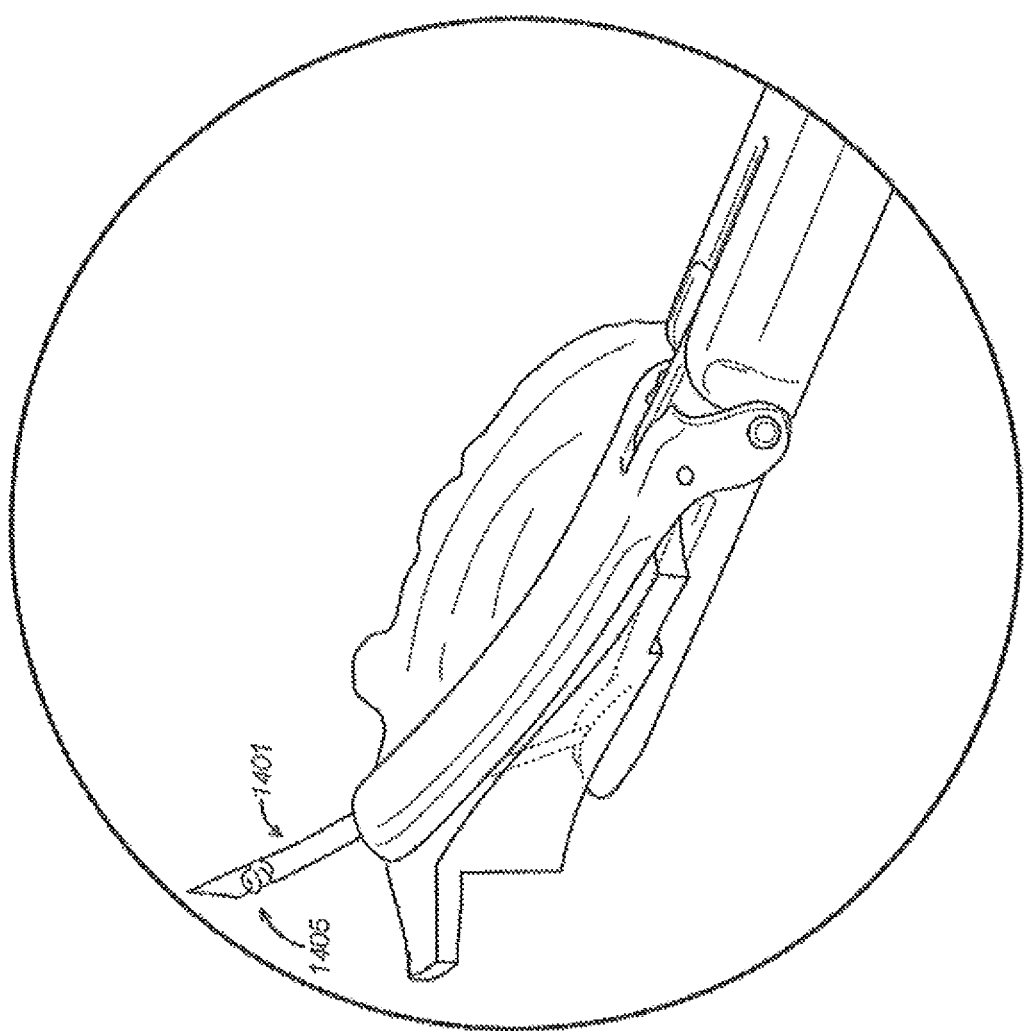

The device may be placed over the tissue as described above (e.g., by adjusting the angle of the upper jaw, and extending/retracting the lower jaw as necessary to surround the tissue to be sutured in the distal-facing opening, as shown in FIG. 14E. In this example, the tissue penetrator extends from the lower jaw, carrying a first knotted end of the suture through the tissue and up into the upper jaw and distally out of the upper jaw. The suture is held in the tissue penetrator 1401 and the knot 1405 prevents it from pulling out, as illustrated in FIG. 14E. Thus, the tissue penetrator picks up on the knot and drags the suture line (and knot) through the tissue and up into and through the upper jaw. In some variations the knot and suture may be held in the upper jaw and the tissue penetrator may extend up and pull the knot down to the lower jaw, instead.

Figure 14F:
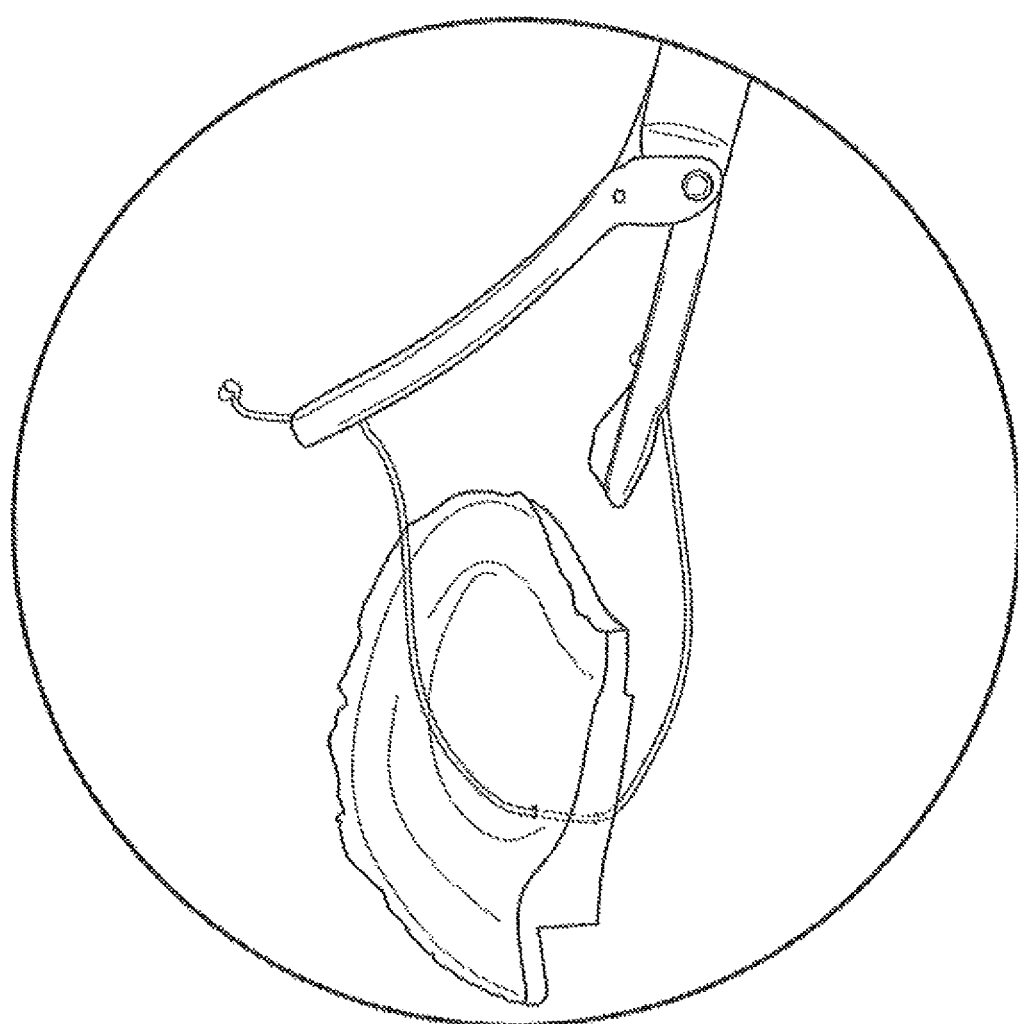
Figure 14G:
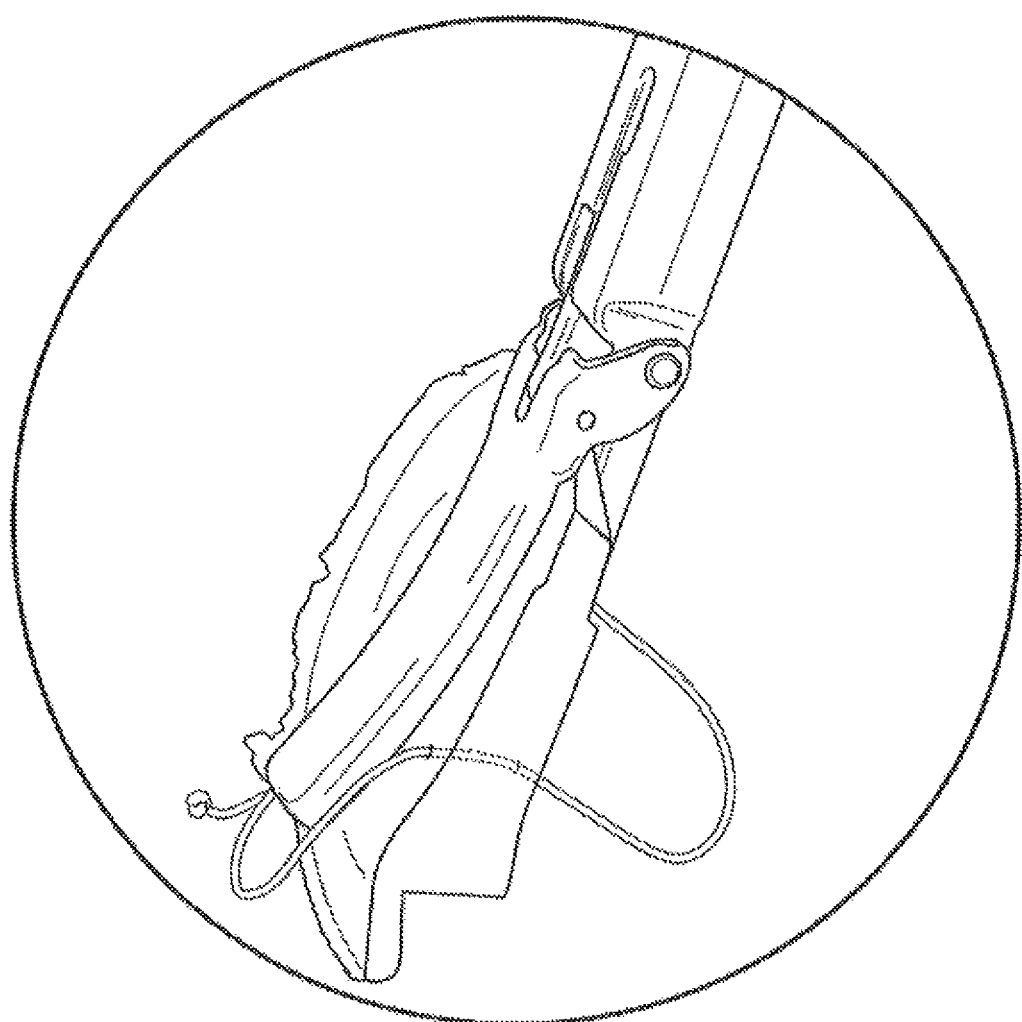

After passing the knot to the upper jaw, the knot may be retained by a strip mechanism in the upper jaw (not visible, but see, e.g., FIG. 9A), and the tissue penetrator retracted. In some variations the retainer in the tissue penetrator (e.g., cut-out region, opening, etc.) is angled so that withdrawing the tissue penetrator readily allows the suture to exit the tissue penetrator, although when driving the suture through the tissue the suture remains seated in the tissue penetrator. In FIG. 14F the device has been withdrawn from the tissue model to illustrate the single pass of the suture after retraction of the tissue penetrator. In practice, the suture passer device may remain on the tissue, although the position may be adjusted, and it does not need to be completely withdrawn from the tissue to reload another suture end. The device may thus be repositioned on the tissue to make the second pass of the suture, without removing the device from the body (or far from the tissue).

The tissue penetrator may be extended again across the tissue to pass the second end of the suture. The second end of the suture may be automatically reloaded into the tissue penetrator. For example, the second end and knot may be held in a holding region of the lower jaw; once the tissue penetrator returns to the lower jaw and the suture retainer in the tissue penetrator is empty, the second suture length (the second end) behind the knot may enter the suture retainer.

Figure 14H:
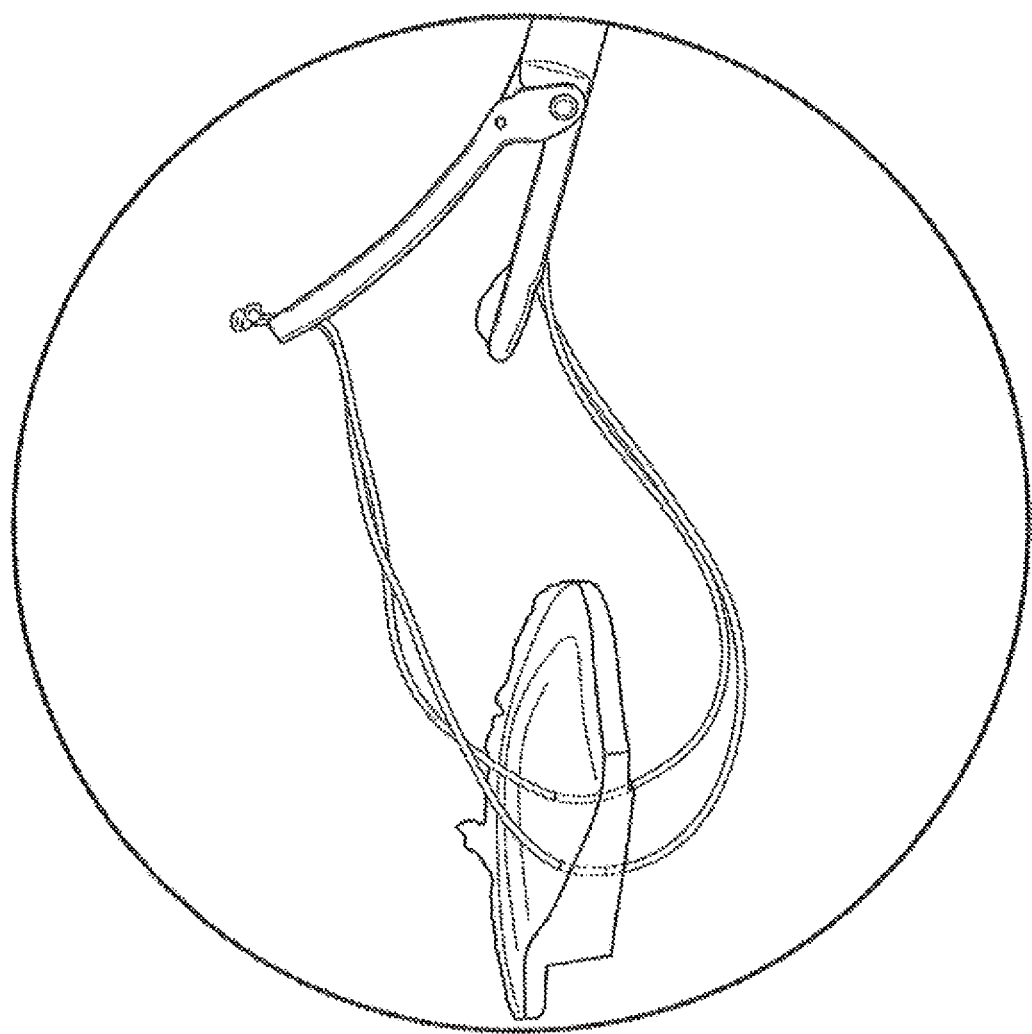
Figure 141:
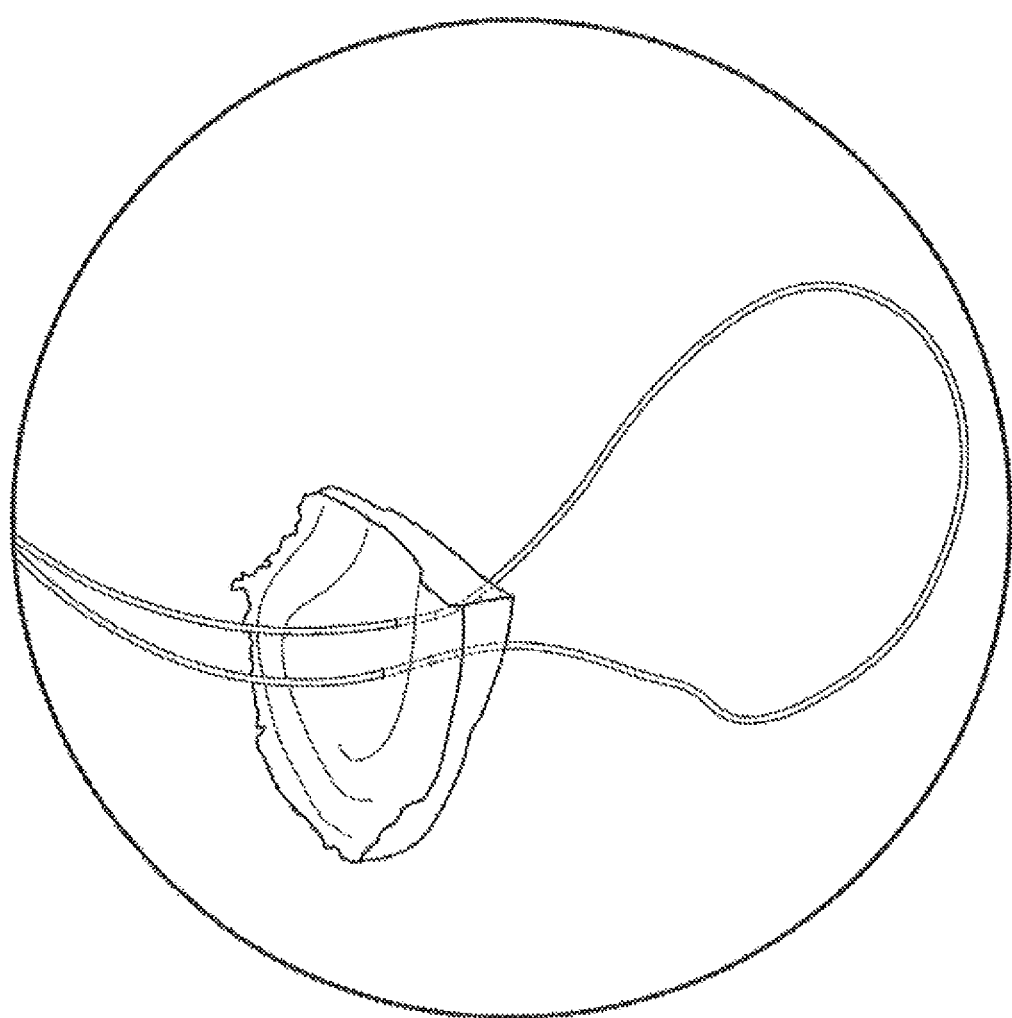
Figure 14J:
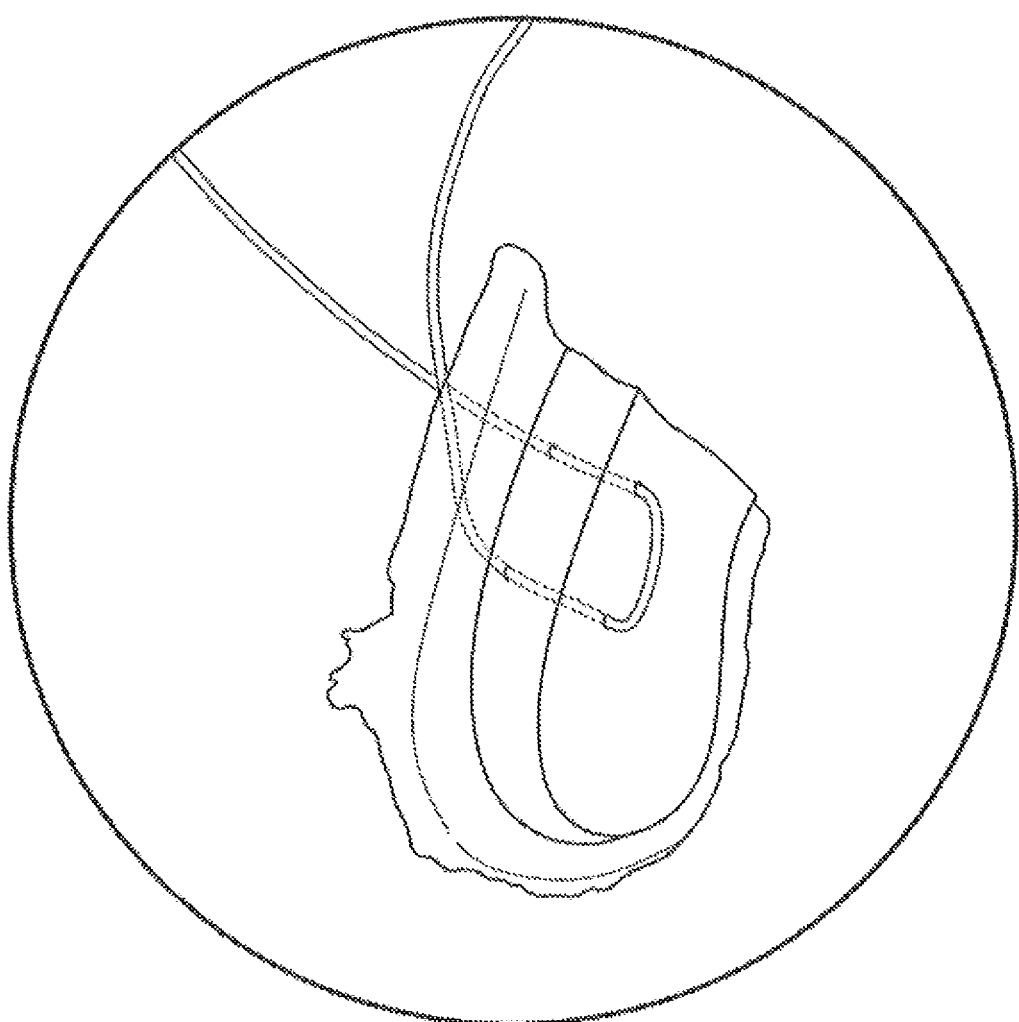

In FIG. 14C, the second end of the suture is passed through the model tissue by again advancing the tissue penetrator. The second knot is passed from the lower jaw member, through the tissue, and up and into the upper jaw. Because the suture is knotted it is held securely by the upper jaw (e.g., the strip mechanism in the upper jaw). Knots are not able to come back through the upper jaw strip mechanism. Once both ends (or lengths) of the suture have been passed, the suture passer device may be removed from the tissue as shown in FIG. 14H. In FIG. 14H the device has been removed without retracting the lower jaw, however in general, the lower jaw may be retracted and the upper jaw bent as necessary to remove the device from within a narrow region of tissue (e.g., the knee). The suture will be left behind in the tissue and the preloaded suture may be pulled from the lower jaw to allow the device to be retracted fully, leaving the loop of suture passed through the tissue, as shown in FIG. 14I. This loop may be pulled taught, as shown in FIG. 14J. Finally, the ends of the suture removed from the tissue penetrator and the loop knotted or tied.

In some variations the ends of the suture (knots) are cut from the suture passer. In some variation, a release mechanism may release the knots from the mechanism (e.g., strip mechanism) in the upper jaw holding them. For example, a release on the handle may remove tension from the strip mechanism, allowing the knots to be released from the upper jaw. In some variations at least one of the knots may be a pre-tied knot as described above, or an additional pre-tied knot may be located proximally to one of the end knots. Thus, a pre-tied knot may be used to tie the two ends together to secure the loop within the tissue.

In general, a device that passes a knot through the tissue may be referred to as a knot capture device, since it is configured to capture and pass knots that are tied to a length of suture (particular near the end or ends of the suture length).

Knot-tying Jigs

Also described herein are devices for aiding a healthcare professional with tying secure suture knots quickly and easily. In general, the knot tying accessory includes a guide body and a plurality of guides within or on the surface of the guide body for winding a piece of guide thread or suture through. In some embodiments of the knot tying accessory device, the device includes capture loops disposed on the end or ends of the guide thread that aid in pulling the suture ends through the guide body to form a particular knot pattern.

In general, the guide body is a first portion of the knot tying accessory device. The term "guide body" is used to describe portion of the device that is able to accept and retain the piece of guide thread or the piece of guide thread coupled to a bight of suture. The guide body can be any particular shape. In some of the examples, the guide body is in the shape of a rectangular case. The guide body in some instances can be opened to expose an interior space that is defined by channels. The guide body may also include a series of openings where the guide thread is first threated and where portions of the guide thread is accessible.

The guide body may be constructed to resemble a puzzle having openings or couplers. In these instances, the guide thread or the bight of suture may be coupled in a particular way about the guide body. After the guide thread or the suture has been coupled to the guide body, portions of the guide body is able to rotate in a particular sequence to form a knot. In the case, where the guide thread is used, the guide thread would then couple to the end of a suture and be used to pull the suture through the path about the guide body. Once the knot has been formed, the guide body is able to release the knotted suture, where the knotted suture may then be cinched down against the tissue.

The guide body may be constructed of any suitable materials such as plastics, metals, and other natural, man-made materials, or some combination thereof. In some instances, there may be instructions or directions on the guide body to aid the user in lacing the guide thread or the suture in the device body. The instructions may be arrows, numbers, wording, or pictures that show how to thread the guide thread or suture through the device.

In general, the term "convoluted pathway" as used in this disclosure means the path or paths defined within the interior space, the outer surface, or a combination of inner and outer surface that is able to define a pathway, where the pathway may cross over itself at multiple points throughout the path. In some embodiments, the guide body includes channels within its interior space that define the convoluted pathway. In other embodiments, instead of channels, posts or other protrusions may be included within the interior space of the guide body for lacing the guide or suture thread through the convoluted path. Also, a combination of channels and/or protrusion may also be used. In some examples of the channels and/or protrusions that define the pathways available for the guide or suture thread are stationary and thus able to only define a limited number of convoluted pathways within the guide body. In other examples, the channels and/or protrusions that define the convoluted pathway may be adjusted to form new pathways through which the guide or suture thread may be laced to form new knot patterns.

Typically the convoluted pathways that the suture and guide thread will take has a sweet spot with regards to the angles of each of the turns that the path would take. It would not be desirable to have the guide or suture thread move past a sharp ninety degree angle as this would cause much friction and may case the guide or suture thread to be caught within the device body. It is thus preferable to have the pathway that the guide or suture thread travel be curved or straight to reduce the amount of friction when the guide or suture thread experiences while being pulled through the convoluted pathway.

In general, the term "guide thread" is used to describe a line that is able to couple with a bight of suture. The guide thread is pre-laced within the guide body prior to coupling with the bight of suture. The guide thread may be constructed from a thread made of natural or synthetic material. One criterion is that the guide thread be easily pulled within the convoluted pathway of the guide body. In some instances, the guide thread may be coated with a material having a low coefficient of friction. In other instances, a lubricating substance may be interwoven into the thread fibers. The coefficient of friction being less than 0.5 or less than 0.1.

In some of the embodiments of the knot tying accessory device, the guide thread includes a "capture loop" at one end. In general, the capture loop functions to couple with the bight of suture and to pull the suture through the convoluted pathway for forming a knot. The capture look may be of the same material as that of the rest of the guide thread or of a different material. In some examples, the capture loop is a piece of thread-like material and may be cinch down onto the bight of suture like a sliding knot. In other examples, the capture loop may contain a mechanism for clamping down and grabbing the bight of suture for drawing the bight of suture through the guide body and then releasing the bight of suture once the suture has been drawn through the desired portions.

The knot tying accessory may also include "pull tabs". In general, "pull tabs" are tabs or pulls that can couple to portions of the guide thread that are exposed when the guide thread has been threaded within the guide body. The pull tabs can be of any suitable shape or size as long as they are easy to pull and grip. The pull tabs may be able to couple to the bight of suture through a coupler such as a clip.

A first embodiment of the knot tying device 100 is shown in FIGS. 15A-15F. Device 100 includes a device body 101; a series of openings, 102, 103, 104, and 105; an interior pathway 106; a guide thread 110, and a first and a second pull tab 112 and 113, respectively. In this embodiment, the device is largely rectangular but the device body can take on any shape suitable for having an internal pathway that can guide a line such as a thread to be tied into a knot pattern. In some examples, the device is openable to show the interior pathway. A user can then thread the guide thread 110 through the interior pathway 106 to arrive at what is shown in FIG. 15A. In some instances, there may be instructions on the device body using arrows, numbers, or other suitable instructions to aid the user in threading the guide thread through the interior pathway. In other instances, there may be separate instructions on how to thread the guide thread through the interior pathway. There may also be multiple ways that a line may be threaded through the interior pathway for forming a knot.

FIG. 15A shows the guide thread 110 already laced through the interior pathway 106. The interior pathway 106 will typically have a convoluted route for forming a complex knot wherein the path forces the line following its path to cross over on itself at least once and often times more than once. FIG. 15A also shows that the guide thread 110 also includes a capture loop 111 that is disposed on an end of guide thread 110. The guide thread 110 is a contiguous piece of material. The capture loop 111 in FIG. 15A is shown at opening 102. The guide thread comprises a single piece of material. The lighter color portion of the guide thread 110 shown in FIGS. 15A-15F are for showing the portion of the guide thread 110 that will be exchanged with a first end of a suture.

FIG. 15B shows the next step where the first end of a piece of suture is inserted through capture loop 111. A user can then pull the first pull tab 112 to start the exchange of the guide thread 110 with a portion of the first end of the suture where the first end of the suture enters the interior pathway 106 of the device body 101 at opening 102. Note here that the first pull tab 112, located at opening 103, can only easily pull on one side of the guide thread 110. In the setup shown for this embodiment, the second pull tab 113 prevents the upper or left portion of the guide thread 110 from being pulled through the interior pathway 106 and only the right or lower portion of the guide thread 110 is able to be pulled through the interior pathway 106.

FIG. 15C shows the resulting configuration once the first end of the suture has completely replaced the first portion of the guide thread 110 within the interior pathway 106. Here, the capture loop 111 end of the guide thread 110 has exited the first portion of the interior pathway 106. The first pull tab 112 can be uncoupled from the guide thread 110. Next, the user can pull second pull tab 113 which is attached to a second, free end of the guide thread 110. This brings the capture loop 111 to the opening 104.

Turning to FIGS. 15D, 15E, and 15F, the capture loop 111 is shown being coupled to a second end of the suture in FIG. 15D. The user can pull on the second pull tab 113 which starts the replacement of the latter portion of the guide thread 110 with the second end of the suture. The user will continue to pull on the second pull tab 113 until the second end of the suture starts to exit from opening 105. At that point, the entire interior pathway 106 has been replace with the first and the second suture ends. Finally, FIG. 15F shows the loose knot configuration after the user has removed the device from the knot. The knot bundle than can be cinched against the tissue to hold the suture together.

Figure 16:
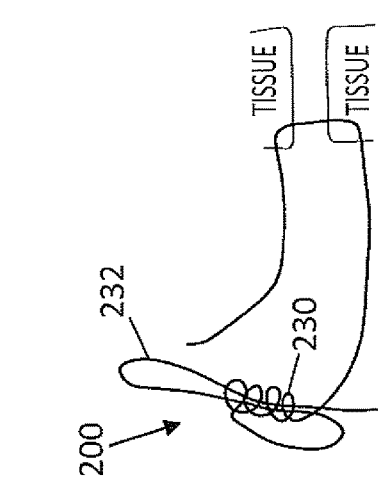
FIG. 16 is a drawing of a second embodiment of a suture with a pre-formed knot bundle for securing tissue together.

Turning to FIG. 16, a suture having a pre-formed knot bundle 230 at a first end is shown. The preformed knot bundle 230 may also include a loop 232 at a first end of the suture. The pre-formed knot bundle 230 may be pre-loaded into a suturing device, such as a suture passer, where the pre-formed knot bundle 230 may be entirely contained within the suture or reside on the outside of the suture passer. The knot bundle 230 may be passed through tissue at a first location and a free end of the suture is passed through tissue at a second location. The free end of the suture is then able to pass through the loop 232, where the knot formed may be tightened into a final position against the tissue to complete the repair.

Figure 17:
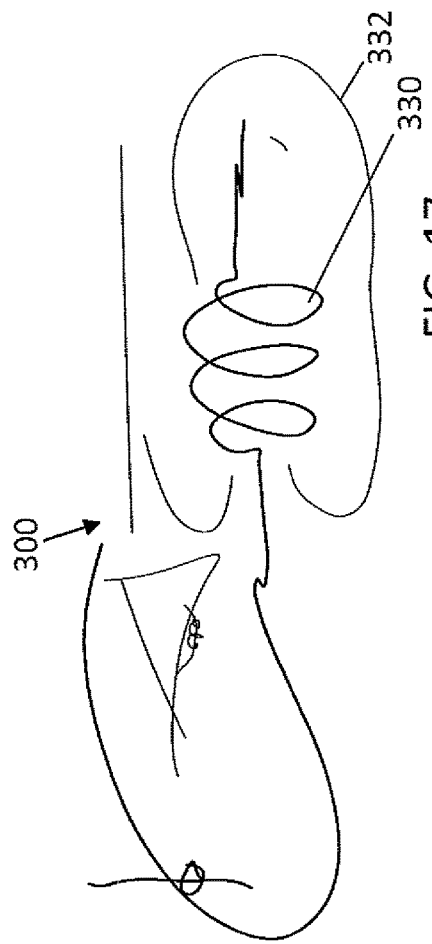
FIG. 17 is a drawing of a third embodiment of a suture with a pre-formed knot bundle for securing tissue together.

Turning to FIG. 17, a third embodiment of a knot tying device 300 is shown. In this embodiment, a pre-tied knot bundle 330 is located at a first end of the suture. The pre-tied suture may be pre-loaded into a suture device such as a suture passer. Unlike the previous embodiment, the pre-tied knot bundle 330 is not passed through the tissue. A long loop 332 that extends from the knot bundle 330 may be passed through the tissue at a first location, and a second send of the suture is passed through the tissue at a second location. The second end of the suture may then be passed through the loop 332 and the loop 332 is then used to pull the second end of the suture through the tissue and into the knot bundle 330. The knot coupling the knot bundle 330 and the second end of the suture is then tightened into a final position to complete the repair. In other examples, the pre-tied knot bundle may include loose loops of suture that can facilitate the insertion of the second end of the suture (the free end of the suture) into the pre-tied knot bundle.

Figure 18:
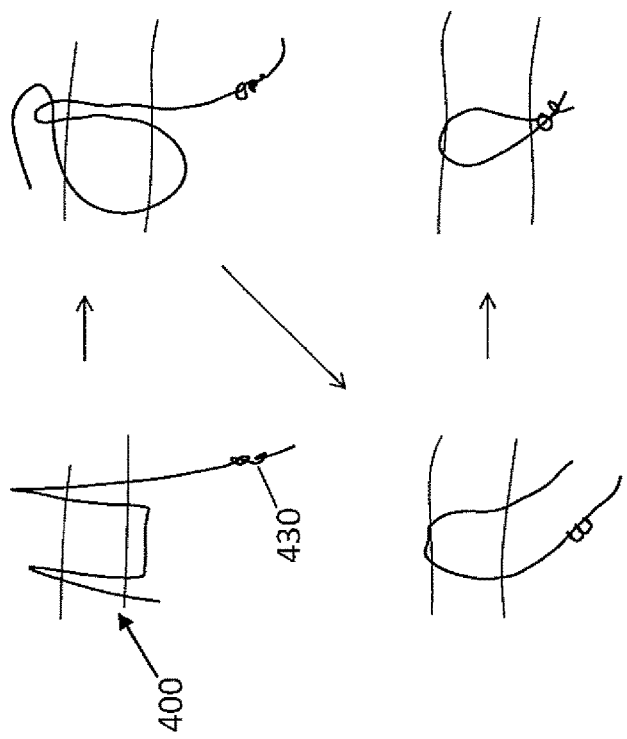
FIG. 18 is a drawing of a fourth embodiment of a suture with a pre-formed knot bundle for securing tissue together.

FIG. 18 shows a fourth embodiment of a knot tying device 400 having a suture with a pre-tied knot bundle 430 at a first end of the suture. The pre-tied knot bundle 430 may also be pre-loaded into a suture device such as a suture passer. Similar to the previous embodiment, the pre-tied knot bundle 430 is not passed through the tissue. A bight of suture adjacent to the pre-tied knot bundle 430 is passed through tissue at a first location and the free, second end of the suture is passed through tissue at a second location. The pre-tied knot bundle 430 is then passed through the bight of suture and the bight of suture is then used to pull the free, second end of the suture through the tissue. The free, second end of the suture is then passed through the pre-tied knot bundle to form a completed knot, and the completed knot can then be tightened into its final position to complete the repair.

Figure 19:
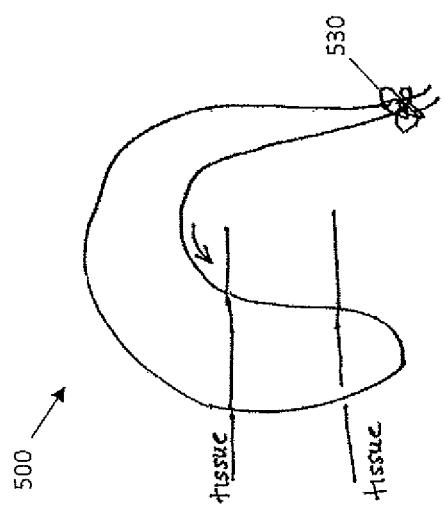
FIG. 19 is a drawing of a fifth embodiment of a suture with a pre-formed knot bundle for securing tissue together.

FIG. 19 shows a fifth embodiment of a knot tying device 500 having a pre-tied knot bundle 530 disposed on a first end of a suture. In this embodiment, the pre-tied knot bundle 530 is intended to be part of a suture subassembly. This suture assembly may be shuttled into the tissue where this is accomplished by using a first suture that has already been passed through tissue to shuttle the suture subassembly through tissue, exchanging the first suture for the suture subassembly. A free, second end of the suture subassembly may then be passed through the pre-tied knot bundle, and the suture subassembly can be shuttled through the tissue and through the pre-tied knot bundle in a single operation. The completed knot is then tightened into its final position to complete the repair.

Figure 20:
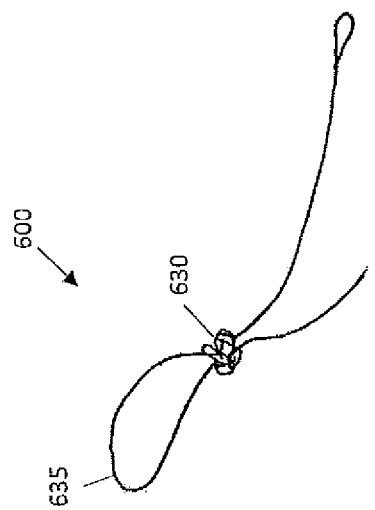
FIG. 20 is a drawing of a sixth embodiment having a sliding knot that is formed with a snare incorporated into a pre-formed knot bundle.

In yet another variation of some of the previous embodiments, a suture includes a pre-tied knot bundle disposed at a first end of the suture that can be part of a suture subassembly. In this embodiment, the suture subassembly may be contained within a knot pusher. The suture contained in the knot pusher is configured such that when a free, second end of the suture is shuttled through the tissue and back through the pre-tied knot bundle, the suture is already conveniently loaded with the completed knot at the end of the knot pusher. This embodiment would not require the additional steps of leading the suture by hand into the knot pusher FIG. 20 shows a sixth embodiment of a knot tying accessory 600. This embodiment includes a sliding knot 634 that is formed with a snare 635 incorporated into a pre-formed knot bundle 630. In some examples, the complete knot may be provided in a pre-tied configuration or it may be formed through an accessory device. The complete knot would first slide down a post-tissue leg of the suture. The post-tissue leg may then be inserted into a snare and pull through the knot, forming a convoluted pathway of the post-tissue leg through the knot. This configuration provides a more secure knot that would not slide as easily as the original knot.

FIGS. 21A-21I shows a seventh embodiment shows a cartridge containing a suture having a snare in a loose knot configuration that is attached around a knot pusher. Once the suture has been passed through tissue, a first end of the suture is loaded into an open end of the snare in the cartridge. The snare may then be pulled to form the suture into a loose sliding knot configuration. A second end of the suture is then loaded into the knot pusher to form a post-tissue leg of the suture. The loose knot configuration bundle is then released from the cartridge and transferred over the post-tissue leg of the suture, where it is then slid down into a final position and tightened to complete the repair knot.

Figure 21C:
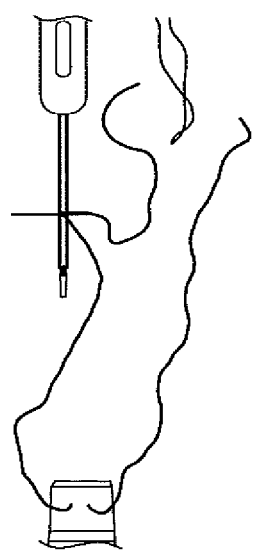
FIGS. 21A-21J are photos showing a seventh embodiment having a cartridge containing a suture having a snare in a loose knot configuration that is attached around a knot pusher or a suture passer.
Figure 21F:
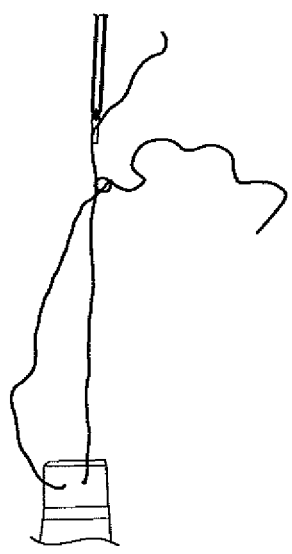
Figure 21B:
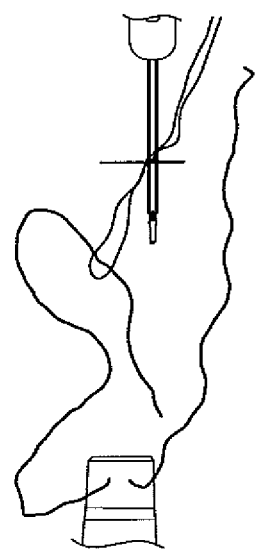
Figure 21E:
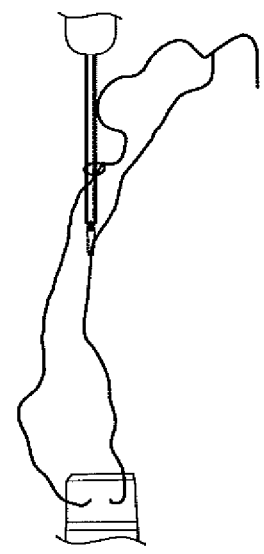
Figure 21A:
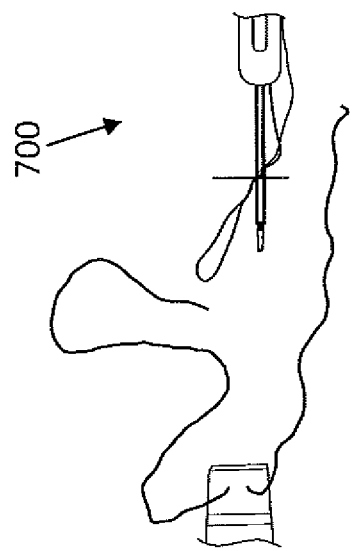
Figure 21D:
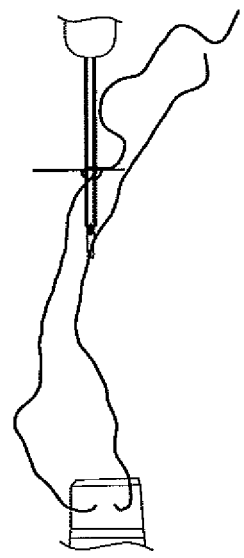
Figure 21H:
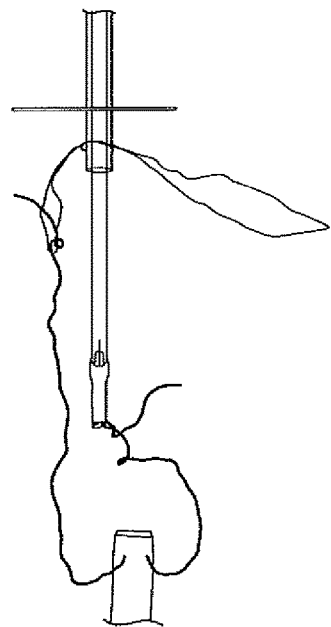

In a variation of the previous embodiment, the knot tying accessory includes a cartridge containing a snare in a loose knot configuration that is wound around a suture passer (FIG. 21H). Once the ends of a suture have passed through tissue and captured within the jaws of the suture passer, a first end of the suture is removed from the suture passer jaw and is then loaded into the open end of the snare in the cartridge. The snare is then pulled to form the first suture end into a loose sliding knot configuration. The loose knot configuration is then released from the cartridge and transferred over the second end of the suture that remains attached to the suture passer jaw. The complete knot is then slid down into its final position and tightened to complete the repair loop.

Figure 21J:
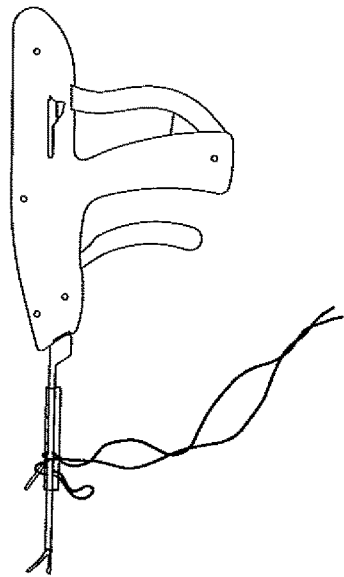
Figure 21G:
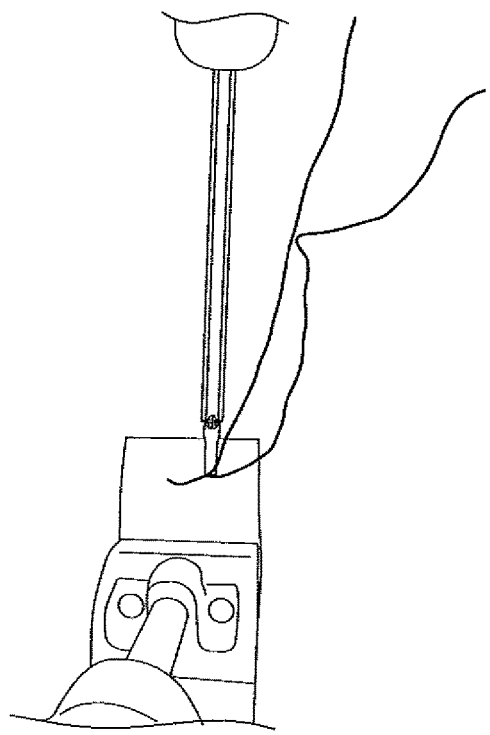
Figure 21I:
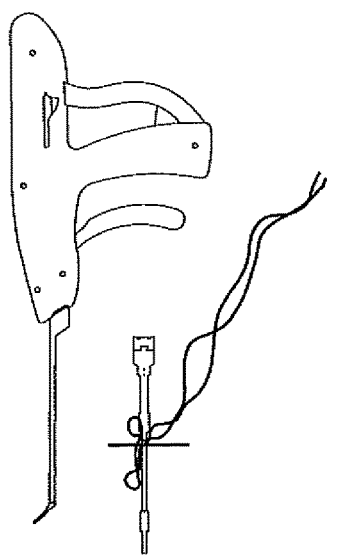

In yet another variation of a previous embodiment, the knot tying accessory includes a cartridge that is designed with components to pass a preloaded suture (FIGS. 21I and 21J). Also included are components to facilitate forming a knot into a loose sliding knot configuration, such as a snare. The cartridge may be loaded into a suture passer handle. Both ends of the preloaded suture may be delivered through tissue and captured by a suture passer jaw. A first end of the suture can be removed from the suture passer jaw and loaded into a receiving component in the cartridge, such as an open snare. The first end of the suture is the pulled via the components into a loose sliding knot configuration. The loose knot configuration is then released from the cartridge and transferred over the second end of the suture remaining attached to the suture passer jaw. By pulling back on the suture passer handle, the remaining second end of the suture is deployed from the cartridge and the complete knot is slid down into its final position to complete the repair loop.

Figure 22:
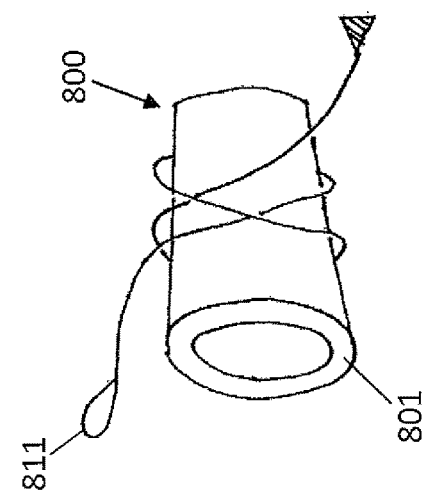
FIG. 22 is a drawing of an eighth embodiment of the knot tying accessory having a tubular-shaped device body 801 having a snare 811 wound around it in a knot bundle configuration.

An eight embodiment of the knot tying device 800 (FIG. 22) includes a tubular-shaped device body 801 having a snare 811 wound around it in a knot bundle configuration. After the suture is laced into place, a first suture end is loaded into the receiving/open part of the snare 811, and when the snare 811 is pulled, the first suture end is pulled into the loose sliding knot configuration. The second end of the suture is threaded through the device body 801 and becomes a stem for the knot. Pulling the stem pulls the loose knot bundle off the device body and creates a sliding knot on the stem. In some examples, the device body is tapered, which aids in having uniform tightening of the knot bundle. In other examples, the device body may be collapsible allowing the knot to be easily pulled off. In yet another example, the device body includes pins or other forms of protrusions that are able to separate different portions of the snare winding elements. This layout allows for the formation of a knot through discrete phases (i.e. for a Revo knot, an underhand hitch, followed by another underhand hitch, followed by an overhand hitch).

Figure 23:
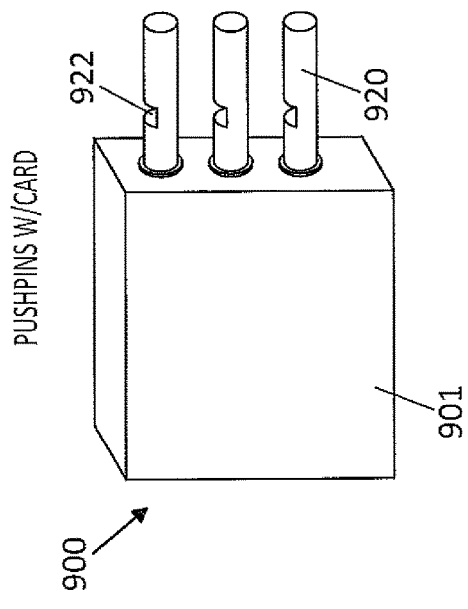
FIG. 23 is a drawing of a ninth embodiment of the knot tying accessory in the shape of a card deck including a series of pushpins.

A ninth embodiment of the knot tying device 900 (FIG. 23) includes a device body 901 that is in the shape of a card deck. The device body 901 includes a series of pushpins 920 each having notches 922 for forming a completed knot. A bight of suture is placed in the appropriate notches 922 of each pushpin 920 and with the aid of internal components, by pushing the pushpins 920 in a particular sequence forms a knot with the desired configuration.

Figure 24:
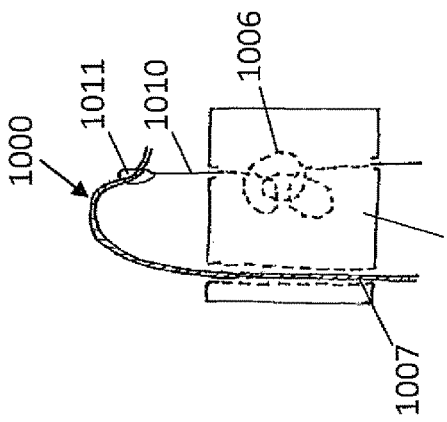
FIG. 24 is a drawing of a tenth embodiment of the knot tying accessory in the shape of a card deck and including snares and guides for creating a knot.

A tenth embodiment of the knot tying device 1000 is shown in FIG. 24. Here, the device body 1001 is in the shape of a card deck. Device 1000 includes snare 1011 wound around guides 1106. The guides may be channels (as shown) or post/protrusions within the device body for guiding a guide thread 1010. A first suture end is snared through the device body 1001. In the example where only one snare is present, the second suture end is inserted through a channel 1107 in the device body 1001. The completed knot can then be released by opening or breaking apart the card-shaped device body 1001. In some examples, portions of the device body can be constructed from a foam material such that the knot can be pulled to release from the card-shaped device body. In other examples, the card-shaped device body may include two halves coupled wherein the completed knot may be released by unfolding the card. The two halves of the device body may have a hinged arrangement or may be slidingly coupled.

Figure 25B:
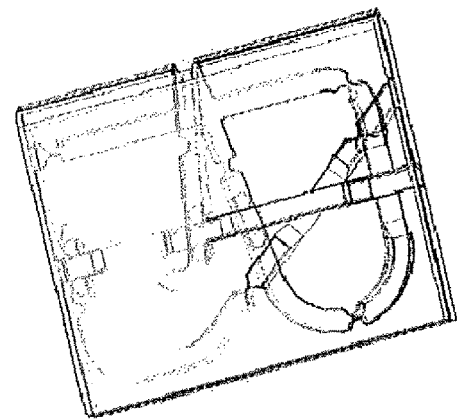
FIGS. 25A and 25B are drawings of an eleventh embodiment of the knot tying accessory having internal pathways disposed on an upper and a lower portion of a device body for forming a knot pattern.
Figure 25A:
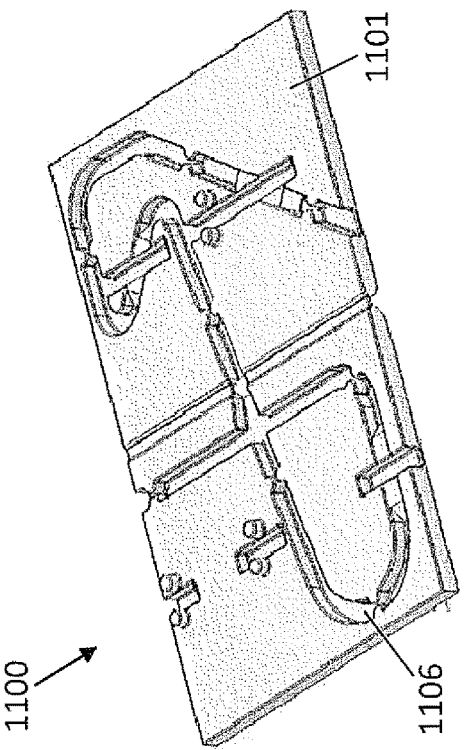

Turning to FIGS. 25A and 25B, an eleventh embodiment of the knot tying device 1100 is shown. In this embodiment, the device body 1101 also has a rectangular form. No capture loop is used. The user opens the device body (the open device body is shown in FIG. 25A). The user then lays a first end of the suture into the appropriate interior pathways 1106. The internal pathways may be channels or may be posts or other suitable element for retaining a bight of thread. Note that the device body is divided into an upper portion and a lower portion where the pathways of the upper portion is not necessarily the same as that for the lower portion. As before, there may be instructions imprinted on the actual device or there may be separate instructions for how to place a guide thread within the interior pathway 1106 of device 1100. The user then closes the device and inserts a second end of the suture the internal pathway 1106 (channels in the case), where the channels have the appropriate lead-ins to aid the second end of the suture cross under and/or over the first end of the suture. Once the second end of the suture has exited the device 1100, the device 1100 may be opened to release the formed knot.

Figure 26:
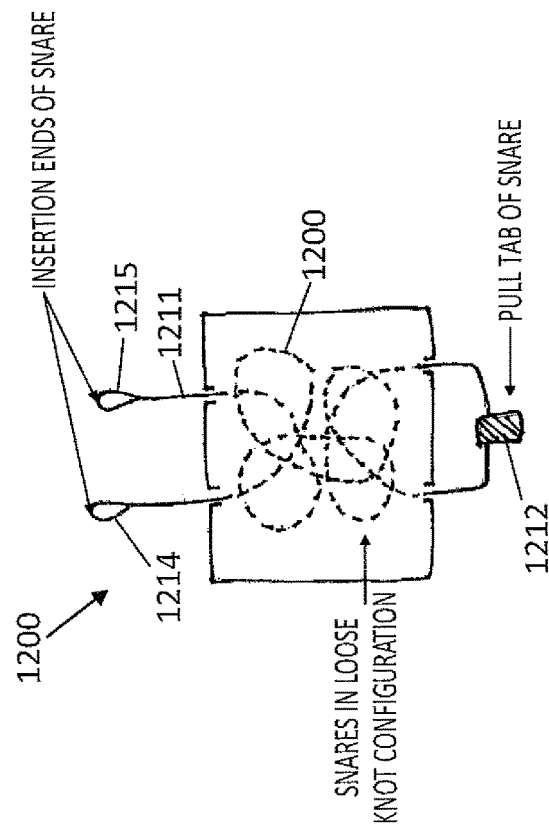
FIG. 26 is a drawing show a twelfth embodiment of the knot tying accessory having a snare, a first and a second insertion end, and a pull tab.

A twelfth embodiment of the knot tying device 1200 is shown in FIG. 26. Device 1200 includes one single length snare 1211 having a first and a second insertion end 1214 and 1215 and a pull tab 1212. The two legs of snare 1211 may form a loose knot configuration from being threaded through an interior pathway 1206. Snares 1214 and 1215 are able to couple with a first and a second end of a suture and the loose knot configuration may be transferred to the suture when the first and the second of the suture are pulled through a device body 1201 using the pull tab 1212.

Figure 27:
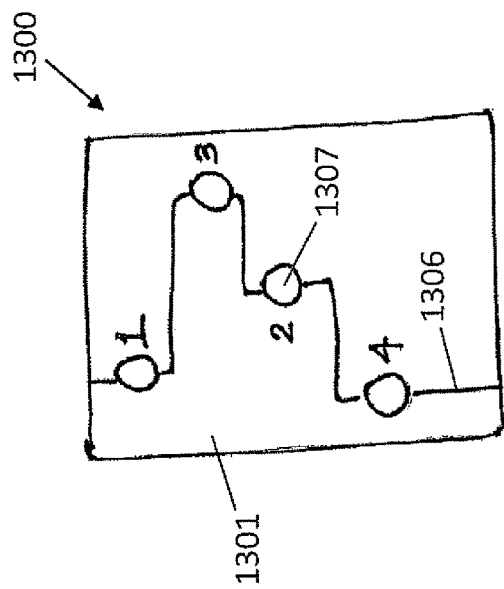
FIG. 27 is a drawing show a thirteenth embodiment of the knot tying accessory having a series of apertures 1307 that are connected with interior pathways.

A thirteenth embodiment of the knot tying device 1300 is shown in FIG. 27. Device 1300 also include a device body 1301 in the shape of a card deck. Device 1300 also includes a series of apertures 1307 that are connected with interior pathways 1306. Simple instructions may be provided to a user for inserting the suture through the apertures 1307 in a sequence that result in a desired knot formation. The device body 1301 may then be open or broken apart to release a completed knot.

In a variation on the previous embodiments of the knot tying device having an interior pathway, this embodiment includes a straight channel for insertion of a post-tissue suture end and instructions for a sequence of winding to form a sliding knot (e.g. a taut line hitch formed by wrapping twice around a distal portion of a tool and once around a proximal end of the tool). The card-shaped device body also includes cleats for holding the two regions of the knot separate to aid in winding the desired pattern.

Figure 28:
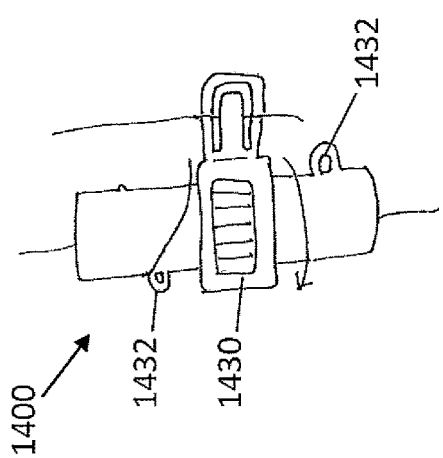
FIG. 28 is a drawing show a fourteenth embodiment of the knot tying accessory having a rotating piece and positioning aides for a winding tool to wind a suture into a correct knot pattern.

In yet another variation of the knot tying accessory device 1400, the device body may include a rotating piece 1430 and positioning aides 1432 for a winding tool to wind a suture into a correct knot configuration (FIG. 28). In some examples, a first end of a suture is secured to a carriage. The carriage is rotated and translated on the tube to tie the suture tail. The post-tissue second of the suture is inserted in the tube and the knot is slid off the tube onto the post.

Figure 29:
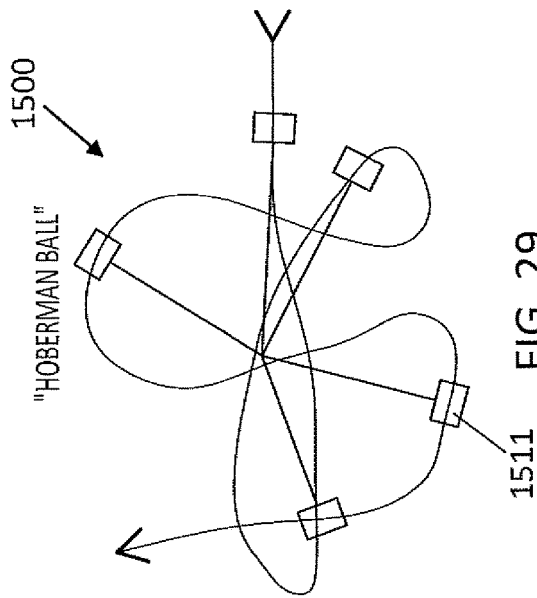
FIG. 29 is a drawing show a fifteenth embodiment of the knot tying accessory having a 3D geometric shape.

In yet another variation of the knot tying accessory device, a 3D geometric shape like a Hoberman Ball to move suture ends (placed into parts of the ball and being held by couplers 1511 when the ball is in its expanded configuration) into a knot configuration (created by collapsing the ball inwards) FIG. 29.

Figure 30B:
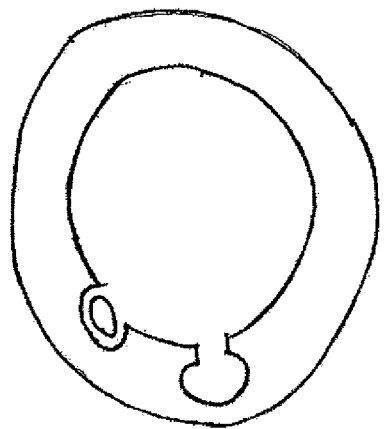
FIGS. 30A and 30B are drawings show a sixteenth embodiment of the knot tying accessory having cam paths that a ball bearing can follow.
Figure 30A:
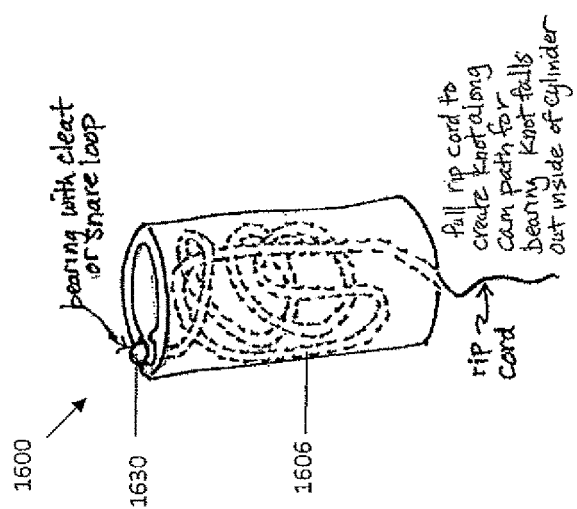

In yet another variation of the knot tying accessory device, a concept of cam paths 1606 that a ball bearing 1630 follows is shown in FIGS. 30A and 30B. The ball bearing has a cleat or snare loop 1611 to hold onto a suture end. A cord is attached to the bearing such that when it is pulled, the ball bearing attached to the suture follows the path to tie a knot. The suture can then drop to the interior of the cylinder and the knot is released. The cam path can move radially, circumferentially, and axially to form complex knot patterns with overlapping sections. A variation of the previous embodiment is shown in FIGS. 30A and 30B where cam paths with a cleat that spins along and up the cam path to wrap the suture around the post strand. At the end, the cam springs back down with one half spin to complete SMC knot. A possible cleat shape is shown in FIG. 30B.

Figure 31B:
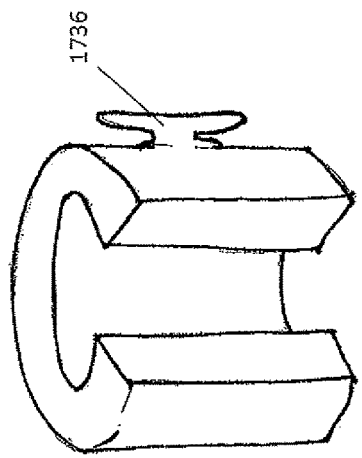
FIGS. 31A and 31B are drawings of a variation of the sixteenth embodiment where the cam paths include a cleat or cleats.
Figure 31A:
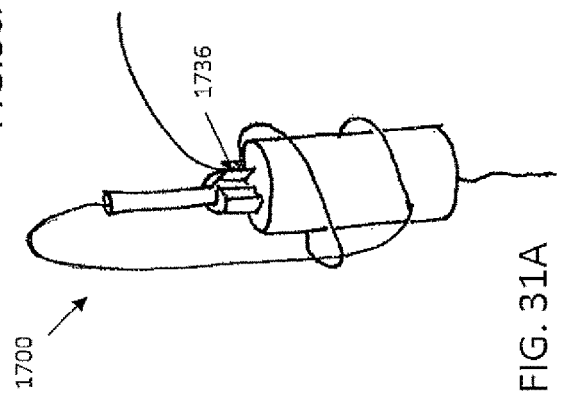

Another variation of the knot tying accessory device is shown in FIGS. 31A and 31B. In this variation on the embodiment directly before, the cam paths includes a cleat 1736 that spins along and up the cam path to wrap the suture around the post strand. At the end, the cam springs back down with one half spin to complete SMC knot. A possible cleat shape is shown in FIG. 31B.

Also disclosed are concepts for a tool for quickly forming half-hitches in a suture (FIG. 32). The tool has a long body and a hook 1836 at one end. The suture is wrapped around the shaft of the tool, and then the hook is used to pull the suture through the wrap, forming a half hitch. The shaft of the tool has a greater diameter than that of the hook.

Also disclosed herein are concepts for tying a stronger knot (FIG. 33). The concept below shows a knot pusher that forms and tightens square knots at the repair site. The knot pusher (shown in green below) has pairs of snares at the distal end, and the suture ends would be snared in and pulled tightly in directions perpendicular to the axis of the knot pusher to create levels of a square knot (shown in orange). A first set of snares may be nested into a second set of snares, so that the first set of snares may be pulled to form the first level of the knot, then pull the suture into the second set of snares. The second set of snares can then be pulled to form the second level of the knot. Further nested sets of snares may be used to form an arbitrary number of levels of the knot to increase the knot strength. A variation of the previous concept creates half hitches at the end of the knot pusher, which then facilitates tightening those half hitches. This might be accomplished by a different configuration of snares. This may also be accomplished by a rotating member of the knot pusher that forms a suture line into a half hitch pattern.

The following knot tying accessory devices are implantable devices. FIG. 34 shows one example of such a device. Here, a short tube or sleeve implant 2001 that would be crimped closed around the suture ends having a holder 2011. One embodiment is a metal sleeve that is overmolded with plastic to soften the contact surfaces and prevent chondral tissue damage. The sleeve could also be sized to remove twists from the sutures to increase the holding strength.

Another embodiment of an implantable knot tying accessory is shown in FIG. 35. Here, a suture that is slid through an implantable sleeve 2120, and then a plug 2122 is pressed into the sleeve to trap the suture in place. Pressing the two portions together may be accomplished by an accessory device. In some examples, an implantable clip that squeezes shut to hold the suture ends and close the repair loop. In other examples, an implantable clip that squeezes shut to hold the suture ends and close the repair loop. In yet other examples, an implantable rotating clasp holds the suture ends in place. Initially, the top and bottom pieces of the clasp are aligned so that there is a straight lumen through which the sutures can slide. Once the repair is appropriately tensioned, the one of the ends of the clasp is rotated so that the suture pathway becomes tortuous and small, thus holding the suture in place. In other examples, the implantable accessory is a clip that snaps shut to hold the suture ends to close the repair loop.

Figure 36D:
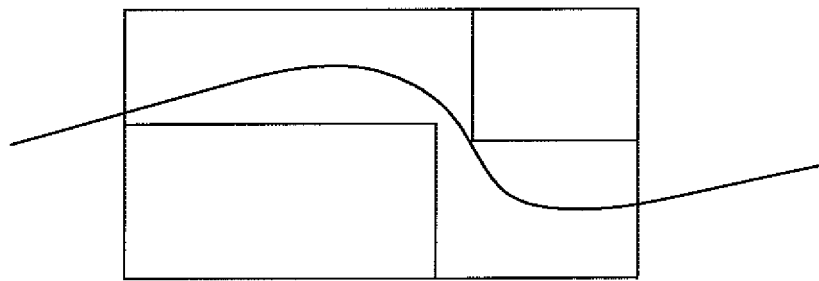
FIGS. 36A-36D is a drawing showing another embodiment of an implantable knot tying accessory device having a rotatable clasp.
Figures 36B, 36C:
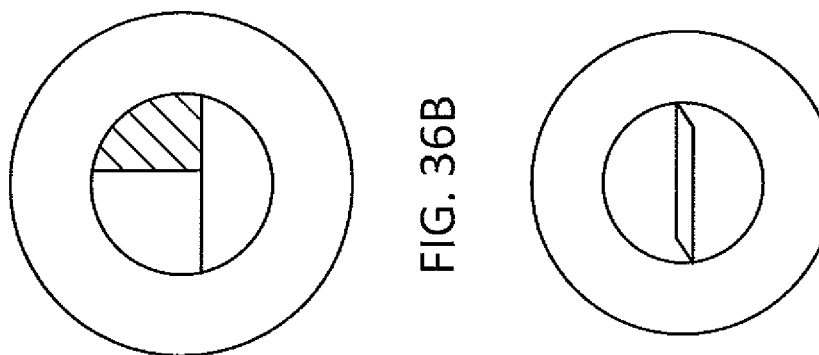
Figure 36A:
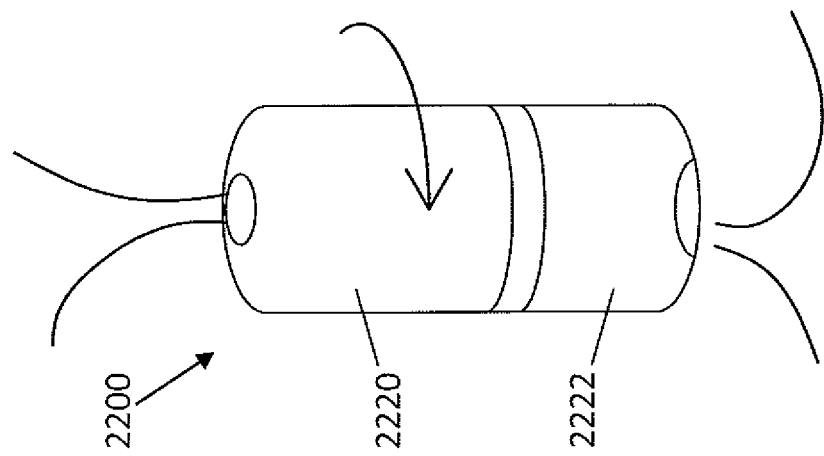

In yet other examples, the implantable accessory 2200 is an implantable clasp that is able to hold suture ends in place (FIGS. 36A-36C). In a first position, a top piece 2220 and a bottom piece 2222 of the clasp are aligned so that there is a straight channel through which a suture can slide. Once the repair is appropriately tensioned, one end of the clasp may be rotated so that the suture pathway become tortuous and small, thus holding the suture in place.

Another embodiment of an implantable knot tying accessory 2300 is shown in FIG. 37. An implantable toggle 2324 has a configuration where the suture slides easily through it, and a second where the suture is held in place. The mechanism could be similar to the toggles on drawstrings on clothing, where pushing a button aligns the holes through which the suture travels. The toggle could have separate lumens each suture, or potentially a single hole for both sutures.

FIG. 38 shows a structure for bringing together and maintaining tissue. This embodiment includes a one-way sliding mechanism 2426 like a zip tie to hold the meniscus together. One embodiment of this concept uses an implantable, non-suture based material to form a holder 2427 portion of the zip tie. Another embodiment uses barbed suture as the incremental teeth of the zip tie. Another embodiment uses a series of knots tied into a suture line as the incremental teeth of the zip tie. Yet another embodiment of the holder is the existing suture line, which the barbed suture or knots is pierced through to keep in place.

Another concept for bringing together and maintaining tissue is a suture with knots 2500, wherein the suture can also be passed through a loop 2511 formed from the suture (FIG. 39). Once the repair is tight, the loop would automatically be pulled tight and shut, keeping the suture knot from pulling out. A variation of this idea uses a loop formed from dividing the width of the suture in two. Such a loop could be anywhere on the suture length (FIG. 40), not only at the end of the suture. The appropriate suture knot/ball is passed through the loop to hold the repair closed. The suture line with knots can also be slid through a pre-tied, sliding knot construct such as a girth hitch. When the repair was appropriately tensioned, the free leg of the knot construct is pulled to cinch down on the suture, and the suture knots keep that line from sliding backwards (FIGS. 41A and 41B).

Figure 42:
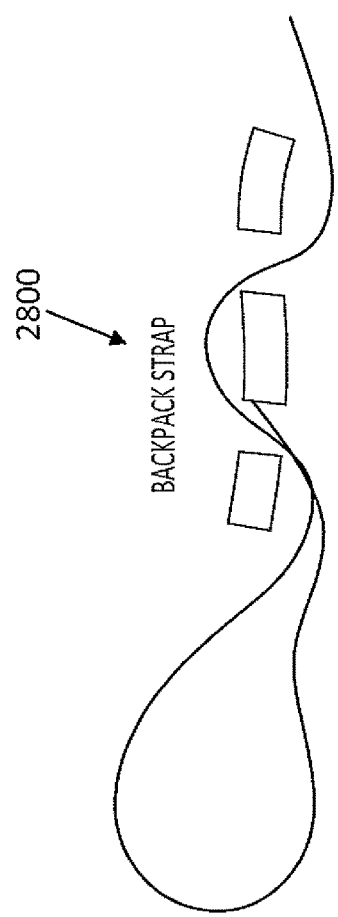
FIG. 42 is a drawing of another embodiment of the knot accessory showing an implant similar to a backpack strap.

Another embodiment of the knot accessory 2800 is shown in FIG. 42. shows an implant similar to a backpack strap, which uses a tortuous path and material shaping so that it is easy to pull the suture through in one direction but difficult in the reverse direction.

Figure 43:
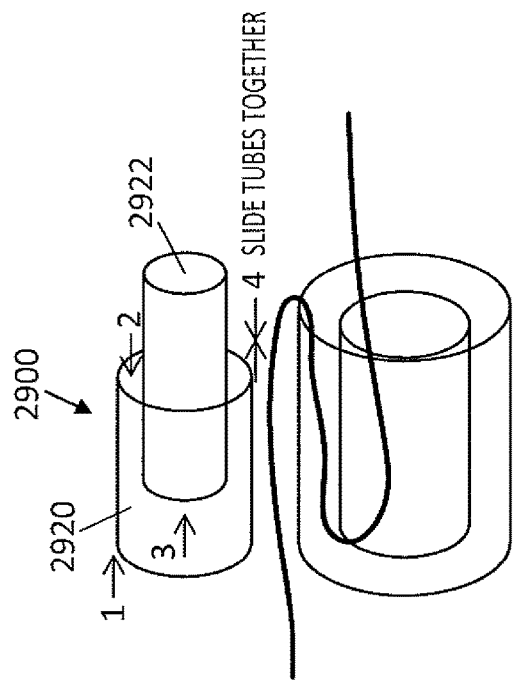
FIG. 43 is a drawing of another embodiment of the knot accessory with a tubular construction having an inner 28 is a drawing of another embodiment of the knot accessory showing an inner and an outer tube.

Another embodiment of the knot accessory 2900 is shown in FIG. 43. This device includes an outer tube 2920 and an inner tube 2922 that are initially in an open configuration allowing the sutures to easily slide through. To secure the suture in place, the tubes are slid and held together, creating a tortuous path for the suture and preventing them from sliding further.

Figure 44:
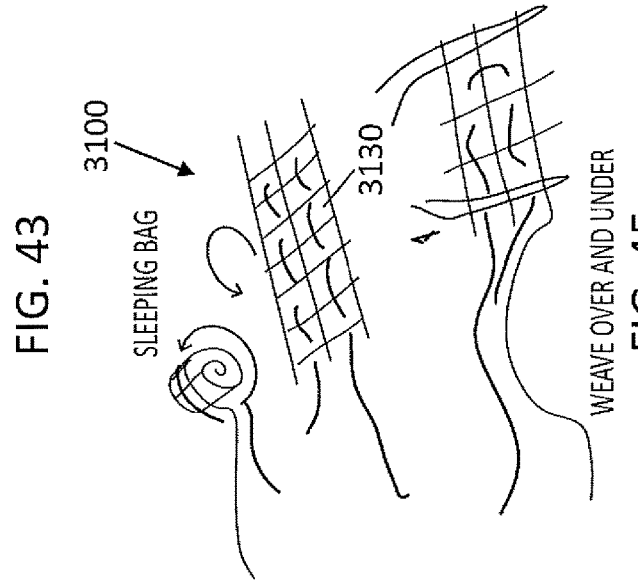
FIG. 44 a drawing of another embodiment of the knot accessory showing a suture bight through a hole in an implant.

Another embodiment of the knot accessory is shown in FIG. 44. Here a suture bight through a hole 3020 in an implant 3022. The ends of the suture are passed through the suture bight, and the loop construct is tightened.

Figure 45:
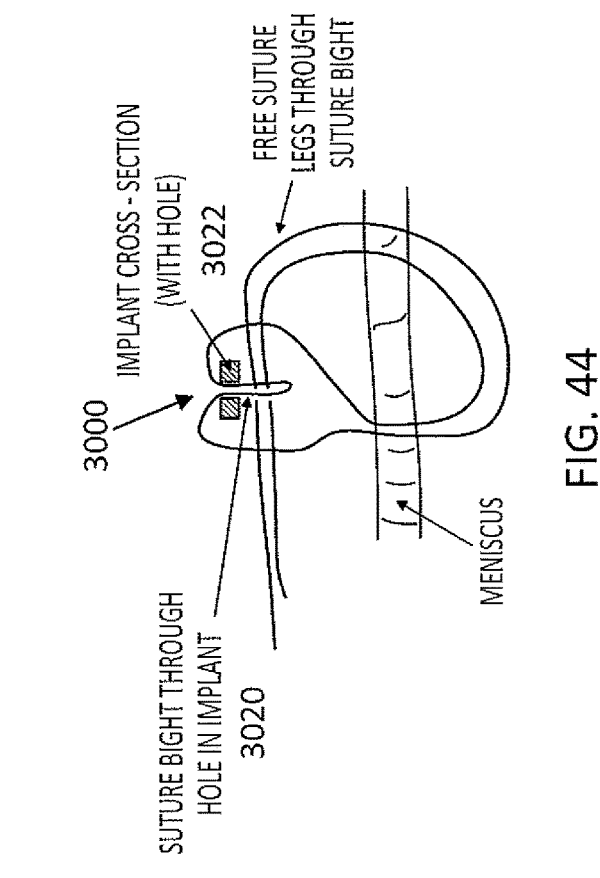
FIG. 45 is a drawing of another embodiment of the knot accessory showing a mesh/grid material through which the suture is woven for maintaining the suture.
Figure 46A:
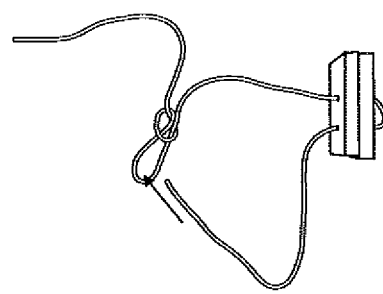
FIGS. 46A-46E illustrate another example of a knot that may be used as described herein.
Figure 46B:
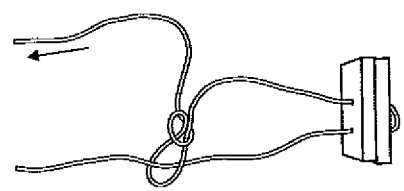
Figure 46C:
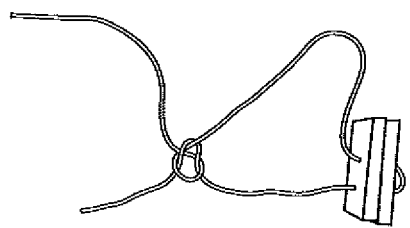
Figure 46D:
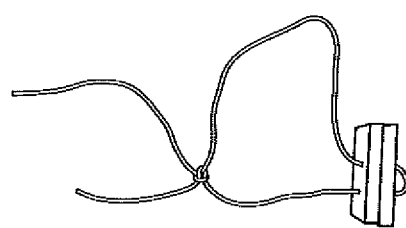
Figure 46E:
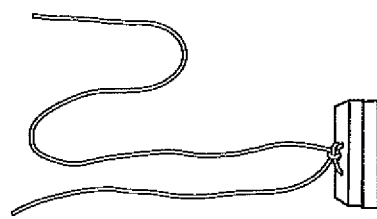
Figure 47A:
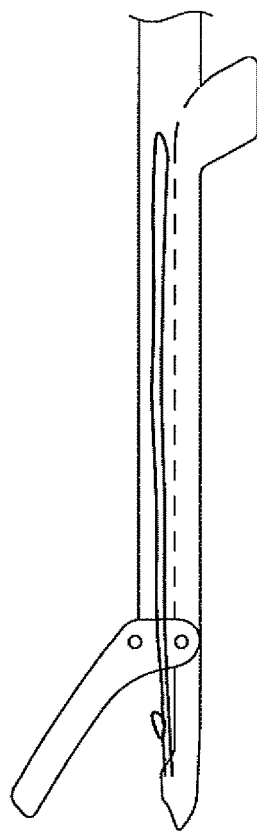
FIGS. 47A-47D illustrate a cartridge pre-loaded with a knot as described herein. The knot is passed as the suture end is passed, in FIG. 47B, and a second length of suture is passed through the tissue (triangular region) in FIG. 47C.
Figure 47B:
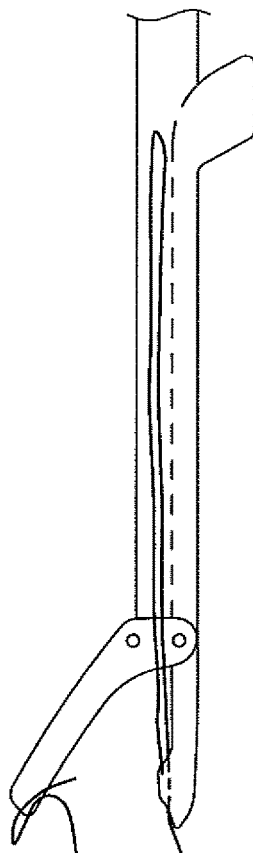
Figure 47C:
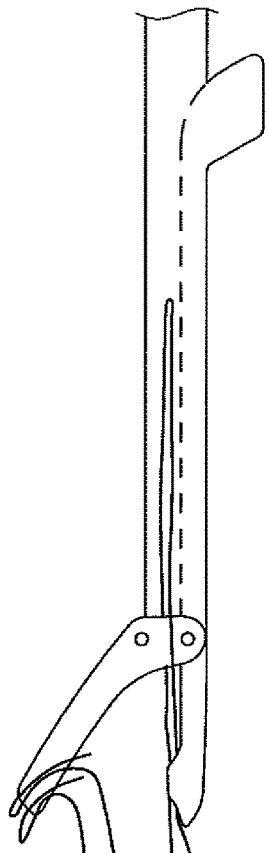
Figure 47D:

Another embodiment of the knot accessory 3100 is shown in FIG. 45. Here, adhesive are used to bond the suture lines together, or to bond a suture knot. One version uses an adhesive activated by aqueous solution. One version delivers the adhesive from an accessory device at the repair site, and another version delivers the adhesive through a knot pusher. The suture can also be welded together. Methods exist currently to weld the suture ultrasonically. The welding could be facilitated at the end of a knot pusher/knot cutter device. In FIG. 45, a mesh/grid material 3130 through which the suture is woven. The suture can slide easily through the mesh to tighten the repair, until the mesh is tightened, folded, and/or rolled up. In one variation, the mesh starts attached to one end of the suture (see bottom picture below). In another variation, the mesh is a separate piece through which both suture ends are woven after stitch delivery through the meniscus.

Another concept described herein is the idea of a doubled-back suture. A doubled-back suture in the repair to create a stronger knot. The doubled-back suture could be achieved by shuttling in the bight of suture. Alternately, the doubled-back suture could be created by passing a bight of suture on one needle fire, and passing both free ends of suture on the other fire. Another variation uses a knot configuration that is not traditionally considered a sliding knot using lubricious suture that enables the knot to be slid. This can result in a more secure knot in the lubricious suture than would be possible using a traditional sliding knot. This style of knot may be formed by a cartridge or accessory device as detailed above. The knot may also be formed at the end of a knot pusher for convenient repair completion. Another variation forms a non-sliding knot around the tip of a knot delivery device (for example, a knot pusher) such that it is held in an open and sliding configuration. The knot is then delivered to the repair and released from the knot delivery device, allowing the knot to be tightened into a non-sliding configuration to complete the repair loop. One embodiment is a cartridge that attached to the knot delivery device. Another embodiment is a separate accessory device that does not attach to the knot delivery device. Another embodiment is a knot delivery device with built-in knot-forming functionality.

In suture-based repair of soft tissue, after suture is passed through tissue, a knot is typically used to join both ends of the suture to create a suture loop. The resultant knot is then cinched to the repair site and tightened to approximate tissue and complete the repair. The following disclosure illustrates suture that is preloaded in a suture passer and configured with a knot prior to use.

FIGS. 46A-46E represent an example of a suture (shown with rope for easier visualization) with a pre-formed knot bundle at one end. The knot bundle is passed through the tissue at one location, and the knot-free end of the suture is passed through the tissue at another location. The knot-free end is then passed through one or more loops formed by the pre-tied knot. The suture is tensioned and the knot is dressed to join the two ends of the suture. The knot is tightened to its final position to complete the repair.

FIGS. 47A-47D show a suture with a pre-tied knot (such as the one described above) positioned/assembled on top of the cartridge. The pre-tied knot may be positioned near the distal end of the lower jaw so that the pre-tied knot can pass more easily out of the cartridge. After the suture ends are passed through tissue, the device is retracted and the suture is released from the cartridge.

Figure 48C:
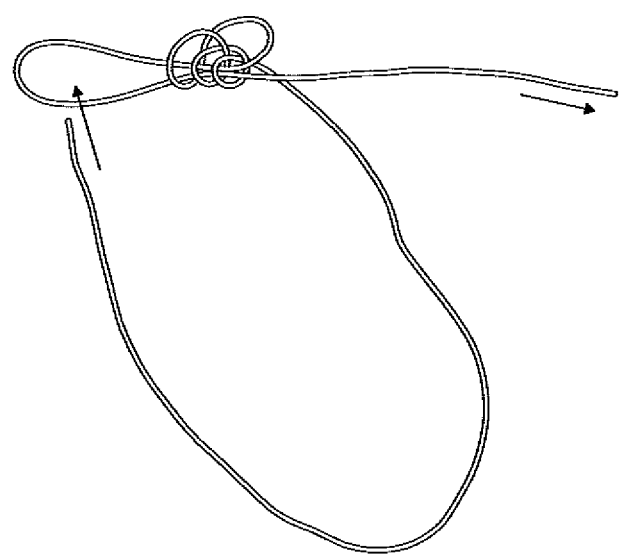
FIGS. 48A-48C illustrates another variation of a suture knot that may be used as described herein.
Figure 48B:
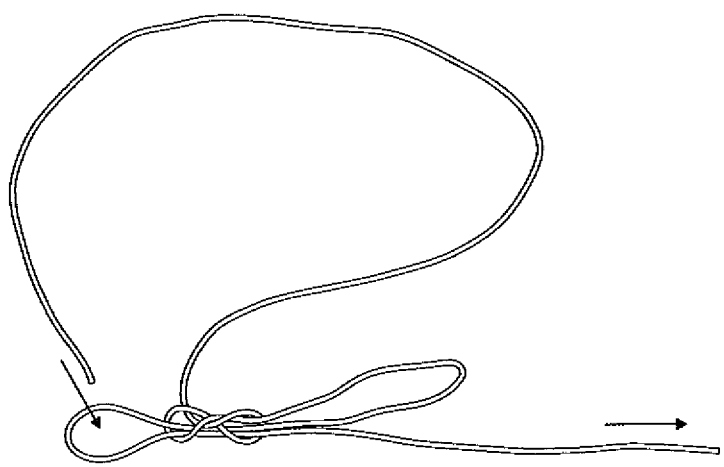
Figure 48A:
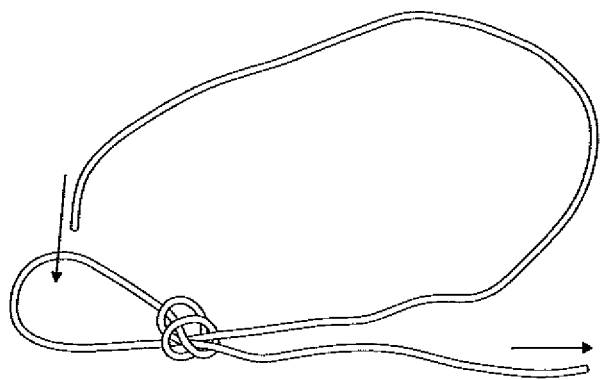
Figure 49A:
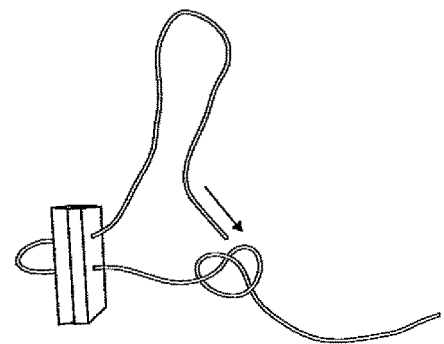
FIGS. 49A-49G illustrate the operation of a suture with a pre-formed knot bundle that may be used in any of the variations described herein.
Figure 49B:
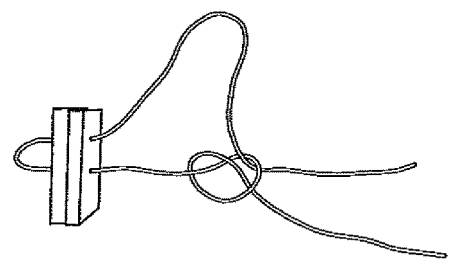
Figure 49C:
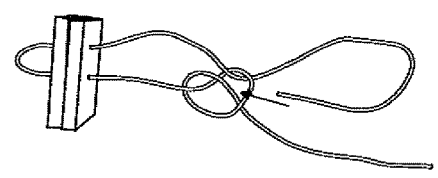
Figure 49D:
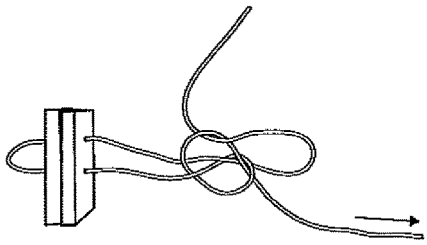
Figure 49E:
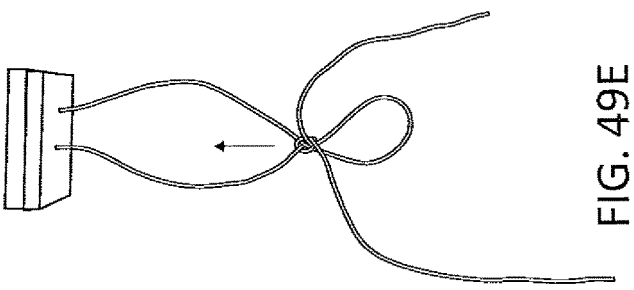
Figure 49F:
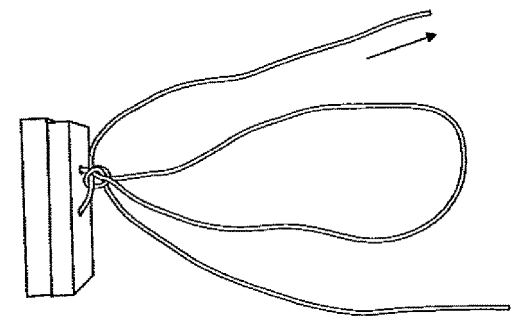
Figure 49G:
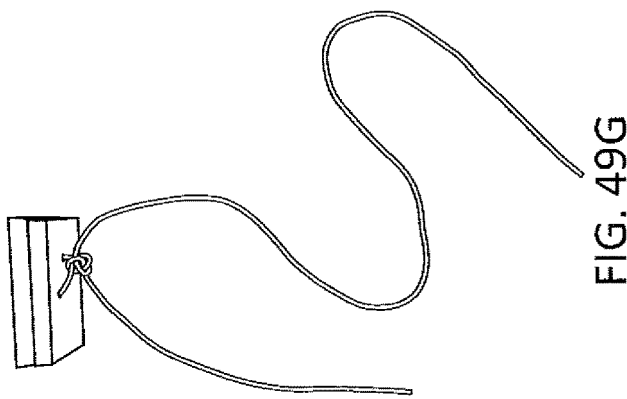
Figure 51:
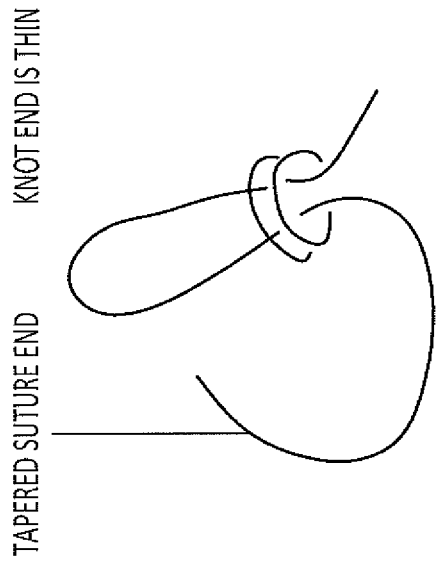

FIGS. 48A-48C show different examples of pre-formed knots with loops to join the two ends of the suture. Arrows indicate the passing of suture into one or more loops and also pulling of the suture to cinch and/or form the knot.

Similarly, FIGS. 49A-49G illustrate a suture with a pre-formed knot bundle at one end. The knot bundle is passed through the tissue at one location, and the knot-free end of the suture is passed through the tissue at another location. The knot-free end is then passed through more than one loop formed by the pre-tied knot. The knot-free end of the suture exits one loop of the knot and then enters another loop of the knot, leaving a tail and a temporary loop. The suture is tensioned and the knot is dressed to join the two ends of the suture. The knot is sent to its final position. Finally, the suture limb is tensioned to remove the temporary loop and fully secure the knot and complete the repair.

Figure 50:
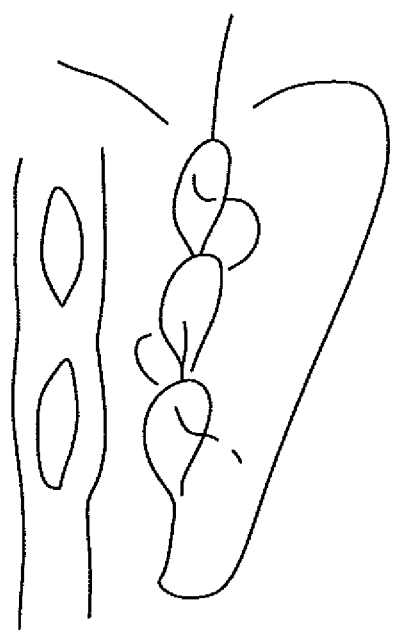
FIG. 50 shows a suture having a variety of openings at one end of the suture.

FIG. 50 shows another embodiment for joining both ends of the suture. The suture in this example may have a series of openings at one end of the suture. The other end of the suture is woven through the openings to join both ends of the suture.

Figure 51:
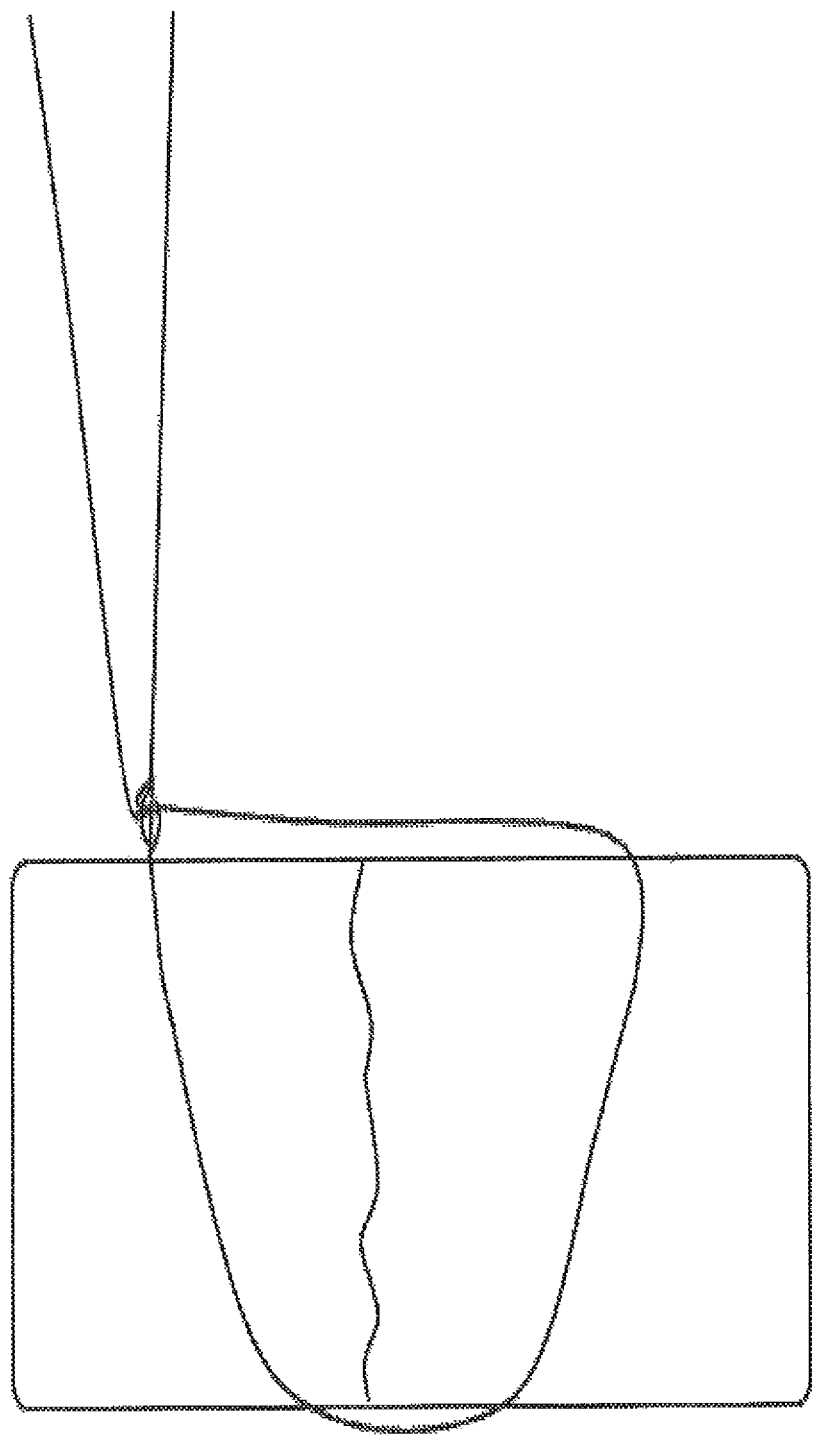
FIG. 51 sows a suture having a tapered portion where the tapered portion has a smaller diameter than the rest of the suture.

FIG. 51 shows a tapered portion of a suture where the tapered portion has a smaller diameter than the rest of the suture. The tapered portion of the suture is used to facilitate the passing of the knot-free end of the suture through the pre-tied knot when dressing the knot.

Figure 52:
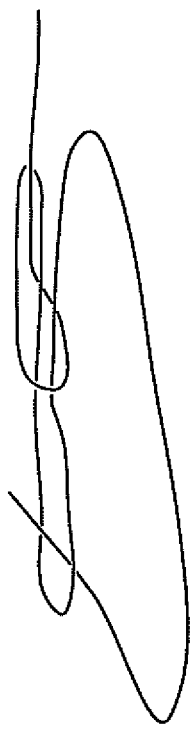
FIG. 52 is another variation of a knot that may be used.

FIG. 52 shows another embodiment to facilitate the passing of the knot-free end of the suture through the pre-tied knot when dressing the knot. The pre-tied knot configuration is kept loose/open and the shape is set through heat or other means. The knot-free is then passed easily through pre-tied knot when dressing the knot.

Figure 53A:
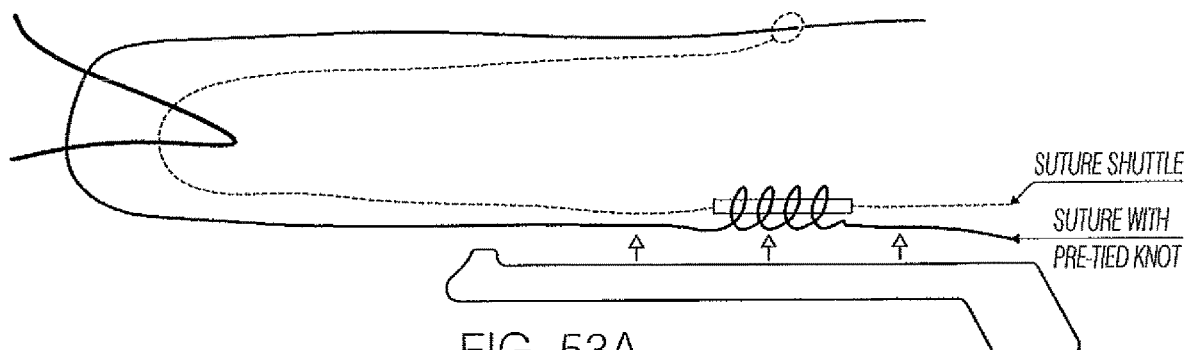
FIGS. 53A-53E illustrate a suture with a knot that is pre-tied around a separate disposable suture or other cord-like element.
Figure 53B:
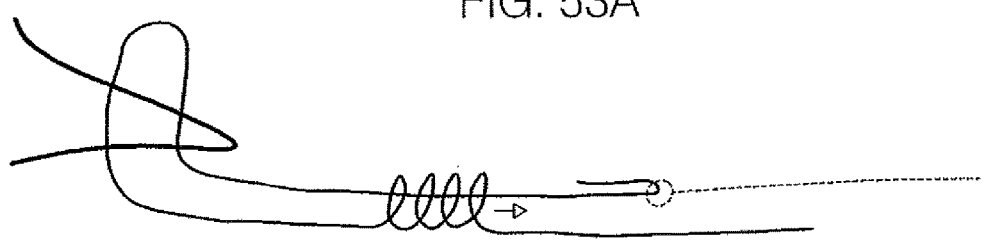
Figure 53C:
Figure 53D:
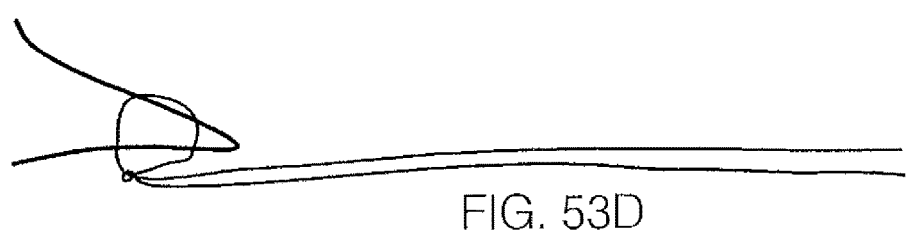
Figure 53E:

FIGS. 53A-53E illustrate a suture with a knot that is pre-tied around a separate disposable suture or other cord-like element (suture shuttle). The suture with the pre-tied knot and the suture shuttle are positioned/assembled on top of the cartridge. One end of the suture is passed through tissue at one location, and the loop end of the suture shuttle is passed through tissue at another location. The cartridge is removed from the suture passer handle and the sutures are released from the top of the cartridge. In FIG. 53B, the suture shuttle is pulled and the suture tail is passed from the top of the tissue to the bottom of the tissue and through the pre-tied knot to join both ends of the suture. In FIGS. 53C-53E the knot is dressed and sent to its final position to complete the repair.

Other variations may include substituting the suture and suture shuttle in the previous example with any of the examples of sutures with pre-tied knots described earlier.

FIG. 54 shows a suture cartridge that is loaded from the top side of the suture passer's shaft to provide additional space for any of the pre-tied knot or suture shuttle concepts described earlier. Other elements of the device such as the shaft and clamp components can be designed to occupy space lateral to the cartridge to facilitate this concept. FIG. 54 also shows a housing 5407 for the pre-tied knot that can break away or similarly detach from the cartridge to release the pre-tied knot.

In any of these variations, the knot-free of the suture may be tapered down to a smaller diameter. This reduces the space occupied by the knot-free end in the cartridge, providing more room for the pre-tied knot. Thus, any of the variations described herein may also use a suture with one end tapered down to a smaller diameter. A pre-tied knot with an open loop may be formed in the small-diameter end, resulting in a smaller pre-tied knot than is possible with the full-diameter suture. The suture ends are first passed through the tissue. Next the full-diameter, knot-free end is passed through the loop. Then the knot is flipped/dressed into a configuration that slides over the small-diameter end. The knot is then slid past the small-diameter section and to the full-diameter section. The knot is now composed of only full-diameter suture, and is tightened to its final position to complete the repair.

Other Suture Passers

FIGS. 55A-59B show variations of suture passers that may be used with the pre-tied knots and assemblies for forming them as described herein. For example, FIG. 55A-55E show a suture passer where a knot-free end of suture is initially loaded into the upper jaw, either manually or by attaching a cartridge. The first pass is completed as follows: a needle is fired through the tissue, the needle grabs the suture end from the upper jaw, the needle pulls the suture end down through the tissue, and the suture end is held in the lower jaw. For the second pass, the needle is fired again to pass the suture end up through the tissue where it is captured by the upper jaw. A pre-tied knot at the opposite end of the suture is then released from the cartridge. The knot is moved off of the suture passer and onto the knot-free suture end. The suture is tensioned and the knot is dressed to join the two ends of the suture. The knot is tightened to its final position to complete the repair.

In another embodiment, one needle retrieves the suture end and another needle passes it back to the upper jaw. In another embodiment (shown in FIG. 56), the needle retrieves a shuttle that is connected to the suture end so that the shuttle pulls the suture end into the lower jaw. For the second pass, the needle can pass either the suture end or the shuttle up through tissue where it is captured by the upper jaw.

FIGS. 57 and 58A-58B shows a suture passer that has a length of suture that is formed into a loose knot configuration and held open in the upper jaw. The ends of a separate repair suture are passed through the tissue and through the open knot, and are captured in the upper jaw. The knot suture is released from the upper jaw and the knot is tightened/dressed to secure the two ends of the repair suture. The knot is slid down the repair suture to its final position to complete the repair.

In FIGS. 59A-59B the knot suture is held in the cartridge and then released over the ends of the repair suture.

In any of the embodiments described above, a second suture may be placed about the repair suture to further maintain and hold the repair suture in place. Also, in any of the embodiments described above, the knot tying accessory can be provided for as a kit. It may also be advantageous for the kit to be sterile.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of repairing a meniscus in a knee joint, the meniscus having an apex, a superior surface adjacent a femur, and an inferior surface adjacent a tibia, the method comprising:

using a suture passer to pass a suturing element from the inferior surface of the meniscus, through the meniscus, to the superior surface of the meniscus, across the inferior surface of the meniscus, and again back through the meniscus from the inferior surface to the superior surface of the meniscus.

2. The method of claim 1, further comprising minimally invasively positioning a distal end of the suture passer near the apex of the meniscus before passing the suturing element.

3. The method of claim 1, further comprising extending a first arm of the suture passer between the superior surface of the meniscus and the femur and extending a second arm of the suture passer between the inferior surface of the meniscus and the tibia.

4. The method of claim 1, further comprising passing the suturing element radially across the inferior and superior surface of the meniscus, to form a vertical loop around the meniscus.

5. The method of claim 4 further comprising securing the vertical loop using a knot.

6. The method of claim 1, further comprising passing the suturing element laterally across the inferior and superior surface of the meniscus, to form a lateral loop around the meniscus.

7. The method of claim 6 further comprising securing the lateral loop using a knot.

8. The method of claim 1 wherein using the suture passer to pass the suturing element forms a portion of a suturing element loop around a tear in the meniscus, and wherein the method further comprises securing the sututring element loop using a knot.

9. The method of claim 8 further comprising using a knot pusher to place a knot formed by the suturing element on the superior surface to complete the suturing element loop.

10. The method of claim 1 further comprising:
extending a first arm of the suture passer into a space between the superior surface of the meniscus and the femur; extending a second arm of the suture passer into a space between the inferior surface of the meniscus and the tibia; and passing the suturing element between the first arm and second arm of the suture passer.

11. A method of forming a loop of suture around a torn meniscus of a knee using a suture passer, the meniscus having an apex, a superior surface adjacent a femur, and an inferior surface adjacent a tibia, the method comprising:
passing a suturing element from the inferior surface of the meniscus on a first side of the torn meniscus, through the meniscus, to the superior surface of the meniscus and the femur, defining a first-side portion of the loop;
passing the suturing element from the inferior surface of the meniscus on a second side of the torn meniscus, through the meniscus to the superior surface of the meniscus and the femur defining a second-side portion of the loop; and
coupling the first and second side portions to form the loop around the torn meniscus.

12. The method of claim 11 wherein coupling further comprises placing a knot on the superior surface.

13. The method of claim 11 wherein the suture passer is withdrawn from the knee before passing the suturing element from a region between the inferior surface of the meniscus and the tibia on a second side and after passing the suturing element from a region between the inferior surface of the meniscus and the tibia on the first side.

14. The method of claim 11 wherein the suture passer is withdrawn from the knee after passing the suturing element from the inferior surface of the meniscus on the second side of the torn meniscus.

15. The method of claim 11 wherein both ends of the suturing element are removed from the knee before passing the suturing element from a region between the inferior surface of the meniscus and the tibia on a second side of the torn meniscus.

16. The method of claim 11 wherein both ends of the suturing element are removed from the knee after passing the suturing element from a region between the inferior surface of the meniscus and the tibia on a second side of the torn meniscus.

17. The method of claim 11 further comprising coupling the first and second side portions to form a secure loop around the torn meniscus using a knot pusher for placing a knot on the superior surface.

18. The method of claim 11 wherein coupling the first and second side portions comprises securing the suture element loop using a knot.

19. The method of claim 11, wherein the first-side potion and the second-side portion are radially spaced from each other, to form a vertical loop around the torn meniscus.

20. The method of claim 19 further comprising securing the vertical loop using a knot.

21. A method of repairing a meniscus in a knee joint, the meniscus having an apex, a superior surface adjacent a femur, and an inferior surface adjacent a tibia, the method comprising:
using a suture passer to pass a suture from the inferior surface of the meniscus, through the meniscus, towards the superior surface of the meniscus, across the inferior surface of the meniscus, and again back through the meniscus from the inferior surface towards the superior surface of the meniscus and thereby form a portion of a suture loop around a tear in the meniscus; and
securing the suture loop using a knot.

22. The method of claim 21 wherein the suture element loop forms a vertical loop around the tear in the meniscus.

* * * * *